(12) United States Patent
Li et al.

(10) Patent No.: US 10,543,189 B2
(45) Date of Patent: Jan. 28, 2020

(54) 2-ACETYLNAPHTHO[2,3-B]FURAN - 4,9-DIONE FOR USE ON TREATING CANCER

(71) Applicant: Boston Biomedical, Inc., Cambridge, MA (US)

(72) Inventors: Chiang Jia Li, Cambridge, MA (US); Wei Li, Wayland, MA (US); David Leggett, Milton, MA (US); Youzhi Li, Westwood, MA (US); David Kerstein, Cambridge, MA (US); Matthew Hitron, Cambridge, MA (US)

(73) Assignee: Boston Biomedical, Inc., Cambridge, MA (US)

( * ) Notice: Subject to any disclaimer, the term of this patent is extended or adjusted under 35 U.S.C. 154(b) by 0 days.

(21) Appl. No.: 16/543,089

(22) Filed: Aug. 16, 2019

(65) Prior Publication Data

US 2019/0388382 A1    Dec. 26, 2019

Related U.S. Application Data

(63) Continuation of application No. 16/220,636, filed on Dec. 14, 2018, now abandoned, which is a continuation of application No. 14/783,184, filed as application No. PCT/US2014/033566 on Apr. 9, 2014, now abandoned.

(60) Provisional application No. 61/810,117, filed on Apr. 9, 2013, provisional application No. 61/830,068, filed on Jun. 1, 2013, provisional application No. 61/932,179, filed on Jan. 27, 2014, provisional application No. 61/938,386, filed on Feb. 11, 2014.

(51) Int. Cl.
| | | |
|---|---|---|
| *A61K 31/343* | (2006.01) | |
| *A61K 47/14* | (2017.01) | |
| *A61K 9/48* | (2006.01) | |
| *A61K 31/337* | (2006.01) | |
| *A61K 45/06* | (2006.01) | |

(52) U.S. Cl.
CPC .......... *A61K 31/343* (2013.01); *A61K 9/4858* (2013.01); *A61K 31/337* (2013.01); *A61K 45/06* (2013.01); *A61K 47/14* (2013.01)

(58) Field of Classification Search
CPC ... A61K 31/343; A61K 9/4858; A61K 31/337
See application file for complete search history.

(56) References Cited

U.S. PATENT DOCUMENTS

| | | | |
|---|---|---|---|
| 2,472,133 A | 6/1949 | Viktor et al. | |
| 5,595,721 A | 1/1997 | Kaminski et al. | |
| 5,677,095 A | 10/1997 | Kikuchi et al. | |
| 5,736,137 A | 4/1998 | Anderson et al. | |
| 5,846,534 A | 12/1998 | Waldmann et al. | |
| 6,235,883 B1 | 5/2001 | Jakobovits et al. | |
| 6,337,346 B1 | 1/2002 | Lee et al. | |
| 6,395,773 B1 | 5/2002 | Hirai et al. | |
| 6,682,736 B1 | 1/2004 | Hanson et al. | |
| 6,828,337 B2 | 12/2004 | Belloni et al. | |
| 6,984,720 B1 | 1/2006 | Korman et al. | |
| 6,994,862 B2 | 2/2006 | Jeong et al. | |
| 7,019,147 B1 | 3/2006 | Barth et al. | |
| 7,090,843 B1 | 8/2006 | Francisco et al. | |
| 7,169,901 B2 | 1/2007 | Baca et al. | |
| 7,422,739 B2 | 9/2008 | Anderson et al. | |
| 7,435,797 B2 | 10/2008 | Lowman et al. | |
| 7,538,234 B2 | 5/2009 | Iida et al. | |
| 7,560,111 B2 | 7/2009 | Kao et al. | |
| 7,572,442 B2 | 8/2009 | Thorpe et al. | |
| 7,691,977 B2 | 4/2010 | Fuh et al. | |
| 7,758,859 B2 | 7/2010 | Fuh et al. | |
| 7,807,798 B2 | 10/2010 | Jakobovits et al. | |
| 7,824,679 B2 | 11/2010 | Hanson et al. | |
| 7,910,104 B2 | 3/2011 | Carr et al. | |
| 7,910,752 B2 | 3/2011 | Tokuda et al. | |
| 7,943,743 B2 | 5/2011 | Korman et al. | |
| 8,008,449 B2 | 8/2011 | Korman et al. | |
| 8,101,177 B2 | 1/2012 | Fuh et al. | |
| 8,119,775 B2 | 2/2012 | Moretta et al. | |
| 8,143,379 B2 | 3/2012 | Hanson et al. | |
| 8,168,179 B2 | 5/2012 | Honjo et al. | |
| 8,217,149 B2 | 7/2012 | Irving et al. | |
| 8,354,509 B2 | 1/2013 | Carven et al. | |
| 8,440,190 B2 | 5/2013 | Waldmann et al. | |

(Continued)

FOREIGN PATENT DOCUMENTS

| | | |
|---|---|---|
| AU | 2015218436 | 9/2015 |
| AU | 2017203239 | 6/2017 |
| CA | 2107806 | 4/1994 |
| CA | 2959931 | 9/2011 |
| CA | 2959951 | 9/2011 |
| EP | 0466094 | 1/1992 |
| EP | 0592366 | 4/1994 |
| EP | 1897540 | 3/2008 |
| EP | 2436669 | 4/2012 |

(Continued)

OTHER PUBLICATIONS

Panigrahi; Future Journal of Pharmaceutical Sciences, 4, 2018, 102-108.*

(Continued)

*Primary Examiner* — Pancham Bakshi

(74) *Attorney, Agent, or Firm* — Fish & Richardson P.C.

(57) ABSTRACT

The invention provides naphthofuran compounds, polymorphs of naphthofuran compounds, naphthofuran compounds in particle form, purified compositions that contain one or more naphthofuran compounds, purified compositions that contain one or more naphthofuran compounds in particle form, and methods of using these naphthofuran compounds, polymorphs, purified compositions and/or particle forms to treat subjects in need thereof.

15 Claims, 14 Drawing Sheets

(56) References Cited

U.S. PATENT DOCUMENTS

| | | |
|---|---|---|
| 8,529,902 B2 | 9/2013 | Teeling et al. |
| 8,617,554 B2 | 12/2013 | Roberts et al. |
| 8,623,357 B2 | 1/2014 | Waldmann et al. |
| 8,685,394 B2 | 4/2014 | Jure-Kunkel |
| 8,716,452 B2 | 5/2014 | Jure-Kunkel |
| 8,779,108 B2 | 7/2014 | Queva et al. |
| 8,784,815 B2 | 7/2014 | Korman et al. |
| 8,802,091 B2 | 8/2014 | Johnson et al. |
| 8,877,803 B2 | 11/2014 | Jiang et al. |
| 8,900,587 B2 | 12/2014 | Carven et al. |
| 8,952,136 B2 | 2/2015 | Carven et al. |
| 8,977,803 B2 | 3/2015 | Horn et al. |
| 8,981,065 B2 | 3/2015 | Moretta et al. |
| 9,062,113 B2 | 6/2015 | Weber et al. |
| 9,084,766 B2 * | 7/2015 | Li .................... A61K 31/27 |
| 9,096,672 B2 | 8/2015 | Weber et al. |
| 9,102,725 B2 | 8/2015 | Korman et al. |
| 9,150,530 B2 | 10/2015 | Jiang et al. |
| 9,150,656 B2 | 10/2015 | Johnson et al. |
| 9,212,224 B2 | 12/2015 | Cogswell et al. |
| 9,220,776 B2 | 12/2015 | Sharma et al. |
| 9,328,345 B2 | 5/2016 | Li et al. |
| 9,381,184 B2 | 7/2016 | Li et al. |
| 9,730,909 B2 * | 8/2017 | Li .................... A61K 31/343 |
| 9,732,055 B2 * | 8/2017 | Li .................... A61K 31/38 |
| 9,745,278 B2 | 8/2017 | Li et al. |
| 9,834,532 B2 | 12/2017 | Jang et al. |
| 10,377,731 B2 | 8/2019 | Li et al. |
| 2004/0006009 A1 | 1/2004 | Larsen et al. |
| 2004/0092428 A1 | 5/2004 | Chen et al. |
| 2004/0138140 A1 | 7/2004 | Xu et al. |
| 2004/0138189 A1 | 7/2004 | Sebti et al. |
| 2005/0010060 A1 | 1/2005 | Blokhin et al. |
| 2005/0049207 A1 | 3/2005 | Kaufmann |
| 2006/0019256 A1 | 1/2006 | Clarke et al. |
| 2006/0099251 A1 | 5/2006 | Johannsson |
| 2006/0142271 A1 | 6/2006 | Muller et al. |
| 2006/0222696 A1 | 10/2006 | Okada et al. |
| 2006/0247318 A1 | 11/2006 | Song et al. |
| 2006/0252674 A1 | 11/2006 | Peritt et al. |
| 2006/0279011 A1 | 12/2006 | Palakodaty et al. |
| 2007/0009532 A1 | 1/2007 | Sikic et al. |
| 2007/0060521 A1 | 3/2007 | Jove et al. |
| 2007/0123502 A1 | 5/2007 | Turkson et al. |
| 2007/0207980 A1 | 9/2007 | Salama et al. |
| 2007/0238770 A1 | 10/2007 | Gougoutas et al. |
| 2009/0042977 A1 | 2/2009 | Tokuda et al. |
| 2010/0297118 A1 | 11/2010 | Macdougal et al. |
| 2010/0310503 A1 | 12/2010 | Li et al. |
| 2011/0008331 A1 | 1/2011 | Triebel |
| 2011/0112180 A1 | 5/2011 | Jiang et al. |
| 2012/0077986 A1 | 3/2012 | Iida et al. |
| 2012/0252763 A1 | 10/2012 | Li et al. |
| 2013/0028944 A1 | 1/2013 | Li et al. |
| 2013/0034591 A1 | 2/2013 | Li et al. |
| 2015/0018410 A1 | 1/2015 | Jiang et al. |
| 2015/0183756 A1 | 7/2015 | Li et al. |
| 2015/0307609 A1 | 10/2015 | Lonberg et al. |
| 2016/0030384 A1 | 2/2016 | Li et al. |
| 2016/0060344 A1 | 3/2016 | Narwal et al. |
| 2016/0220494 A1 | 8/2016 | Stroyer et al. |
| 2016/0271099 A1 | 9/2016 | Li et al. |
| 2017/0197932 A1 | 7/2017 | Jiang et al. |
| 2017/0319537 A1 | 11/2017 | Li et al. |
| 2018/0030021 A1 | 2/2018 | Li et al. |
| 2018/0030022 A1 | 2/2018 | Li et al. |
| 2018/0098959 A1 | 4/2018 | Li et al. |
| 2018/0140572 A1 | 5/2018 | Li et al. |
| 2018/0250260 A1 | 9/2018 | Li et al. |
| 2018/0250261 A1 | 9/2018 | Li et al. |
| 2018/0333385 A1 | 11/2018 | Li et al. |
| 2019/0076392 A1 | 3/2019 | Li et al. |
| 2019/0135773 A1 | 5/2019 | Li et al. |
| 2019/0224157 A1 | 7/2019 | Li et al. |
| 2019/0231735 A1 | 8/2019 | Li et al. |

FOREIGN PATENT DOCUMENTS

| | | |
|---|---|---|
| EP | 3108750 | 12/2016 |
| JP | 63196576 | 8/1988 |
| JP | 04139177 | 5/1992 |
| JP | H 09249560 | 9/1997 |
| JP | 1121284 | 1/1999 |
| JP | 1165141 | 3/1999 |
| JP | 2004224802 | 8/2004 |
| JP | 2007145680 | 6/2007 |
| JP | 2012092083 | 5/2012 |
| JP | 2016016973 | 2/2016 |
| JP | 6199787 | 9/2017 |
| SU | 1049490 | 10/1983 |
| WO | WO 99/62909 | 12/1999 |
| WO | WO 00/44774 | 8/2000 |
| WO | WO 2000/059473 | 10/2000 |
| WO | WO 01/23372 | 4/2001 |
| WO | WO 01/168139 | 9/2001 |
| WO | WO 2004/026253 | 4/2004 |
| WO | WO 2004/046120 | 6/2004 |
| WO | WO 2004/045593 | 8/2004 |
| WO | WO 2005/033048 | 4/2005 |
| WO | WO 2005/056055 | 6/2005 |
| WO | WO 2005/058829 | 6/2005 |
| WO | WO 2005/110477 | 11/2005 |
| WO | WO 2006/014359 | 2/2006 |
| WO | WO 2006/018627 | 2/2006 |
| WO | WO 2006/052712 | 5/2006 |
| WO | WO 2006/056399 | 6/2006 |
| WO | WO 2006/065894 | 6/2006 |
| WO | WO 2006/091837 | 8/2006 |
| WO | WO 2006/098355 | 9/2006 |
| WO | WO 2006/113790 | 10/2006 |
| WO | WO 2007/056470 | 5/2007 |
| WO | WO 2007/061880 | 5/2007 |
| WO | WO 2007/074347 | 7/2007 |
| WO | WO 2007/087129 | 8/2007 |
| WO | WO 2007/092620 | 8/2007 |
| WO | WO 2007/095753 | 8/2007 |
| WO | WO 2007/100640 | 9/2007 |
| WO | WO 2007/115269 | 10/2007 |
| WO | WO 2008/077062 | 6/2008 |
| WO | WO 2008/094321 | 8/2008 |
| WO | WO 2009/036059 | 3/2009 |
| WO | WO 2009/036099 | 3/2009 |
| WO | WO 2009/036101 | 3/2009 |
| WO | WO 2009/060282 | 5/2009 |
| WO | WO 2010/027827 | 3/2010 |
| WO | WO 2011/008331 | 1/2011 |
| WO | WO 2011/066342 | 6/2011 |
| WO | WO 2011/084694 | 7/2011 |
| WO | WO 2011/116398 | 9/2011 |
| WO | WO 2011/116399 | 9/2011 |
| WO | WO 2012/119265 | 9/2012 |
| WO | WO 2013/166618 | 11/2013 |
| WO | WO 2013/172918 | 11/2013 |
| WO | WO 2013/173223 | 11/2013 |
| WO | WO 2014/169078 | 10/2014 |
| WO | WO 2015/155673 | 10/2015 |
| WO | WO 2015/190489 | 12/2015 |
| WO | WO 2016/044234 | 3/2016 |
| WO | WO 2016/168856 | 10/2016 |
| WO | WO 2016/168857 | 10/2016 |
| WO | WO 2016/196935 | 12/2016 |
| WO | WO 2017/132049 | 8/2017 |
| WO | WO 2018/096401 | 5/2018 |
| WO | WO 2018/183089 | 10/2018 |
| WO | WO 2018/213424 | 11/2018 |

OTHER PUBLICATIONS

U.S. Appl. No. 16/148,561, Li et al., filed Oct. 1, 2018.
U.S. Appl. No. 16/170,756, Li et al., filed Oct. 25, 2018.
U.S. Appl. No. 16/188,924, Li et al., filed Nov. 13, 2018.
U.S. Appl. No. 16/220,636, Li et al., filed Dec. 14, 2018.
U.S. Appl. No. 16/236,948, Li et al., filed Dec. 31, 2018.
U.S. Appl. No. 16/287,775, Li et al., filed Feb. 27, 2019.

(56) References Cited

OTHER PUBLICATIONS

U.S. Appl. No. 16/313,748, Li et al., filed Dec. 27, 2018.
U.S. Appl. No. 16/363,427, Li et al., filed Mar. 25, 2019.
U.S. Appl. No. 16/363,626, Li et al., filed Mar. 25, 2019.
U.S. Appl. No. 16/246,829, Li et al., filed Jan. 14, 2019.
Achcar et al., "Expression of Activated and Latent Signal Transducer and Activator of Transcription 3 in 303 Non-Small Cell Lung Carcinomas and 44 Malignant Mesotheliomas: Possible Role for Chemotherapeutic Intervention," Arch Pathol Lab Med., 2007, 131(9):1350-60.
Ailles and Weissman, "Cancer Stem Cells in Solid Tumors," Curr Opin Biotechnol, 2007, 18(5):460-466.
Ajani et al., "Cancer Stem Cells: The Promise and the Potential," Semin Oncol., Apr. 2015, 42(1):53-17.
Alas, S, "Inhibition of Constitutive STAT3 Activity Sensitizes Resistant Non-Hodgkin's Lymphoma and Multiple Myeloma to Chemotherapeutic Drug-Mediated Apoptosis", Clin Cancer Res, 2003, 9(1):316-26.
Al-Hajj, M., et al., "Prospective Identification of Tumorigenic Breast Cancer Cells", Proc. Natl. Acad. Sci. USA, Apr. 1, 2003, 100(7):3983-3988.
Alvarez et al., "Genome-wide analysis of STAT target genes: elucidating the mechanism of STAT-mediated oncogenesis," Cancer Biology & Therapy, 2004,3(11):1045-1050.
Alvarez et al., "Identification of a genetic signature of activated signal transducer and activator of transcription 3 in human tumors," Cancer Res., 2005, 65(12):5054-62.
Alvi, "Functional and Molecular Characterization of Mammary Side Population Cells," Breast Cancer Res, 2003, 5(1):R1-R8.
Amin, "Selective inhibition of STAT3 induces apoptosis and G(1) cell cycle arrest in ALK-positive anaplastic large cell lymphoma", Oncogene, 2004, 23(32):5426-5434.
Anderson, "The Process of Structure-Based Drug Design," Chem and Biol, 2003 10:787-797.
Aoki et al., "Inhibition of STAT3 signaling induces apoptosis and decreases survivin expression in primary effusion lymphoma," Blood, 2003, 101(4):1535-1542.
Arany, "Correlation Between Pretreatment Levels of Interferon Response Genes and Clinical Responses to an Immune Response Modifier (Imiquimod) in Genital Warts," Antimicrob Agents Chemother, 2000, 44(7):1869-73.
Bandhavkar, "Cancer stem cells: a metastasizing menace!," Cancer Medicine, 2016, 5(4):649-655.
Barton et al., "Signal transducer and activator of transcription 3 (STAT3) activation in prostate cancer: Direct STAT3 inhibition induces apoptosis in prostate cancer lines," Mol CancerTher., 2004, 3(1):11-20.
Baumann, "Exploring the Role of Cancer Stem Cells in Radioresistance", Nat. Rev. Cancer. 8.7, (2008), 8(7):545-554.
Becourn et al., "Folfiri and Bevacizumab in first-line treatment for colorectal cancer patients: safety, efficacy and genetic polymorphisms," BMC Reasearch Notes, 2014, 7:260.
Benekli et al., "Constitutive activity of signal transducer and activator of transcription 3 protein in acute myeloid leukemia blasts is associated with short disease-free survival," Blood, 2002, 99(1):252-257.
Benkhart, "Role of Stat3 in Lipopolysaccharide-lnduced IL-1O gene expression," J lmmunol, 2000, 165(3):1612-1617.
Berishaj et al., "Stat3 is tyrosine-phosphorylated through the interleukin-6/glycoprotein 130/Janus kinase pathway in breast cancer," Breast Cancer Res., 2007, 9(3):R32.
Berge et al., "Pharmaceutical Salts," J Pharma Sci, 1977, 66:1-19.
Blaskovich et al., "Discovery of JSI-124 (cucurbitacin I), a selective Janus kinase/signal transducer and activator of transcription 3 signaling pathway inhibitor with potent antitumor activity against human and murine cancer cells in mice," Cancer Res, 2003, 63(6):1270-1279.
Bleau, "New Strategy for the analysis of phenotypic marker antigens in brain tumor-derived neurospheres in mice and humans", Neurosurg Focus, 2008, 24(3-4):E28.

Boman et al., "Human colon cancer stem cells: a new paradigm in gastrointestinal oncology," J Clin Oncol., 2008, 26(17): 2828-2838.
Boman et al., "Cancer stem cells: a step toward the cure," J Clin Oncol 2008, 26(17):2795-99.
Bonnet and Dick, "Human acute myeloid leukemia is organized as a hierarchy that originates from a primitive hematopoietic cell," 1997, 3(7):730-737.
Bonnet, "Normal and leukaemic stem cells", Br J Haematol, (2005), 130(4):469-479.
Borovski T, "Cancer stem cell niche: the place to be," Cancer Res 2011, 71(3):634-639.
Bostonbiomedical.com, "Boston Biomedical Data at ASCO 2015 Highlights Potential of Novel Investigational Cancer Stem Cell Pathway Inhibitors BBI608 and BBI503 in Multiple Cancer Types", retrieved on [Jun. 1, 2015] retrieved from URL<http://www.bostonbiomedical.com/boston-biomedical-data-at-asco-2015-highlights-potential-of-novel-investigationsal-cancer-stem-cell-pathway-inhibitors-bbi608-and-bbi-503-in-multiple-cancer-types/>, 4 pages.
Braatz, "Crystallization: Particle Size Control," Encyclopedia of Pharmaceutical Technology, Swarbrick, ed. New York: lnforma Healthcare, Third Edition, 2007, 858-871.
Bromberg, "Stat3 as an Oncogene," Cell, 1999, 98(3):295-303.
Bromberg, J., "Stat proteins and oncogenesis," J Clin Invest, 2002, 109(9):1139-1142.
Buettner et al., "Activated STAT signaling in human tumors provides novel molecular targets for therapeutic intervention," Clinical Cancer Research, 2002, 8(4): 945-954.
Burdelya, "Stat3 Activity in Melanoma Cells Affects Migration of Immune Effector Cells and Nitric Oxide-Mediated Antitumor Effects," J lmmunol, 174(7):3925-31.
Burke, WM, et al., "Inhibition of Constitutively Active STAT-3 Suppresses Growth of Human Ovarian and Breast Cancer Cells", Oncogene, Nov. 29, 2001, 20(55):7925-7934.
Byrn, "Solid-State Chemistry of Drugs, 2d, Chapter 11 Hydrates and Solvates/Hydrates," 233-247.
Caira, "Crystalline Polymorphism of Oeganic Compounds, Topics in Chemistry," 1998, 198:163-208.
Campbell, "Cytokine-Mediated Inflammation, Tumorigenesis, and Disease Associated JAKlSTA/SOCS Signaling Circuits in the CNS," Brain Res Brain Res Rev, 2005, 48(2): 166-77.
Carson, "Interferon-Alpha-Induced Activation of Signal Transducer and Activator of Transcription Proteins in Malignant Melanoma," Clin Cancer Res, 1998, 4(9):2219-2228.
Catlett-Falcone et al. "Constitutive Activation of Stat3 Signaling Confers Resistance to Apoptosis in Human U266 Myeloma Cells," Immunity, 1999, 10(1):105-115.
Cains, "Classical Methods of Preparation of Polymorphs and Alternative Sold Forms," Polymorphism in Pharmaceutical Solids, 2nd Edition, 2009, 70 pages.
Cesari, "Inflammatory Markers and Onset of Cardiovascular Events: Results from the Health ABC Study," Circulation, 2003 108(19):2317-2322.
Chan et al., "Disruption of Stat3 reveals a critical role in both the initiation and the promotion stages of epithelial carcinogenesis," J. Clin. Invest., 2004, 114:720-728.
Chang et al., "Activation of STAT3 in thymic epithelial tumours correlates with tumour type and clinical behavior," J Pathol, 2006, 210(2):224-233.
Chen et al., "Signal transducer and activator of transcription 3 is involved in cell growth and survival of human rhabdomyosarcoma and osteosarcoma cells," BMC Cancer, 2007, 7:111.
Chen et al., "Constituents of Markhamia Hildebrandtii (Baker) Sprague and their Antitumor Activity", STN Database Accession No. 1986:568912,Chemical Abstracts Service, Columbus, OH XP002662423, Nov. 15, 1986, 2 pgs.
Chen et al., "Stat3 activation in human endometrial and cervical cancers," Br J Cancer., 2007, 96(4):591-599.
Cho-Vega et al., "Suppressor of cytokine signaling 3 expression in anaplastic large cell lymphoma," Leukemia, 2004 18(11):1872-1878.
Clarke, "Self-renewal and solid-tumor stem cells," Biol Blood Marrow Transplant, Feb. 2005, 11(2 suppl 2):14-16.

(56) References Cited

OTHER PUBLICATIONS

Clarke, "Cancer Stem Cells—Perspectives on Current Status and Future Directions: AACR Workshop on Cancer Stem Cells," Cancer Research, 2006, 66(19):9339-44.
Clinicaltrials.com, "A Study of BBI603 Administered With Paclitaxel in Adult Patients With Advanced Malignancies", ID NCT01325441, Boston Biomedical, [retrieved on Feb. 19, 2016] Retrieved from URL <http://clinicaltrials.gov/archive/ NCTO 1325441/2011_03_28>, 3 pages.
Clinicaltrials.com, "A Study of BBI608 in Adult Patients with Advanced, Refractory Hematologic Malignancies," ID NCT02352558, Boston Biomedical, [retrieved on Feb. 19, 2016] Retrieved from URL <https://clinicaltrials.gov/ct2/show/NCT02352558?term=BBI608&rank=1>, 5 pages.
Clinicaltrials.com, "A Study of BBI608 in Combination with Standard Chemotherapies in Adult Patients with Advanced Gastrointestinal Cancer," ID NCT02024607, Boston Biomedical, [retrieved on Feb. 19, 2016] Retrieved from URL <https://clinicaltrials.gov/ct2/show/NCT02024607?term=bbi608&rank=3>, 7 pages.
Clinicaltrials.com, "A Study of BBI608 in Combination with Temozolomide in Adult Patients with Recurrent or progressed Glioblastoma," ID NCT02315534, [retrieved on Feb. 19, 2016] Retrieved from URL <https://clinicaltrials.gov/ct2/show/NCT02315534?term=BBI608&rank=10.
Clinicaltrials.com, "A Study of BBI608 in Combination with Standard Chemotherapies in Adult Patients with Pancreatic Cancer," ID NCT02231723, [retrieved Mar. 19, 2019] Retrieved from URL <https://clinicaltrials.gov/ct2/show/NCT02231723>, 15 pages.
Clinicaltrials.com, "A Study of BBI608 Administered in Combination With Immune Checkpoint Inhibitors in Adult Patients With Advanced Cancers," ID NCT02467361, [retrieved Aug. 16, 2019] Retrieved from URL <https://clinicaltrials.gov/ct2/show/NCT02467361>, 9 pages.
Collins, "Prospective Identification of Tumorigenic Prostate Cancer Stem Cells," Cancer Res, 2005, 65(23):10946-10951.
Colman et al., "Effect of a small molecule inhibitor of the JAK2/STAT3 pathway on self-renewal of glioblastoma stem cells," Journal of Clinical Oncology, 2008, 26:15S.
Colman de Saizarbitoria et al., "Bioactive furonaphthoquinones from Tabebuia barbata (Bignoniaceae)," Acta Cient Venez, 1997, 48(1):42-46.
Corvinus et al., "Persistent STAT3 activation in colon cancer is associated with enhanced cell proliferation and tumor growth," Neoplasia, 2005, 7(6):545-555.
Dalerba, "Phenotypic Characterization of Human Colorectal Cancer Stem Cells," Proc Natl Acad Sci USA, Jun. 2007, 104(24):10158-10163.
Darnell et al., "Validating Stat3 in cancer therapy", Nature Medicine, Jun. 2005, 11(6):595-596.
De Araujo et al. "STAT3 expression in salivary gland tumours," Oral Oneal., 2008, 44(5):439-45.
De Boer, "Liposomal doxorubicin in metastatic breast cancer," Breast Cancer Res., 1999, 2:66629-66631.
Dean et al., "Tumour Stem Cells and Orig Resistance", Nat Rev Cancer, 2005, 5:275-284.
"Definition of Cancer", MedicineNet.com., [Online] retrieved from the internet: <http://www.medterms.com>, (2004).
General Correspondence from Boston Biomedical to Department of Health and Human Services Investigational New Drug Application, Napabucasin, IND 100887, Serial No. 0179, Dec. 22, 2017, 8 pages.
Desmond et al., "The Synthetic Furanonaphthoquinone Induces Growth Arrest, Apoptosis and Differentiation in a Variety of Leukaemias and Multiple Myeloma Cells." Brit. J. Haematol., 2005, 131(4):520-529.
Diaz et al., "Furanonaphthoquinones from Tabebuia ochracea ssp. neochrysanta", J. Nat. Prod., 1996, 59(4):423-424.
Diaz et al., "Activation of stat3 in primary tumors from high-risk breast cancer patients is associated with elevated levels of activated SRC and survivin expression," Clin Cancer Research, 2006, 12(1):20-8.
Dien et al., "Signal Transducers and Activators of Transcription-3 Up-Regulates Tissue Inhibitor of Metalloproteinase-1 Expression and Decreases Invasiveness of Breast Cancer," Am J of Pathology., 2006, 169(2):633-642.
Doyle and Ross, "Multidrug Resistance Mediated by the Breast Cancer Resistance Protein BCRP (ABCG2)", Oncogene, 2003, 22(47):7340-7358.
Epling-Burnette et al., "Inhibition of STAT3 signaling leads to apoptosis of leukemic large granular lymphocytes and decreased Mcl-1 expression," J. Clin. Invest., 2001, 107(3):351-362.
Elzagheid, Adam, et al., "Nuclear [beta]-catenin expression as a prognostic factor in advanced colorectal carcinoma", World Journal of Gastroenterology, Jun. 28, 2008, 14(24):3866-3871.
Eyler, "Survival of the Fittest: Cancer Stem Cells in Therapeutic Resistance and Angiogenesis", J. Clin. Oneal., 2008, 26(17):2839-2845.
Eyong, et al., "Semisynthesis and antitumoral activity of 2-acetylfuranonaphthoquinone and other naphthoquinone derivatives from lapachol", Bioorganic & Medicinal Chemistry Letters, 2008, 18(20):5387-5390.
Fagerholm, "Experimental Estimation of the Effective Unstirred Water Layer Thickness in the Human Jejunum, and its Importance in Oral Drug Absorption," Eur. J. Pharm. 1995, 3:247-253.
Faloppi et al, "The correlation between LDH serum levels and clinical outcome in advanced biliary tract cancer patients treated with first line chemotherapy," Scientific Reports, 2016, 6:24136.
Farina, F., et al., "La Reaccion De La 2-Acetil-1.4-Benzoouinona V Ouinonas Analogas Con Tioles. Aplicacion a La Sintesis De Tiofenouinonas", Analesde Quimica, 1976, (72):902-908.
Feldmann, M, "Role of Cytokines in Rheumatoid Arthritis", Annu Rev lmmunol, 1996, 14:397-440.
Fotsing, "Identification of an Anti-Inflammatory Principle from the Stem Bark of Millettia Versicolor," Planta Med, Aug. 1, 2003, 69(8):767-70.
Frank, "ABCB5-Mediated Doxorubicin Transport and Chemoresistance in Human Malignant Melanoma," Cancer Res, 2005, 65(10):4320-4333.
Frank, "STAT3 as a Central Mediator of Neoplastic Cellular Transformations," Cancer Left., 2007, 251(2):199-210.
Fu, "STAT3 in Immune Responses and Inflammatory Bowel Disease," Cell Res, 16(2):214-219(2006).
Furqan, et al., "STAT inhibitors for cancer therapy," J Hematology & Oncology, 2013, 6:90.
Gafner, "Antifungal and Antibacterial Naphthoquinones from Newbouldia laevis Roots," Phytochemistry., 2007, 42(5):1315-1320.
Gao et al., "Inhibition of STAT3 expression by siRNA suppresses growth and induces apoptosis in laryngeal cancer cells," Acta Pharmacol Sin., 2005, 26(3):377-383.
Gao et al., "Knockdown of Stat3 expression using RNAi inhibits growth of laryngeal tumors in vivo," Acta Pharmacol Sin., 2006, 27(3):347-352.
Gao et al., "Constitutive activation of JAK-STAT3 signaling by BRCA1 in human prostate cancer cells," FEBS Letters, 2001, 488(3):179-184.
Garcia et al., "Constitutive activation of Stat3 in fibroblasts transformed by diverse oncoproteins and in breast carcinoma cells," Cell Growth Differ, 1997, 8(12):1267-1276.
Garcia, "Constitutive activation of Stat3 by the Src and JAK tyrosine kinases participates in growth regulation of human breast carcinoma cells", Oncogene, 2001, 20:2499-2513.
Goodell, "Isolation and Functional Properties of Murine Hematopoietic Stem Cells That are Replicating in Vivo," J. Exp. Med. 183. 4(1996):1797-1806.
Gormann, "Furanonaphthoquinones, Atraric Acid and a Benzofuran from the Stem Barks of Newbouldia Laevis," Phytochemistry, 64.2(2004):583-587.
Grandis et al., "STAT signaling in head and neck cancer," Oncogene, 2000, 19(21):2489-2495.
Gritsko et al. "Persistent activation of stat3 signaling induces survivin gene expression and confers resistance to apoptosis in human breast cancer cells," Clinical Cancer Research Center, 2006, 12(1):11-19.

(56) References Cited

OTHER PUBLICATIONS

Gupta, et al., "Cancer stem cells: mirage or reality?" Nat Med, Sep. 2009, 15(9):1010-1012.
Hisahiro, Hagiwara, et al., "Domino Michael-O-alkylation reaction: one-pot synthesis of 2,4-diacylhydrofuran derivatives and its application to antitumor naphthofuran synthesis", J. Chem. Soc., Perkin Trans., 2001, 22:2946-2957.
Hagiwara, et al., "Tandem nucleophilic reaction leading to hydrofurans: application to one-pot synthesis of antitumor naphthofuran natural product", Heterocycles, 1999, (51)3:497-500.
Hagler et al., "Sophorolipids Decrease IgE Production in U266 Cells by Downregulation of BSAP (Pax5), TLR-2, STAT3 and IL-6," J Allergy Clin Immunol, 119(1):S263.
Haleblian, "Pharmaceutical Applications of Polymorphism," J. Pharm. Sci. Aug. 1969, 58(8):911-29.
Hambardzumyan, "Radiation Resistance and Stem-Like Cells in Brain Tumors," Cancer Cell, 2006, 10(6):454-456.
Han Li., "Unusual Naphthoquinone Derivatives from the Twigs of Avicennia Marina," J. Nat. Prod., 2007, 70:923-927.
Harada, T, "Increased Expression of STAT3 in SLE T Cells Contributes to Enhanced Chemokine-Mediated Cell Migration", Autoimmunity, 2006, 40:1-8.
Haraguchi, "Characterization of a Side Population of Cancer Cells from Human Gastrointestinal System," Stem Cells, 2006, 24(3):506-513.
Harris, "Cutting Edge: An in Vivo Requirements for STAT3 Signaling in TH17 Development and TH17-dependent Autoimmunity," J Immunol, 179(7):4313-4317.
Hart, H, "Organic Chemistry: A Short Course", Houghton Mifflin Harcourt College Division, Boston, Massachusetts, 9th Edition, 1995, 279.
Haura et al., "Activated epidermal growth factor receptor-Stat-3 signaling promotes tumor survival in vivo in non-small cell lung cancer," Clin Cancer Res, 2005, 11(23):8288-8294.
He et al., "Prodrugs of Phosphonates, Phosphinates, and Phosphates," Prodrugs, 2007, pp. 224-264.
Hirai et al., "Furanonaphthoquinone derivatives as antiviral, antifungal and antibacterial agents," STN Database Accession No. 1997:632811, 1 pg.
Hirai, "Furanonaphthoquinone Analogs Possessing Preferential Antitumor Activity Compared to Normal Cells," Cancer Detection and Prevention, 1999 23(6):539-550.
Hironaka, Shuichi, et al., "Weekly paclitaxel as second-line chemotherapy for advanced or recurrent gastric cancer", Gastric Cancer, Springer-Verlag, To, vol. 9, No. 1, (Feb. 1, 2006), 14-18.
Ho, "Side Population in Human Lung Cancer Cell Line and Tumors is Enriched with Stem-Like Cancer Cells," Cancer Res., 2007, 67(10):4827-4833.
Holtick et al., "STAT3 is essential for Hodgkin lymphoma cell proliferation and is a target of tyrphostin AG17 which confers sensitization for apoptosis," Leukemia., 2005, 19 (6):936-944.
Horiguchi et al., "Activation of signal transducer and activator of transcription 3 in renal cell carcinoma: a study of incidence and its association with pathological features and clinical outcome," The Journal of Urology, 2002, 168(2):762-765.
Hsiao et al., "Constitutive activation of STAT3 and STAT5 is present in the majority of nasopharyngeal carcinoma and correlates with better prognosis," Br J Cancer., 2003, 89(2):344-349.
Huang, M., et al., "Constitutive Activation of Stat 3 Oncogene Product in Human Ovarian Carcinoma Cells", Gynecologic Oncology, 2000, 79(1):67-73.
Hubbard et al., "Napabucasin: An Update on the First-in-Class Cancer Stemness Inhibitor," Drugs, Jul. 2017, 77(10):1091-1103.
Igawa et al., "Efficacy of chemotherapy with carboplatin and paclitaxel for unresectable thymic carcinoma," Lung Cancer, Feb. 2010, 67(2):194-197.
Ikegawa et al., "Furonaphthoquinone derivatives as antiviral, antifungal and antibacterial agents," STN Database Accession No. 1989:560194, 2 pages.
Ishihara and Hirano, "IL-6 in Autoimmune Disease and Chronic Inflammatory Proliferative Disease," Cytokine Growth Factor Rev, 2002, 13(4-5):357-368.
Itoh et al., "Requirement of STAT3 activation for maximal collagenase-1 (MMP-1) induction by epidermal growth factor and malignant characteristics in T24 bladder cancer cells," Oncogene, 2006, 25(8):1195-1204.
Itoigawa, "Cancer Chemopreventive Activity of Naphthoquinones and Their Analogs from *Avicennia* Plants," Cancer Letters, 2001, 174(2):135-139.
Ivashkiv and Tassiulas, "Can SOCS make Arthritis Better?," J Clin Invest, 2003, 111(6):795-797.
Iwamaru et al., "A novel inhibitor of the STAT3 pathway induces apoptosis in malignant glioma cells both in vitro and in vivo," Oncogene, 2007, 26(17):2435-44.
Johnson et al., "Abrogation of Signal Transducer and Activator of Transcription 3 Reactivation After Src Kinase Inhibition Results in Synergistic Antitumor Effects." Clin. Cancer Res. 13.14(2007):4233-4244.
Johnston et al. "STAT3 Signaling: Anticancer Strategies and Challenges." Mol. Interv. 11.1(2011):18-26.
Jones, "Cancer Stem Cells: Are We Missing the Target?," J Natl Cancer Inst, 2004, 96(8):583-585.
Jonker et al., "Napabucasin versus placebo in refractory advanced colorectal cancer: a randomized phase 3 trial." Lancet Gastroenterol Hepatol., Apr. 2018 2018, 3(4):263-270.
Jordan, "Cancer stem cells," N Engl J Med., Sep. 21, 2006, 355(12):1253-1261.
Kanda et al., "STAT3 is constitutively activated and supports cell survival in association with survivin expression in gastric cancer cells," Oncogene, 2004, 23(28):4921-4929.
Kang, "A New Route to Naphtho[2,3-b]furan-4,9-Diones from Thia-Substituted 1,4-Naphthoquinones," J. Chem. Soc. Perkin Trans., 1990, 441-445.
Katoh et al., "STAT3-Induced WNT5A Signaling Loop in Embryonic Stem Cells, Adult Normal Tissues, Chronic Persistent Inflammation, Rheumatoid Arthritis and Cancer," Int. J. Mol. Med., 2007, 19(2):273-278.
Kijima et al., "STAT3 activation abrogates growth factor dependence and contributes to head and neck squamous cell carcinoma tumor growth in vivo," Cell Growth Diff., 2002, 13:355-362.
Kikuchi, T., et al., "Electrophotographic Photosensitive Member", STN Database Accession No. 1992:245248, Chemical Abstracts Service, Columbus, OH XP002661424, (Jun. 13, 1992), 5 DOS.
Kim et al., "Inhibition of Signal Transducer and Activator of Transcription 3 Activity Results in Down-Regulation of Survivin Following Irradiation," Mol. Cancer Thera. 2006, 5(11):2659-2665.
Kim, "JAK-STAT Signaling Mediates Gangliosides-lnduced Inflammatory Responses in Brain Microglial Cells," J Biol Chem, 2002, 277(43):40594-40601.
Klein et al., "Increased Expression of Stem Cell Markers in Malignant Melanoma", Mod Pathol., 2007, 20:102-107.
Kortylewski, M, et al., "Inhibiting STAT3 Signaling in the Hematopoietic System Elicits Multicomponent Antitumor Immunity", Nat Med, 11(12):1314-1321.
Kobayashi et al., "One-Pot Synthesis of Naphtho[2,3-b]furan-4,9-diones by Sequential Coupling/Ring Closure Reactions", Tetrahedron Letters, 1997, 38(5):837-840.
Kobayashi et al., "An Improved Method for the Preparation of 4,7-Dioxo-4,7-dihydrobenzo[b]thiophene-2-carboxylates from 2-Acyl-1,4-benzoquinones and Mercaptoacetates,", Heterocyclesm, 2001, 55(21):2423-2429.
Kondo, "Persistence of a Small Subscription of Cancer Stem-Like Cells in the C6 Glioma Cell Line," Proc Natl Acad Sci USA, 2004, 101(3):781-786.
Konnikova et al., "Knockdown of STAT3 expression by RNAi induces apoptosis in astrocytoma cells," BMC Center 2003, 3:23.
Koyanagi, "A Facile Synthesis of 2-Acteylnaphtho[2,3-b]furan-4,9-Dione," Journal of Heterocyclic Chemistry, 1995, 32:1289-1291.
Koyanagi, "A New Synthetic of 2-Substituted Naphtho[2,3-b]furan-4,9-Dione," Journal of Heterocyclic Chemistry, 1997, 34:407-412.

(56) References Cited

OTHER PUBLICATIONS

Koyama et al., "Micellar Electrokinetic Chromatography (MEKC) Separation of Furanonaphthoquinones from Tabebuia Impetiginosa," Chem. Pharm. Bull. (Tokyo), Jun. 2000, 48(6):873-875.

Krause, "Rheumatoid Arthritis Synoviocyte Survival is Dependent on Stat3," J Immunol, 2002, 169(11):6610-6.

Kumar, "Clinical Trials and Progress with Paclitaxel in Ovarian Cancer," International Journal of Women's Health 2010, 2:411-427.

Kusaba et al., "Expression of p-STAT3 in human colorectal adenocarcinoma and adenoma; correlation with clinicopathological factors," Journal of Clinical Pathology, 2005, 58(8):833-838.

Lai et al., "STAT3 is activated in a subset of the Ewing sarcoma family of tumours," J Pathol. 2006, 208(5):624-632.

Lai, "Signal Transducer and Activator of Transcription-3 Activation Contributes to High Tissue Inhibitor of Metalloproteinase-1 Expression in Anaplastic Lymphoma Kinase-Positive Anaplastic Large Cell Lymphoma," Am J Pathol, 2004, 164(6):2251-58.

Lande, "The Relationship Between Membrane Fluidity and Permeabilities to Water, Solutes, Ammonia, and Protons," J. Gen. Physiol, 1995, 106:67-84.

Lassman et al., "STAT3 mRNA and protein expression in colorectal cancer: effects on STAT3-inducible targets linked to cell survival and proliferation," J Clin Pathol. 2007, 60(2): 173-9.

Lau et al., "Inhibition of Stat3 activity by YC-1 enhances chemosensitivity in hepatocellular carcinoma," Cancer Biol Ther., 2007, 6(12):1900-7.

Lee, "Efficient Synthesis of Cytotoxic Furonaphthoquinone Natural Products," Synthetic Communications, 2001, 31(3):381-386.

Leong et al., Targeted inhibition of Stat3 with a decoy oligonucleotide abrogates head and neck cancer cell growth Proc Natl Acad Sci USA, 2003, 100(7):4138-43.

Li et al., "Abstract LB-253: Inhibition of Stemness by BBI608 is Sufficient to Suppress Cancer Relapse and Metastasis", Cancer Research. AACR 106th Annual Meeting 2015, Apr. 18-22, 2015, Philadelphia, PA, published Aug. 1, 2015, 75(15 Supplement).

Li et al., "Autocrine-mediated activation of STAT3 correlates with cell proliferation in breast carcinoma lines," J. Biol. Chem. 2002, 277:17397-17405.

Li et al., "Inhibition of growth and metastasis of human hepatocellular carcinoma by antisense oligonucleotide targeting signal transducer and activator of transcription 3," Clin Cancer Res., 2006, 12(23):7140-8.

Li, "Identification of Pancreatic Cancer Stem Cells," Cancer Res, 2007, 67(3):1030-1037.

Li et al., "Suppression of cancer relapse and metastasis by inhibiting cancer stemness", Proceedings of the National Academy of Sciences, Jan. 20, 2015, 112(6):1839-1844.

Libby et al., "Inflammation and Atherosclerosis," Circulation, 2002, 105(9):1135-1143.

Lim, "Stat3 Contributes to Keloid Pathogenesis via Promoting Collagen Production, Cell Proliferation and Migration," Oncogene, 2006, 25(39):5416-5425.

Lin, L, et al., "STAT3 is Necessary for Proliferation and Survival in Colon Cancer-Initiating Cells", Cancer Res, 71(23):7226-7237.

Lin et al., "STAT signaling in the pathogenesis and treatment of leukemias," Onconogene, May 15, 2000, 19(21):2496-2504.

Lin et al., "Constitutive activation of JAK3/STAT3 in colon carcinoma tumors and cell lines: inhibition of JAK3/STAT3 signaling induces apoptosis and cell cycle arrest of colon carcinoma cells," Am J Pathol, 2005, 167:969-980.

Lin et al., "Significance of the expression of phosphorylated signal transducer and activator of transcription-3, -Akt, and -cyclin D1 in angiosarcoma," J. Derm. Sci., 2007, 48(1):64-66.

Lin et al., "Significance of the expression of phosphorylated-STAT3, -Akt, and -ERK1/2 in several tumors of the epidermis," J. Derm. Sci., 2007, 48(1):71-73.

Ling, "Mesenchymal Stem Cells Overexpressing IFN-Inhibit Breast Cancer Growth and Metastases through Stat3 Signaling in a Syngeneic Tumor Model," Cancer Microenviron, 2010, 3(1):83-95.

Lipinski, "Experimental and Computational Approaches to Estimate Solubility and Permeability in Drug Discovery and Development Settings," Adv. Drug Deliv. Rev., 2001, 46(1-3):3-26.

Liou et al., "Reactive oxygen species in cancer," Free Radic Res., May 2010, 44(5):479-496.

Liu et al., "Expression and clinical significance of COX-2, p-Stat3, and p-Stat5 in esophageal carcinoma," Ai Zheng, 2007, 26(5):458-62 [English Abstract].

Lopes, "Efficient Synthesis of Cytotoxic Quinones: 2-Acteyl-4H,9H-naphtho[2,3-b]furan-4, 9-Dione (6) and (:t)-2-(1-Hydroxyethyl)-4H,9H-naphtho[2,3-b]furan-4,9-Dione (7)," Journal of Heterocyclic Chemistry, 1984, 21:621-622.

Lovato, "Constitutive STAT3 Activation in Intestinal T Cells from Patients with Crohn's Disease," J Biol Chem, 2003, 278(19):16777-16781.

Ma et al., "Constitutive activation of Stat3 signaling pathway in human colorectal carcinoma," World J. Gastroent., 2004, 10(11):1569-1573.

Ma, "Identification and Characteristic of Tumorigenic Liver Cancer Stem/Progenitor Cells," Gastroenterology, 2007, 132(7):2542-2556.

Manolagas, "Role of Cytokines in Bone Resorption," Bone, 1995, 17(2 Suppl):63S-67S.

Masayuki et al., "Cytotoxic Activity toward KB Cells of 2-Substituted Naphtho[2,3-b]furan-4, 9-Diones and Their Related Compounds," Biosci. Biotechnol. Biochem., 2006, 70(4): 1009-1012.

Masuda et al., "Constitutive activation of signal transducers and activators of transcription 3 correlates with cyclin D1 overexpression and may provide a novel prognostic marker in head and neck squamous cell carcinoma," Cancer Res. (2002), 62(12):3351-5.

Maruyama, A., et al., "Electrophotographic Photoreceptor, Process Cartridge and Electrophotographic Apparatus Using Same", STN Database Accession No. 1999:157137 Chemical Abstracts Service, Columbus, OH XP002661425, (Mar. 10, 1999), 3 pgs.

Migone, T.-S., et al., "Constitutively Activated Jak-STAT Pathway in T Cells Transformed With HTLV-I", Science, Jul. 7, 1995, 269(5220):79-81.

Ministry of Health of the Russian Federation, "Guidelines: For the Experimental(Preclinical) Investigation of New Pharmaceutical Substances," Moscow, 2000, p. 111.

Mizoguchi et al., Journal of Neuropathology and Experimental Neurology, 2006, 65(12):1181-1188.

Mora et al., "Constitutive activation of Stat3 in human prostate tumors and cell lines: direct inhibition of Stat3 signaling induces apoptosis of prostate cancer cells," Cancer Res, 2002 62(22):6659-6666.

Morikawa et al., "STAT3 Expression, Molecular Features, Inflammation Patterns, and Prognosis in a Database of 724 Colorectal Cancers," Clinical Cancer Research, Mar. 15, 2011, 17(6):1452-1462.

Morrissette, "High-Throughput Crystallization: Polymorphs, Salts, Co-Crystals and Solvates of *Pharmaceutical Solids,*" *Adv. Drug Delivery Rev. 2004, 56:275-300.*

Muller et al., "Potential antipsoriatic agents: lapacho compounds as potent inhibitors of HaCaT cell growth," J. Nat. Prod., 1999, 62:1134-1136.

Nielsen et al., "Inhibition of constitutively activated Stat3 correlates with altered Bcl-2/Bax expression and induction of apoptosis in mycosis fungoides tumor cells," Leukemia, 1999, 13(5):735-738.

Ning et al., "Signal transducer and activator of transcription 3 activation is required for Asp(816) mutant c-Kit-mediated cytokine-independent survival and proliferation in human leukemia cells," Blood, 2001, 97:3559-3567.

Niu et al., "Gene therapy with dominant-negative Stat3 suppresses growth of the murine melanoma B16 tumor in vivo," Cancer Res., 1999, 15;59(20):5059-5063.

Niu et al., "Roles of activated Src and Stat3 signaling in melanoma tumor cell growth," Oncogene, 2002, 21(46):7001-7010.

Niu et al., "Constitutive Stat3 activity up-regulates VEGF expression and tumor angiogenesis,"Oncogene, 2002, 21(13):2000-2008.

No Author, "International Research Congress on Natural Product as Medicinal Agents", Strasbourg-France, Jul. 6-11, Planta Med, Jul. 1980, 39(3):194-196.

(56) References Cited

OTHER PUBLICATIONS

Oettle et al., "Paclitaxel as weekly second-line therapy in patients with advanced pancreatic carcinoma," Anticancer Drugs, 2000, 11(8):635-638.

Orshal and Khalil, "Interteukin-6 Impairs Endothelium-Dependent NO-cGMP-Mediated Relaxation and Enhances Contraction in Systemic Vessels of Pregnant Rats," Am J Physiol Regul Integr Comp Physiol, 2004, 286(6):1013-1023.

Paridaens et al., "Paclitaxel Versus Doxorubicin as First-Line Single-Agent Chemotherapy for Metastatic Breast Cancer: a European Organization for Research and Treatment of Cancer Randomized Study with Cross-Over," J. Clin. Oneal. Feb. 2000; 18(4):724-33.

Pedranzini et al., "Stat3 is required for the development of skin cancer," J. Clin. Invest., 2004, 114(5):619-622.

Perez-Sacau, et al., "Synthesis and Pharmacophore Modeling of Naphthoquinone Derivatives with Cytotoxic Activity in Human Promyelocytic Leukemia HL-60 Cell Line", J. Med. Chem., Feb. 2007, 50(4):696-706.

Peraza-Sanchez, "Cytotoxic Constituents of the Roots of Ekmanianthe Longiflora," American Chemical Society Publication—Journal of Natural Products, (2000), 63:492-495.

Pereira et al., "Invasion-Associated MMP-2 and MMP-9 are Up-Regulated Intracellularly in Concert with Apoptosis Linked to Melanoma Cell Detachment," Clinical and Experimental Metastasis, 2005, 22:285-295.

Pfitzner, et al., "The Role of STA Ts in Inflammation and Inflammatory Diseases", Curr Pharm Des, Sep. 2004, 10(23):2839-2850.

Pinzon-Guzman, "Protein kinase C regulates rod photoreceptor differentiation through modulation of STAT3 signalinq", Adv Exp Med Biol, 2010, 664:21-28.

Pillai et al., "Effects of transient overexpression or knockdown of cytochrome P450 reductase on reactive oxygen species generation and hypoxia reoxygenation injury in liver cells," Dept of Pharma Sci., Dec. 2011, 38(12):846-853.

Poli et al., "STAT3-mediated metabolic reprograming in cellular transformation and implications for drug resistance," Frontiers in Oncology, Jun. 8, 2015, 5(121):6 pages.

Ponti, "Isolation and in Vitro Propagation of Tumorigenic Breast Cancer Cells with Stem/Progenitor Cell Properties," Cancer Res, 2005, 65(13):5506-11.

Porter "New insights into the role of cytochrome P450 reductase (POR) in microsomal redox biology," Acta Pharmaceutical Sinica., 2012, 2(2):102-106.

Price, "Computational Methodologies: Toward Crystal Structure and Polymorph Prediction," Polymorphism in Pharmaceutical Solids, CRC Press, Boca Raton, FL, 2009, 2nd edition, 31 pages.

Prince, "Identification of a Subpopulation of Cells with Cancer Stem Cell Properties in Head and Neck Squamous Cell Carcinoma," Proc Natl Acad Sci USA, 2007, 104(3):973-978.

Punjabi et al., "Persistent activation of STAT3 by latent Kaposi's sarcoma-associated herpesvirus infection of endothelial cells", J Viral, (2007), 81(5):2449-2458.

U.S. Appl. No. 16/408,187, Li et al., filed May 9, 2019.
U.S. Appl. No. 16/445,416, Li et al., filed Jun. 19, 2019.
U.S. Appl. No. 16/463,162, Li et al., filed May 22, 2019.
U.S. Appl. No. 16/577,868, Li et al., filed Sep. 20, 2019.
U.S. Appl. No. 16/586,049, Li et al., filed Sep. 27, 2019.
U.S. Appl. No. 16/590,495, Li et al., filed Oct. 2, 2019.
U.S. Appl. No. 16/591,960, Li et al., filed Oct. 3, 2019.

Capsugel, "Technical Reference File: Hard Gelatin Capsules," 4th Edition, 57 pages 2014.

"Anonymous,""POR cytochrome p450 oxidoreductase [9Homo sapiens(human)]-Gene-NCBIOfficial Symbol Official Full Name," Jul. 1, 2019, retrieved on Aug. 21, 2019, retrieved from URL <URL:https://www.ncbi.nlm.nih.gov/gene?Db=gene&Cmd=DetailsSearch&Term=5447>, pp. 1-17.

Bannwitz et al., "Synthesis and structure-activity relationships of lapacho analogues. 2. Modification of the basic naphtho[2,3-b]furan-4,9-dione, redox activation, and suppression of human keratinocyte hyperproliferation by 8-hydroxynaphtho[2,3-b]thiophene-4,9-diones," J Med Chem., Jul. 24, 2014, 57(14):6226-6239.

Chang et al., "Evaluation of Tumor Cell-Tumor Microenvironment Component Interactions as Potential Predictors of Patient Response to Napabucasin," Mol Can Res., Jul. 1, 2019, 13(7):1429-1434.

Clinicaltrials.com, "A Study of BBI608 in Adult Patients with Advanced Colorectal Cancer," ID NCT01776307, [retrieved Aug. 22, 2019] retrieved from URL <https://clinicaltrials.gov/ct2/show/NCT01776307>, 10 pages.

Danishefsky et al., "Stereospecific total syntheses of dl-coriolin and dl-coriolin B," J of Am Chem Soc., 1981, 103(12):3460-3467.

Defant et al., "Regioselectivity in the Multi-Component Synthesis of Indolizinoquinoline-5,12-dione Derivatives," European Journal of Organic Chemistry, Sep. 2006, 18:4201-4210.

Furtek et al, "Strategies and Approaches of Targeting STAT3 for Cancer Treatment," ACS Chem. Biol., Jan. 5, 2016, 11(2):308-318.

Gowrishankar et al., "Inducible but Not Constitutive Expression of PD-L1 in Human Melanoma Cells is Dependent on Activation of NF-κB," PLOS One., Apr. 6, 2015, pp. 1-19.

International Search Report and Written Opinion in International Application No. PCT/US2008/075848, dated May 14, 2009, 8 pages.

International Search Report and Written Opinion in International Application No. PCT/US2008/075906, dated Dec. 8, 2008, 10 pages.

International Search Report and Written Opinion in International Application No. PCT/US2016/028179, dated Oct. 20, 2016, 11 pages.

International Search report and Written Opinion in International Application No. PCT/US2017/014163, dated Jul. 10, 2017, 13 pages.

International Search Report and Written Opinion in International Application No. PCT/US2008/075903, dated Feb. 24, 2009, 12 pages.

International Search Report and Written Opinion in International Application No. PCT/US2011/029281, dated Aug. 12, 2011, 10 pages.

International Search Report and Written Opinion in International Application No. PCT/US2011/029283, dated May 17, 2011, 8 pages.

International Search Report and Written Opinion in International Application No. PCT/US2014/033566, dated Dec. 16, 2014, 18 pages.

International Search Report and Written Opinion in International Application No. PCT/US2016/028177, dated Jul. 20, 2016, 10 pages.

International Search Report and Written Opinion in International Application No. PCT/US2016/028178, dated Aug. 9, 2016, 12 page.

International Search Report and Written Opinion in International Application No. PCT/US2018/032937, dated Aug. 24, 2018, 11 pages.

International Search Report and Written Opinion in International Application No. PCT/US2017/063734, dated Jan. 25, 2018, 13 pages.

International Search Report and Written Opinion in International Application No. PCT/IB2017/001573, dated May 16, 2018, 16 pages.

International Search Report and Written Opinion in International Application No. PCT/US2018/023827, dated Aug. 20, 2018, 20 pages.

International Search Report and Written Opinion in International Application No. PCT/US2019/034658, dated Sep. 10, 2019, 15 pages.

International Preliminary Report on Patentability in International Application No. PCT/US2008/075906, dated Mar. 16, 2010, 10 pages.

International Preliminary Report on Patentability in International Application No. PCT/US2016/028179, dated Oct. 17, 2017, 8 pages.

International Preliminary Report on Patentability in International Application No. PCT/US2017/014163, dated Jul. 24, 2018, 8 pages.

(56) References Cited

OTHER PUBLICATIONS

International Preliminary Report on Patentability in International Application No. PCT/US2008/075903, dated Mar. 16, 2010, 11 pages.
International Preliminary Report on Patentability in International Application No. PCT/US2011/029281, dated Sep. 25, 2012, 7 pages.
International Preliminary Report on Patentability in International Application No. PCT/US2011/029283, dated Sep. 25, 2012, 6 pages.
International Preliminary Report on Patentability in International Application No. PCT/US2014/033566, dated Oct. 13, 2015, 13 pages.
International Preliminary Report on Patentability in International Application No. PCT/US2016/028177, dated Oct. 17, 2017, 7 pages.
International Preliminary Report on Patentability in International Application No. PCT/US2016/028178, dated Oct. 17, 2017, 8 pages.
International Preliminary Report on Patentability in International Application No. PCT/US2017/063734, dated Jun. 4, 2019, 8 pages.
International Preliminary Report on Patentability in International Application No. PCT/IB2017/001573, dated May 28, 2019, 10 pages.
International Preliminary Report on Patentability in International Application No. PCT/US2008/075848, dated Mar. 16, 2010, 6 pages.
Invitation to Pay Additional Fees and, Where Applicable, Protest Fee in International Application No. PCT/IB2017/001573, Mar. 13, 2018, 15 pages.
Invitation to Pay Additional Fees and, Where Applicable, Protest Fee in International Application No. PCT/US2018/023827, dated Jun. 18, 2018, 15 pages.
Inagaki et al., "Synthesis and Cytotoxicity on Human Leukemia Cells of Furonaphthoquinones Isolated from *Tabebuia* Plants," Chemical and Pharmaceutical Bulletin, 61(6):670-673.
Ji et al., "Clinicopathological implications of NQ01 overexpression in the prognosis of pancreatic adenocarcinoma," Oncol Lett., Mar. 7, 2017, 13(5):2996-3002.
Kamel-Reid et al, "Engraftment of immune-deficient mice with human hematopoietic stem cells," Science, Dec. 23, 1988, 242:1706-1709.
Kim et al, "A specific STAT3-binding peptide exerts antiproliferative effects and antitumor activity by inhibiting STAT3 phosphorylation and signaling," Cancer Res., Apr. 15, 2014, 74(8):2144-2151.
Laatsch et al., "Synthese von Maritinon und anderen 8,8'-Bijuglonen," Liebigs Annalen der Chemie, 1985, 12:2420-2442 English Abstract.
Larochelle et al, "Identification of primitive human hematopoietic cells capable of repopulating NOD/SCID mouse bone marrow: implications for gene therapy," Nat. Med., Dec. 1996, 2:1329-1337.
Le et al, "PD-1 Blockade in Tumors with Mismatch-Repair Deficiency," N. Engl. J. Med., Jun. 25, 2015, 372:2509-2520.
Li et al., "Feedback activation of STAT3 mediates trastuzumab resistance via upregulation of MUC1 and MUC4 expression," OncoTarget, Jun. 26, 2014, 5(18):8317-8329.
Liu et al., "Enantio- and Diastereoselective Intermolecular Stetter Reaction of Glyoxamide and Alkylidene Ketoamides," Organic Letters., 2009, 11(13):2856-2859.
Lobo et al., "The biology of cancer stem cells," Annu Rev Cel Cev Biol., 2007, 23:675-699.
Lopes et al., "Synthesis of Dimethoxyfuranonaftoquinones," Synthetic Communications, Oct. 1, 1988, 18(14):1731-1742.
McCune et al, "The SCID-hu mouse: murine model for the analysis of human hematolymphoid differentiation and function," Science, Sep. 23, 1988, 241:1632-1639.
Matsumoto et al., "Individual Formulations Nature and Preparation Method," Medicine Manual, Mar. 20, 1989, 1st Edition:80, translation 5 pages.
Naciuk et al., "Exploitation of a tuned oxidation with N-haloimides in the synthesis of caulibugulones A-D," J Org Chem., May 17, 2013, 78(10):5026-5030.
Nishi et al., "Retrospective analysis of the international standard-dose FOLFIRI (plus bevacizumab) regimen in Japanese patients with unresectable advanced or recurrent colorectal carcinoma," International Journal of Clinical Oncology, Oct. 2011, 16(5):488-493.
Oh et al., "Implications of NQ01 in cancer therapy," BMB Reports, Nov. 30, 2015, 48(11):609-617.
Ohta, "Regiospecific Synthesis of 2-Substituted Furanonaphthoquinones," Journal of Heterocyclic Chemistry, Jul. 1, 2000, 37:731-734.
Okano, "Introduction to Modern Pharmaceuticals," 1987, revised 3rd edition:111, translation 4 pages.
Patil Sharad et al., "NIR-emitting quinone-fused coumarin dyes: aqueous mediated, catalyst free sythesis and their optical properties," Tetrahedron Letters, Elsevier, Jun. 20, 2016, 57(29):3100-3104.
Penning et al., "Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benze nesulfonamide (SC-58635, celecoxib)," J Med Chem., Apr. 25, 1997, 40(9):1347-1365.
Puthier et al., "IL-6 Up-Regulates MCL-1IN Human Myeloma Cells through JAK/STAT rather than ras/MAP Kinase Pathway," Eur J lmmunol, 1999, 29(12):3945-3950.
Qui et al., "RNA interference-mediated signal transducers and activators of transcription 3 gene silencing inhibits invasion and metastasis of human pancreatic cancer cells," Cancer Sci. 2007, 98(7):1099-1106.
Qiuwen et al, "Evaluation of the Potential Cancer Chemotherapeutic Efficacy of Natural Product Isolates Employing in Vivo Hallow Fiber Tests," J. Nat. Prod. 2002, 65(6):842-850.
Rahaman et al., "Inhibition of constitutively active Stat3 suppresses proliferation and induces apoptosis in glioblastoma multiforme cells," Oncogene, 2002, 21(55):8404-8413.
Rao and Kingston, "Plant Anticancer Agents. XII. Isolation and Structure Elucidation of New Cytotoxic Quinones from Tabebuia Cassinoides," Journal of Natural Products, 1982, 45(5):600-604.
Rawat et al., "Constitutive activation of STAT3 is associated with the acquisition of an interleukin 6-independent phenotype by murine plasmacytomas and hybridomas," Blood, 2000, 96(10):3514-3521.
Reagan-Shaw, "Dose Translation from Animal to Human Studies Revisited," The FASEB Journal, 2007, 22(3):659-661.
Ricci-Vitiani, "Identification and Expansion of Human Colon-Cancer-Initiating Cells," Nature. 2007, 445(7123):111-115.
Rieber et al., "Relationship of Mc1-1 isoforms, ratio p21WAF1/cyclin A, and Junkinase phosphorylation to apoptosis in human breast carcinomas", Biochemical and Biophysical Research Communications , 2002, 297:943-949.
Rieber et al., "Mc1-1 cleavage and sustained phosphorylation of c-Jun-N-terminal kinase mediate melanoma apoptosis induced by 2-acetyl furanonaphthoquinone," Cancer Biology and Therapy, 2008, 7(8):1206-1211.
Ried et al., "State of the art: diagnostic tools and innovative therapies for treatment of advanced thymoma and thymic carcinoma," Eur J Cardiothorac Surg., Jun. 2016, 49(6): 1545-1552.
Rouhi, "The Right Stuff," Chemical & Engineering News, 81(8):32-35.
Roder, "STAT3 is Constitutively Active in Some Patients with Polycythemia Rubra Vera," Exp Hematol, 2001, 29(6):694-702.
Romano et al, "The therapeutic promise of disrupting the PD-1/PD-L1 immune checkpoint in cancer: unleashing the CD8 T cell mediated anti-tumor activity results in significant, unprecedented clinical efficacy in various solid tumors," J Immunother Cancer., Apr. 21, 2015, 3:15, 5 pages.
Rosen et al., "The role of constitutively active signal transducer and activator of transcription 3 in ovarian tumorigenesis and prognosis," Cancer, 2006, 107(11):2730-2740.
Rowland et al., "Clinical Pharmacokinetics: Concepts and Applications," Lippincott Williams & Wilkins, 1995, 4th edition, Front Matter.

(56) References Cited

OTHER PUBLICATIONS

Ryu et al., "Synthesis and antifungal activity of furo[2,3-f]quinolin-5-ols," Bioorg Med Chem Lett., Feb. 1, 2011, 21(3):952.
Sano et al., "STAT3 Links Activated Keratinocytes and lmmunocytes Required for Development of Psoriasis in a Novel Transgenic Mouse Model", Nat Med, 2005, 11(1):43-49.
Savarese et al., "Coexpression of oncostatin M and its receptors and evidence for STAT3 activation in human ovarian carcinomas," Cytokine, 2002, 17(6):324-334.
Schaefer et al., "Constitutive activation of Stat3alpha in brain tumors: localization to tumor endothelial cells and activation by the endothelial tyrosine kinase receptor (VEGFR-2)," Oncogene, 2002, 21(13):2058-2065.
Schatton, "Identification of Cells Initiating Human Melanomas," Nature. 2008, 451(7176):345-349.
Scheper, "Sulindac induces apoptosis and inhibits tumor growth in vivo in head and neck squamous cell carcinoma", Neoplasia, 2007, 9(3):192-199.
Schlette, "Survivin Expression Predicts Poorer Prognosis in Anaplastic Large-Cell Lymphoma," J Clin Oncol, 2004, 22(9):1682-1688.
Scholz et al., "Activated signal transducer and activator of transcription 3 (STAT3) supports the malignant phenotype of human pancreatic cancer", Gastroenterolgy, 2003, 125:891-905.
Schumacher et al., "Reactive Oxygen Species in Cancer: A Dance with the Devil," Cell Press Canc Cell., Feb. 9, 2015, 27(2):156-157.
Sengupta, "Activation of Monocycle Effector Genes and STAT Family Transcription Factors by Inflammatory Synovial Fluid is Independent of Interferon Gamma," J Exp Med, 1995, 181(3):1015-1025.
Shaikh et al., "Streptonigrin. 1. Structure-activity relationships among simple bicyclic analogues. Rate dependence of DNA degradation on quinone reduction potential," J Med Chem., 1986, 29(8):1329-1340.
Shouda, "Induction of the Cytokine Signal Regulator SOCS3/CIS3 as a Therapeutic Strategy for Treating Inflammatory Arthritis," J Clin Invest, 108(12):1781-1788.
Siegel et al.,"NAD(P)H: Quinone Oxidoreductase 1 (NQO1) in the Sensitivity and Resistance to Antitumor Quinones," Biochem Pharmacol., Apr. 15, 2012, 83(8):1033-1040.
Silver et al., "Activated signal transducer and activator of transcription (STAT) 3: localization in focal adhesions and function in ovarian cancer cell motility," Cancer Res. 2004, 64(10):3550-3558.
Simamura et al., "Furanonaphthoquinones Cause Apoptosis of Cancer Cells by Inducing the Production of Reactive Oxygen Species by the Mitochondrial Voltage-Dependent Anion Channel", Cancer Biology & Therapy, Nov. 2006, 5(11):1523-1529.
Simeone-Penney, "Airway Epithelial STAT3 Is Required for Allergic Inflammation in a Murine Model of Asthma," J Immunol, 178(10):6191-6199.
Singh, "Identification of a Cancer Stem Cell in Human Brain Tumors," Cancer Res, 2003, 63(18):5821-5828.
Solorzano et al., "Decreased Glycolytic Metabolism Accelerates Apoptosis in Response to 2-Acetyl Furanonaphthoquinone in K1735 Melanoma Irrespective of BCL-2 Overexpression," Cancer Biol. Ther., Mar. 2005, 4(3):329-335.
Sommer et al., "In vivo activation of STAT3 in cutaneous T-cell lymphoma. Evidence for an antiapoptotic function of STAT3," Leukemia, 2004, 18(7):1288-1295.
Song and Grandis, "STAT Signaling in Head and Neck Cancer," Onogene, 2000, 19(21):2489-2495.
Song et al., "Activation of Stat3 by receptor tyrosine kinases and cytokines regulates survival in human non-small cell carcinoma cells," Oncogene, 2003, 22(27):4150-4165.
Song, "A Low-Molecular-Weight Compound Discovered Through Virtual Database Screening Inhibits Stat3 Function in Breast Cancer Cells," Proc. Natl. Acad Sci. 102(13):4700-4705.
Spiekermann et al., "Constitutive activation of STAT transcription factors in acute myelogenous leukemia," Eur J Haematol, 2001, 67(2):63-71.
Srijiwangsa et al. "Roles of NAD (P) H-Guinone Oxidoreductase 1 (NQO1) on Cancer Progression and Chemoresistance," Journal of Clinical & Experimental Oncology, 2017, 6(4):6 pages.
Steinert, "HPLC Separation and Determination of Naphtho[2,3-b]furan-4,9-Diones and Related Compounds in Extracts of Tabebuia Avellanedae (Bignoniaceae)," J Chromato, 1995, 693:281-287.
Stelmasiak, "lnterleukin-6 Concentration in Serum and Cerebrospinal Fluid in Multiple Sclerosis Patients," Med Sci Monit, 2000, 6(6):1104-1108.
Stephens, "A Common Functional Variant in the lnterleukin-6 gene is Associated with Increased Body Mass lndex in Subjects with Type 2 Diabetes Mellitus," Mol Genet Metab, 2004, 82(2):180-186.
STN Accession No. 1985-141337 CN (141337-87-3 Registry), (May 15, 1992), 1 pg.
STN Accession No. 1986 568912.
STN Accession No. 1987-141337 CN: (141337-85-1 Registry), (May 15, 1992), 1 pg.
STN Accession No. 1989-141337 CN: (141337-89-5 Registry), (May 15, 1992), 1 pg.
STN Accession No. 1990-141337 CN: (141337-90-8 Registry),(May 15, 1992), 1 pg.
STN Accession No. 1992:245248.
STN Accession No. 1997-141337 CN: (141337-97-5 Registry), (May 15, 1992), 1 pg.
STN Accession No. 2002:33229.
STN Accession No. 2002:080446, CN: (80446-02-2 Registry), (Nov. 16, 1984), 1 oa.
STN Accession No. 33-221190,CN: (221190-33-6 Registry), (Apr. 14, 1999), 1 pg.
STN Accession No. 32-221190, CN: (221190-32-5 Registry), (Apr. 14, 1999), 1 pg.
STN Accession No. 31-221190, CN: (221190-31-4 Registry), (Apr. 14, 1999),1 pg.
Stout, "No Cancer", [Online] retrieved from the internet:<http://nocancer.blogspot.com/2005/05/14-paudarco.html>, (2005).
Sun et al., "Comparison of Effects of the Tyrosine Kinase Inhibitors AG957, AG490, and ST1571 on BCR- ASL-Expressing Cells, Demonstrating Synergy Between AG490 and ST1571," Blood, 2001, 97(7):2008-2015.
Szotek, "Ovarian Cancer Side Population Defines Cells with Stem Cell-Like Characteristics and Mullerian Inhibiting Substance Responsiveness," Proc Natl Acad Sci USA, 2006, 103(30):11154-11159.
Takano, et al., "Tumor-specific cytotoxicity and type of cell death induced by naphtho[2,3-b]furan-4,9-diones and related compounds in human tumor cell lines: relationship to electronic structure", Anticancer Research, 2009, 29:455-464.
Taylor, "Technical Data Report for Pau D'Arco," Herbal Secrets of the Rainforest, $2^{nd}$ Edition, 2003.
Tefferi, "Classification, Diagnosis and Management of Myeloproliferative Disorders in the JAK2V617F era," Hamtology Am Soc Hematol Educ Program, 2006, 240-245.
Toyonaga et al., "Blockade of constitutively activated Janus kinase/signal transducer and activator of transcription-3 pathway inhibits growth of human pancreatic cancer," Cancer Lett. 2003, 201(1):107-116.
Trovato et al., "Distinctive expression of STAT3 in papillary thyroid carcinomas and a subset of follicular adenomas," Histol Histopathol., 2003, 18: 393-399.
Tsareva et al., "Signal transducer and activator of transcription 3 activation promotes invasive growth of colon carcinomas through matrix metalloproteinase induction," Neoplasia, 2007, 4:279-291.
Tsutsumi et al., "Phase II Trial of Chemotherapy plus Bevacizumab as Second-Line Therapy for Patients with Metastatic Colorectal Cancer That Progressed on Bevacizumab with Chemotherapy: The Gunma Clinical Oncology Group (GCOG) trial 001 SILK Study," Oncology, Aug. 2012, 83(3):151-157.
Wang et al., "Effect of STAT3 siRNA-induced inhibition of STAT3 gene expression on the growth and apoptosis of lewis lung cancer cells", J. Clin. Oneal. 2006, 3(6):392-399.
Wang et al., "Small interfering RNA suppression of transducer and activator of transcription 3 (STAT3) signaling pathway: inhibitory

(56) References Cited

OTHER PUBLICATIONS effect on proliferation of human esophageal squamous carcinoma cells," Chinese Journal of Pathology, 2007, 36(6):379-383 [English Abstract].

Wang, "Identification of Cancer Stem Cell-Like Side Population Cells in Human Nasopharyngeal Carcinoma Cell Line," Cancer Res, 2007, 67(8):3716-3724.

Wang, "A Small Amphipathic a-Helical Region is Required for Transcriptional Activities and Proteasome-Dependent Turnover of the Tyrosine-Phosphorylated STATS", EMBO J, 2000, 19(3):392-399.

Wang et al., "Regulation of the Innate and Adaprive Immune Responses by STAT3 Signaling Tumor Cells", Nat Med, 2004, 10(1):48-54.

Watson & Miller, "Elevated levels of members of the STAT family of transcription factors in breast carcinoma nuclear extracts," British Journal of Cancer, 1995, 71(4):840-844.

Weber-Nordt, "Constitutive Activation of STAT Proteins in Primary Lymphoid and Myeloid Leukemia Cells and in Epstein-Barr Virus (EBV)-Related Lymphoma Cell Lines," Blood, 1996, 88(3):809-816.

Wei et al., "Stat3 activation regulates the expression of vascular endothelial growth factor and human pancreatic cancer angiogenesis and metastasis," Oncogene, 2003, 22(3):319-329.

Wermuth, "Molecular Variations Based on Isoteric Replacements," The Practice of Medicinal Chemistry, Academic Press, 1996. pp. 203-237.

Williams, "Two New Cytotoxic Naphthoquinones from Mendoncia Cowanii from the Rainforest of Madagascar," Planta Med., May 2006, 72(6):564-6.

Wyss-Coray, "Inflammation in Alzheimer disease: driving force, bystander or beneficial response?," Nat Med., Sep. 2006, 12(9):1005-1015.

Xie et al., "Activation of stat3 in human melanoma promotes brain metastasis," Cancer Res., 2006, 66(6):3188-3196.

Xie, "STAT3 Activation Regulates the Expression of Matrix Metalloproteinase-2 and Tumor Invasion and Metastasis," Oncogene, 2004, 23(20):3550-3560.

Yakata et al., "Expression of p-STAT3 in human gastric carcinoma: significant correlation in tumour invasion and prognosis," Int J Oncol., 2007, 30(2):437-442.

Yafee, K, "Inflammatory Markers and Cognition in Well-Functioning African American and White Elders", Neurology, 61(1):76-80.

Yamashita et al., "Synthesis and evaluation of bioactive naphthoquinones from the Brazilian medical plant, *Tabebuia avellanedae*," Bioorganic & Medicinal Chemistry, 2009, 17(17):6286-6291.

Yao et al., "Experimental Study on the Growth Inhibition of Bladder Cancer Cells by Signal Conduction Blocker AG490," J. Clin. Ural., 2006, 21(5):379-382. (English Abstract).

Yardley., "nab-Paclitaxel mechanisms of action and delivery," J Control Release., Sep. 28, 2013, 170(3):365-372.

Yau et al., "Inhibition of Integrin-Linked Kinase by QLT0254 Inhibits Akt-Dependent Pathways and is Growth Inhibitory in Orthotopic Primary Pancreatic Cancer Xenografls," Cancer Res., 2005, 65(4):1497-1504.

Yong Rok Lee, et al., "Ceric Ammonium Nitrate (CAN)-Mediated Oxidative Cycloaddition of 1,3-Dicarbonyls to Conjugated Compounds. Efficient Synthesis of Dihydrofurans, Dihydrofurocoumarins, Dihydrofuroquinolinones, Dihydrofurophenalenones, and Furonaphthoquinone Natural Products", Tetrahedron, 2000, 56(45):8845-8853.

Yoshida et al., "Discovery and preclinical profile of teneligliptin (3-[(2S,4S)-4-[4-(3- methyl-1-phenyl-1H-pyrazol-5-yl)piperazin-1-yl]pyrrolidin-2-ylcarbonyl]thiazolidine): a highly potent, selective, long-lasting and orally active dipeptidyl peptidase IV inhibitor for the treatment of type 2 diabetes," Bioorg Med Chem., Oct. 1, 2012, 20(19):5705-5719.

Yue et al., "Synthesis and evaluation of indenopyrazoles as cyclin-dependent kinase inhibitors. 3. Structure activity relationships at C3(1,2)," J Med Chem., Nov. 21, 2002, 45(24):5233-5248.

Yu, H, "STAT3: Linking Oncogenesis with Tumor Immune Evasion," AACR Annual Meeting, San Diego, CA, Cancer Res (Abstract SY03-03), 68(9 Supp):1-3.

Yu, H., "The STATs of cancer—new molecular targets come of age," R., Nat Rev Cancer, 2004, 4(2):97-105.

Zani, "Furanonaphthoquinones from Tabebuia Ochracea," Phytochemistry, 1991, 30(7):2379-2381.

Zhang, "Intratumoral Delivery and Suppression of Prostate Tumor Growth by Attenuated *Salmonella enterica* Serovar Typhimurium Carrying Plasmid-Based Small Interfering RNAs," Cancer Res, 2007, 67(12):5859-5864.

Zhou et al., "Activation of the PTEN/mTOR/STAT3 Pathway in Breast Cancer Stem-Like Cells is Required for Viability and Maintenance," PNAS., 104(41):16158-16163.

Zhou et al., "Corrections: Activation of the PTEN/mTOR/STAT3 Pathway in Breast Cancer Stem-Like Cells is Required for Viability and Maintenance," PNAS., 2007, 104(49): 19655-19656.

"European Application Serial No. 14723257.3, Communication pursuant to Article 94(3) EPC dated Apr. 4, 2017", 11 pgs.

"European Application Serial No. 14723257.3, Response filed May 27, 2016 to Communication pursuant to Rules 161(1) and 162 EPC dated Nov. 17, 2015", 7 pgs.

\* cited by examiner

2-ACETYLNAPHTHO[2,3-B]FURAN -4,9-DIONE FOR USE ON TREATING CANCER

CROSS-REFERENCE TO RELATED APPLICATIONS

This application is a continuation of U.S. application Ser. No. 16/220,636, filed on Dec. 14, 2018, which is a continuation of U.S. application Ser. No. 14/783,184, filed on Oct. 8, 2015, which is a U.S. National Stage Filing under 35 U.S.C. § 371 from International Application No. PCT/US2014/033566, filed on Apr. 9, 2014, and published as WO 2014/169078 on Oct. 16, 2014, which claims the benefit of U.S. Provisional Application No. 61/810,117, filed Apr. 9, 2013; U.S. Provisional Application No. 61/830,068, filed Jun. 1, 2013; U.S. Provisional Application No. 61/932,179, filed Jan. 27, 2014; and U.S. Provisional Application No. 61/938,386, filed Feb. 11, 2014. The contents of each of the above applications are hereby incorporated by reference in their entireties.

FIELD OF THE INVENTION

The invention provides naphthofuran compounds, polymorphs of naphthofuran compounds, naphthofuran compounds in particle form, purified compositions that contain one or more naphthofuran compounds, purified compositions that contain one or more naphthofuran compounds in particle form, and methods of using these naphthofuran compounds, polymorphs, purified compositions and/or particle forms to treat subjects in need thereof.

BACKGROUND OF THE INVENTION

Cancer fatalities in the United States alone number in the hundreds of thousands each year. Despite advances in the treatment of certain forms of cancer through surgery, radiotherapy, and chemotherapy, many types of cancer are essentially incurable. Even when an effective treatment is available for a particular cancer, the side effects of such treatment can be severe and result in a significant decrease in quality of life.

Most conventional chemotherapy agents have toxicity and limited efficacy, particularly for patients with advanced solid tumors. Chemotherapeutic agents cause damage to non-cancerous as well as cancerous cells. The therapeutic index of such compounds (a measure of the ability of the therapy to discriminate between cancerous and normal cells) can be quite low. Frequently, a dose of a chemotherapy drug that is effective to kill cancer cells will also kill normal cells, especially those normal cells (such as epithelial cells) which undergo frequent cell division. When normal cells are affected by the therapy, side effects such as hair loss, suppression of hematopoiesis, and nausea can occur. Depending on the general health of a patient, such side effects can preclude the administration of chemotherapy, or, at least, be extremely unpleasant and uncomfortable for the patient and severely decrease quality of the remaining life of cancer patients. Even for cancer patients who respond to chemotherapy with tumor regression, such tumor response often is not accompanied by prolongation of progression-free survival (PFS) or prolongation of overall survival (OS). As a matter of fact, cancer often quickly progress and form more metastasis after initial response to chemotherapy. Such recurrent cancers become highly resistant or refractory to chemotherapeutics. Such rapid recurrence and refractoriness, after chemotherapy, are considered to be caused by cancer stem cells.

Recent studies have uncovered the presence of cancer stem cells (CSC, also called tumor initiating cells or cancer stem-like cells) which have self-renewal capability and are considered to be fundamentally responsible for malignant growth, relapse and metastasis. Importantly, CSCs are inherently resistant to conventional therapies. Therefore, a targeted agent with activity against cancer stem cells holds a great promise for cancer patients (J Clin Oncol. 2008 Jun. 10; 26(17)). Therefore, while conventional chemotherapies can kill the bulk of cancer cells, they leave behind cancer stem cells. Cancer stem cells can grow faster after reduction of non-stem regular cancer cells by chemotherapy, which is considered to be the mechanism for quick relapse after chemotherapies.

Accordingly, there exists a need for discovering compounds and pharmaceutical compositions for selectively targeting cancer cells, for targeting cancer stem cells, and methods of preparing these compounds, pharmaceutical compositions for clinical applications, and methods of administering the same to those in need thereof.

The references cited herein are not admitted to be prior art to the claimed invention.

SUMMARY

In co-owned PCT applications published as WO 2009/036099, WO 2009/036101, and WO 2011/116399, all of which the entire contents are incorporated herein by reference, disclosure has been made of novel naphthofuran compounds, polymorphs of naphthofuran compounds, purified compositions that contain one or more naphthofuran compounds, and naphthofuran compounds in particle form. These naphthofuran compounds (including those in particle form), polymorphs, and purified compositions are selective inhibitors of cancer stem cells and STAT3. WO 2009/036099 and WO 2009/036101 disclose that the naphthofuran compounds target cancer stem cells. They also inhibit non-stem cancer cells through inhibiting STAT3. Those compounds are capable of killing many different types of cancer cells, without causing damage to normal cells under certain exposure conditions. The compounds can therefore be used for cancer treatment, especially for the treatment and prevention of refractory, recurrent, metastatic cancers, or STAT3-expressing cancers. The publications also describe the processes for preparing naphthofuran compounds, derivatives, and intermediates thereof, and the pharmaceutical composition of relevant compounds.

The present invention provides new methods of formulating and using these naphthofuran compounds (including those in particle form), polymorphs, and purified compositions in a variety of indications, including, for example, treating, delaying the progression of, preventing a relapse of, or alleviating a symptom of a cell proliferation disorder. For example, the naphthofuran compounds (including those in particle form), polymorphs, and purified compositions are useful in treating, delaying the progression of, preventing a relapse of, alleviating a symptom of, or otherwise ameliorating a cancer. In some embodiments, the cancer is selected from the group consisting of esophageal cancer, gastroesophageal junction cancer, gastroesophageal adenocarcinoma, colorectal cancer, colon adenocarcinoma, rectal adenocarcinoma, colorectal adenocarcinoma, breast cancer, ovarian cancer, head and neck cancer, melanoma, chondrosarcoma, gastric adenocarcinoma, and adrenocorticoid. In some embodiments, the cancer is esophageal cancer. In some embodiments, the cancer is gastroesophageal junction cancer. In some embodiments, the cancer is gastroesophageal adenocarcinoma. In some embodiments, the cancer is refractory. In some embodiments, the cancer is recurrent. In some embodiments, the cancer is metastatic. In some embodiments, the cancer is associated with overexpression of STAT3.

A method according to the invention of treating, delaying the progression of, preventing a relapse of, inhibiting the recurrence of, the metastasis of, alleviating a symptom of, and/or otherwise ameliorating a cancer (or neoplasm) in a human, mammal, or animal subject can include administering a therapeutically effective amount of the compound, product and/or pharmaceutical composition, so that anti-neoplastic activity occurs. For example, the anti-neoplastic activity can be anticancer activity. For example, the anti-neoplastic activity can include slowing the volume growth of the neoplasm, stopping the volume growth of the neoplasm, or decreasing the volume of the neoplasm. The neoplasm can include a solid tumor, a malignancy, a metastatic cell, a cancer stem cell. The neoplasm can include a carcinoma, a sarcoma, an adenocarcinoma, a lymphoma, or a hematological malignancy. The neoplasm can be refractory to treatment by chemotherapy, radiotherapy, and/or hormone therapy. The compound, product and/or pharmaceutical composition can be administered to prevent relapse of the neoplasm. The compound, product and/or pharmaceutical composition can be administered as an adjuvant therapy to surgical resection. The compound, product and/or pharmaceutical composition can be administered, for example, orally and/or intravenously. In some embodiments, the pharmaceutical composition comprises a Compound of the Invention in conjunction with at least the following: (i) a surfactant comprising sodium lauryl sulfate (SLS) or sodium dodecyl sulfate (SDS); (ii) Gelucire (lauroyl polyoxylglycerides); and Labrafil (linoleoyl polyoxylglycerides).

In this specification, the term "treating a cancer" may include delaying the progression of, preventing a relapse of, inhibiting the recurrent of, the metastatic of, alleviating a symptom of, and/or otherwise ameliorating a cancer (or neoplasm).

In some embodiments, the pharmaceutical composition comprises a Compound of the Invention in conjunction with at least the following: (i) a surfactant comprising sodium lauryl sulfate (SLS) or sodium dodecyl sulfate (SDS); (ii) Gelucire (lauroyl polyoxylglycerides); and (iii) Labrafil (linoleoyl polyoxylglycerides).

In some embodiments, the pharmaceutical composition includes, by weight, about 27.18% in the active ingredient, about 0.27% in the surfactant, about 14.51% in Gelucire, and about 58.04% in Labrafil. In some embodiments, the pharmaceutical composition includes about 125 mg of the active ingredient, about 1.2 mg of the surfactant, about 66.8 mg of Gelucire, and about 267 mg of Labrafil. In some embodiments, the pharmaceutical composition includes about 80 mg of the active ingredient, about 0.8 mg of the surfactant, about 42.7 mg of Gelucire, and about 170.9 mg of Labrafil. In some embodiments, the pharmaceutical composition is housed in a capsule. In some embodiments, the capsule is of size 1 or smaller.

A method according to the invention also includes treating, delaying the progression of, preventing a relapse of, alleviating a symptom of, or otherwise ameliorating a disease or disorder in a human, mammal, or animal subject afflicted with that disease or disorder. In some embodiments, the disease or disorder is any of the cancers (or neoplasms) described herein. In some embodiments, the cancer is selected from the group consisting of esophageal cancer, gastroesophageal junction cancer, gastroesophageal adenocarcinoma, colorectal cancer, colon adenocarcinoma, rectal adenocarcinoma, colorectal adenocarcinoma, breast cancer, ovarian cancer, head and neck cancer, melanoma, chondrosarcoma, gastric adenocarcinoma, and adrenocorticoid.

In some embodiments, the methods also include the step of detecting a level of phosphorylated STAT3 (p-STAT3) in a patient tissue, where the level of p-STAT3 is used as a biomarker for patient selection. In some embodiments, a tissue phosphorylated STAT3 level is above a benchmark level (more than 10% tumor cells with medium level of p-STAT3). In some embodiments, the cancer is associated with β-catenin localization in cell nucleus as opposed to in cell membrane. In some embodiments, the method includes the step of detecting a locus of β-catenin expression in a patient's tissue, where the locus of such β-catenin expression is used as a biomarker for patient selection. In some embodiments, significant β-catenin expression is detected in cell nucleus. In some embodiments, the medium to strong expression of β-catenin is detected in 20% or more tumor cells.

Administration of the compounds, products and/or pharmaceutical compositions to a patient suffering from a disease or disorder is considered successful if any of a variety of laboratory or clinical results is achieved. For example, administration is considered successful one or more of the symptoms associated with the disease or disorder is alleviated, reduced, inhibited or does not progress to a further, i.e., worse, state. Administration is considered successful if the disorder, e.g., a cancer or neoplasm, enters remission or does not progress to a further, i.e., worse, state.

In some embodiments, the compounds, products and/or pharmaceutical compositions described herein are administered in combination with any of a variety of known therapeutics, including for example, chemotherapeutic and other anti-neoplastic agents, anti-inflammatory compounds and/or immunosuppressive compounds. In some embodiments, the compounds, products and/or pharmaceutical compositions described herein are useful in conjunction with any of a variety of known treatments including, by way of non-limiting example, surgical treatments and methods, radiation therapy, chemotherapy and/or hormone or other endocrine-related treatment.

These "co-therapies" can be administered sequentially or concurrently. The compounds, products and/or pharmaceutical compositions described herein and the second therapy can be administered to a subject, preferably a human subject, in the same pharmaceutical composition. Alternatively, the compounds, products and/or pharmaceutical compositions described herein and the second therapy can be administered concurrently, separately or sequentially to a subject in separate pharmaceutical compositions. The compounds, products and/or pharmaceutical compositions described herein and the second therapy may be administered to a subject by the same or different routes of administration. The compounds, products and/or pharmaceutical compositions described herein may be administered to a subject firstly, and then the second therapy may be administered to a subject. The second therapy may be administered to a subject firstly, and then the compounds, products and/or pharmaceutical compositions described herein may be administered to a subject. In some embodiments, the co-therapies of the invention comprise an effective amount of the compounds, products and/or pharmaceutical compositions described herein and an effective amount of at least one other therapy (e.g., prophylactic or therapeutic agent) that has a different mechanism of action than the compounds, products and/or pharmaceutical compositions described herein. In some embodiments, the co-therapies of the present invention improve the prophylactic or therapeutic effect of the compounds, products and/or pharmaceutical compositions described herein and of the second therapy by functioning together to have an additive or synergistic effect. In certain embodiments, the co-therapies of the present invention reduce the side effects associated with the second therapy (e.g., prophylactic or therapeutic agents).

In some embodiments, the disease or disorder can be treated by administering the compound, product and/or pharmaceutical composition as follows. The blood molar concentration of the compound can be at least an effective concentration and less than a harmful concentration for a first continuous time period that is at least as long as an effective time period and shorter than a harmful time period. The blood molar concentration can be less than the effective concentration after the first continuous time period. For example, the effective concentration can be about 0.1 µM, about 0.2 µM, about 0.5 µM, about 1 µM, about 2 µM, about 3 µM, about 4 µM, about 5 µM, about 6 µM, about 10 µM, or another concentration determined to be effective by one of skill in the art. For example, the harmful concentration can be about 1 µM, about 3 µM, about 10 µM, about 15 µM, about 30 µM, about 100 µM, or another concentration determined to be harmful by one of skill in the art. For example, the effective time period can be about 1 hour, 2 hour, about 4 hours, about 6 hours, about 8 hours, about 10 hours, about 12 hours, about 24 hours, or another time period determined to be effective by one of skill in the art. For example, the harmful time period can be about 12 hours, about 24 hours, about 48 hours, about 72 hours, about 144 hours, or another time period determined to be harmful by one of skill in the art.

In some embodiments, the therapeutically effective amount of the compound, product and/or pharmaceutical composition is selected to produce a blood concentration greater than the $IC_{50}$ of cells of the tumor and less than the $IC_{50}$ of normal cells. In some embodiments, the therapeutically effective amount is selected to produce a blood concentration sufficiently high to kill cells of the tumor and less than the $IC_{50}$ of normal cells.

In some embodiments, the compound, product and/or pharmaceutical composition is administered orally in a dosage form, for example, a tablet, pill, capsule (hard or soft), caplet, powder, granule, suspension, solution, gel, cachet, troche, lozenge, syrup, elixir, emulsion, oil-in-water emulsion, water-in-oil emulsion, and/or a draught.

In various embodiments of the co-therapy, the Compound of the Invention is administered to the patient at a total daily dose in a range from about 400 mg to about 1000 mg. In some embodiments, the Compound of the Invention is administered to the patient at a total daily dose in a range from about 800 mg to about 1000 mg, preferably administered in two daily doses, for example, at about 480 mg BID. The interval between administrations can range from about 4 hours to about 16 hours, e.g., about 12 hours.

In some embodiments, dose modifications of the Compound of the Invention may occur such that the total daily dose is reduced down to 400 to 800 mg total daily. In some embodiments, further dose modification may occur such that the total daily dose is reduced down to a range of 50 mg to 400 mg total daily. In some embodiments, the Compound of the Invention can also be taken once daily. In some embodiments when taken once daily, the interval between administrations can be 18 to 30 hours (e.g., around 24 hours). In some embodiments, the Compound of the Invention can also be taken three times daily for a total dose of around 240 to 1000 mg. When taken as three times daily, the time between administrations can be about 4 hours to 8 hours.

In one feature of the invention, the naphthofuran Compound of the Invention is used in combination with an antimitotic agent, especially those proven to be effective chemotherapy agents, or a pharmaceutically acceptable salt, solvate, hydrate, or prodrug thereof. Examples of antimitotic agents that may be useful as a co-therapy with the Compound of the Invention include and are not limited to: paclitaxel (Abraxane/Taxol), docetaxel (taxotere), BMS-275183, xyotax, tocosal, vinorlebine, vincristine, vinblastine, vindesine, vinzolidine, etoposide (VP-16), teniposide (VM-26), ixabepilone, larotaxel, ortataxel, tesetaxel, and ispinesib.

In some embodiments, the second agent used with the Compound of the Invention in a co-therapy is paclitaxel (Abraxane/Taxol), or a pharmaceutically acceptable salt, solvate, hydrate, or prodrug thereof. In some embodiments, the paclitaxel is administered to the subject at a total weekly dose in a range from about 40 mg/m² to about 100 mg/m². In some embodiments, the paclitaxel is administered to the subject at a total weekly dose of about 80 mg/m². In some embodiments, the paclitaxel is administered to the subject through IV. In some embodiments, the paclitaxel is dosed once a week for three of every four weeks, i.e., 3 weeks on, 1 week off.

In some embodiment, the Compound of the Invention may be administered to a subject firstly, and then the paclitaxel may be administered to the subject. The paclitaxel may be administered to the subject firstly, and then the Compound of the Invention may be administered to a subject. In such case, some interval between the administration of the Compound of the Invention and the paclitaxel may be included. In some embodiments, the present invention refers to a method of curative or prophylactic cancer treatment by administering the paclitaxel to a subject, the method comprising the steps of administering to a subject in need of a curative or prophylactic cancer treatment a dosage of the compound of the invention and a dosage of paclitaxel; wherein the first dosage is administered before or after administering the paclitaxel to the subject.

In an aspect, the invention provides a curative or prophylactic cancer treatment in, preferably, a human subject, the method comprising administering to a subject in need thereof a therapeutically effective amount of a naphthofuran compound, referred to herein as "Compound 1," and having the structure shown below, or a pharmaceutically acceptable salt, solvate, hydrate, or prodrug thereof

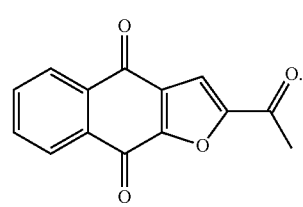

(1)

In some embodiments, the compound is administered to the subject at a total daily dose in a range of from about 160 mg to about 1000 mg. In some embodiments, the compound is administered to the subject at a total daily dose selected from the group consisting of about 160 mg, about 320 mg, about 640 mg, about 800 mg, and about 960 mg. In some embodiments, the compound is administered to the subject at a total daily dose of about 960 mg.

In some embodiments, the compound is administered twice a day (BID). In some embodiments, the compound is administered to the subject at a dose in a range of from about 80 mg BID to about 480 mg BID. In some embodiments, the compound is administered to the subject at a dose selected from the group consisting of about 80 mg BID, about 160 mg BID, about 320 mg BID, about 400 mg BID, and about 480 mg BID. In some embodiments, the compound is administered to the subject at a dose of about 480 mg BID.

In some embodiments, the compound is administered BID where the timing between administrations of the compound is in the range from about 4 hours between administrations to about 16 hours between administrations. In some embodiments, the compound is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours and/or at least 16 hours. In some embodiments, the compound is administered to the subject at a dose in a range of from about 80 mg BID to about 480 mg BID where the timing between administrations of the compound is in the range from about 4 hours between administrations to about 16 hours between administrations. In some embodiments, the compound is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours and/or at least 16 hours. In some embodiments, the compound is administered to the subject at a dose selected from the group consisting of about 80 mg BID, about 160 mg BID, about 320 mg BID, about 400 mg BID, and about 480 mg BID, where the timing between administrations of the compound is in the range from about 4 hours between administrations to about 16 hours between administrations. In some embodiments, the compound is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours and/or at least 16 hours. In some embodiments, the compound is administered to the subject at a dose of about 480 mg BID where the timing between administrations of the compound is about 12 hours between administrations. In some embodiments, the compound is administered to the subject at a dose of about 80 mg BID where the timing between administrations of the compound is about 12 hours between administrations. In some embodiments, the compound is administered to the subject at a dose of about 400 mg BID where the timing between administrations of the compound is about 12 hours between administrations. In some embodiments, the compound is administered to the subject at a dose of about 320 mg BID where the timing between administrations of the compound is about 12 hours between administrations. In some embodiments, the compound is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours and/or at least 16 hours. In some embodiments, the compound is administered to the subject at a dose of about 80 mg BID, about 160 mg BID, about 320 mg BID, about 400 mg BID, and about 480 mg BID where the timing between administrations of the compound is more at least 5 hours, preferably, in the range from about 5 hours between administrations to about 15 hours between administrations.

In some embodiments, the Compound of the Invention is administered orally in conjunction with fluid on an empty stomach. In some embodiments, the fluid is milk or water.

In some embodiments, the naphthofuran compound is a polymorph of the compound shown below, referred to herein as "Compound 1,"

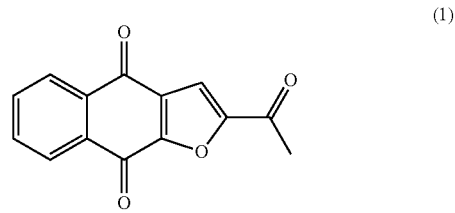 [SMILES: CC(=O)c1cc2c(o1)C(=O)c1ccccc1C2=O]

(1)

For example, in some embodiments, the polymorph is a polymorph of 2-acetyl-4H, 9H-naphtho[2,3-b]furan-4,9-dione characterized by an X-ray diffraction pattern substantially similar to that set forth WO 2011/116398 and WO 2011/116399, the contents of each of which are hereby incorporated by reference in their entireties. X-ray powder diffraction analysis shown in FIG. 1 of WO 2011/116398 and WO 2011/116399 was performed using a Philips PW1800 diffractometer using Cu radiation at 40 KV/30 mA over the range of 5° to 700 with a step size of 0.03° and a counting time of 3 hours. Analysis was performed from 2-45° 2-theta using the following conditions: divergence slit: 0.6 mm, anti-scatter slit: 0.6 mm, receiving slit: 0.1 mm, detector slit: 0.6 mm, step size: 0.02°, step time: 5 seconds. In some embodiments, the polymorph is a polymorph of 2-acetyl-4H, 9H-naphtho[2,3-b]furan-4,9-dione characterized by an X-ray diffraction pattern substantially similar to that set forth in WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in WO 2011/116398 and WO 2011/116399. X-ray powder diffraction analysis shown in FIGS. 2 and 3 of WO 2011/116398 and WO 2011/116399 was performed using a Bruker D8 Advance diffractometer. Analysis was performed from 2-45° 2-theta using the following conditions: divergence slit: 0.6 mm, anti-scatter slit: 0.6 mm, receiving slit: 0.1 mm, detector slit: 0.6 mm, step size: 0.02°, step time: 5 seconds.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b] furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

The present invention also provides naphthofuran compounds in particle form.

In some embodiments, the naphthofuran compound in particle form is a particle of a compound according to Formula I or a salt or solvate thereof,

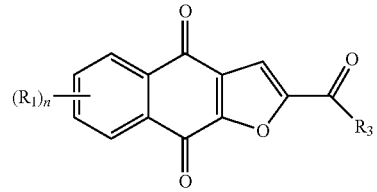

Formula I wherein the particle has a diameter of less than or equal to about 200 μm; wherein each $(R_1)$ is independently selected from the group consisting of hydrogen, halogen, fluorine, cyano, nitro, $CF_3$, $OCF_3$, alkyl, methyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NH_2$; wherein n is 4; wherein $R_3$ is selected from the group consisting of hydrogen, halogen, fluorine, cyano, $CF_3$, $OCF_3$, alkyl, methyl, substituted alkyl, halogen-substituted alkyl, hydroxyl-substituted alkyl, amine-substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NR_bR_c$; wherein $R_a$ is/are independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, and substituted aryl; and wherein $R_b$ and $R_c$ are independently selected from the group consisting of hydrogen, alkyl, substituted alkyl, cycloalkyl, substituted cycloalkyl, heterocycle, substituted heterocycle, aryl, and substituted aryl, or $R_b$ and $R_c$ together with the N to which they are bonded form a heterocycle or substituted heterocycle.

In some embodiments, each $(R_1)$ is independently selected from the group consisting of hydrogen, methyl, F (fluorine), Cl, Br, I, OH, and $NH_2$; $R_3$ is selected from the group consisting of methyl and $C(R_8)_3$, and each $(R_8)$ is independently selected from the group consisting of hydrogen, methyl, F (fluorine), Cl, Br, I, OH, and $NH_2$. In some embodiments, at most two of $(R_1)$ and $(R_8)$ are F (fluorine) with the remainder being hydrogen. In some embodiments, $R_3$ is methyl. In a further embodiment, the compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, an enantiomer, diastereomer, tautomer, and a salt or solvate thereof.

In some embodiments, the naphthofuran compound in particle form is a particle of Compound 1.

In some embodiments, the naphthofuran compound in particle form is a particle of a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

In some embodiments, the particle has a diameter of less than or equal to about 160 μm, about 150 μm, about 120 μm, about 100 μm, about 50 μm, about 40 μm, or about 20 μm. In a further embodiment, the particle has a diameter of less than or equal to about 10 μm, about 5 μm, about 4 μm, about 3 μm, about 2 μm, about 1 μm, about 0.5 μm, about 0.2 μm, or about 0.1 μm.

In some embodiments according to the invention, a pharmaceutical composition includes particles of a compound, for example, a naphthofuran, according to Formula I or a salt or solvate thereof. For example, in some embodiments, a pharmaceutical composition includes particles of Compound 1. For example, in some embodiments, a pharmaceutical composition includes particles of a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

A fraction of the cumulative total of the particles can have a diameter of less than or equal to about 200 μm. In some embodiments, a fraction of a set of particles can be at least about 1%, at least about 5%, at least about 10%, at least about 20%, or at least about 30% of the total number of particles in the set. In some embodiments, the fraction is a substantial fraction. For example, a "substantial fraction" of a set of particles can be at least about 99%, at least about 95%, at least about 90%, at least about 85%, at least about 80%, at least about 75%, at least about 70%, at least about 60%, or at least about 50% of the total number of particles in the set. Each ($R_1$) can be independently selected from the group consisting of hydrogen, halogen, fluorine, cyano, nitro, $CF_3$, $OCF_3$, alkyl, methyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NH_2$. n can be a positive integer; for example, n can be 4. $R_3$ can be selected from the group consisting of hydrogen, halogen, fluorine, cyano, $CF_3$, $OCF_3$, alkyl, methyl, substituted alkyl, halogen-substituted alkyl, hydroxyl-substituted alkyl, amine-substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NR_bR_c$. The $R_a$ can be independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, and substituted aryl. $R_b$ and $R_c$ can be independently selected from the group consisting of hydrogen, alkyl, substituted alkyl, cycloalkyl, substituted cycloalkyl, heterocycle, substituted heterocycle, aryl, and substituted aryl, or $R_b$ and $R_c$ together with the N to which they are bonded form a heterocycle or substituted heterocycle.

In some embodiments according to the invention, each ($R_1$) can be independently selected from the group consisting of hydrogen, methyl, F (fluorine), Cl, Br, I, OH, and $NH_2$. $R_3$ can be selected from the group consisting of methyl and $C(R_8)_3$. Each ($R_8$) can be independently selected from the group consisting of hydrogen, methyl, F (fluorine), Cl, Br, I, OH, and $NH_2$. In some embodiments, at most two of ($R_1$) and $R_8$ can be F (fluorine) with the remainder being hydrogen.

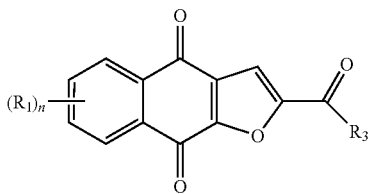

Formula I

In some embodiments according to the invention, a compound according to Formula I is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, and 2-ethyl-naphtho[2,3-b]furan-4,9-dione. In some embodiments, a compound according to Formula I is Compound 1. In some embodiments, a compound according to Formula I is a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

For example, the pharmaceutical composition can have at least about 90% of the cumulative total of particles having a particle size of less than or equal to about 160 μm, 100 μm, 40 μm, 20 μm, 10 μm, 5 μm, 3 μm, or 2 μm. For example, the pharmaceutical composition can have at least about 50% of the cumulative total of particles having a particle size of less than or equal to about 160 μm, 100 μm, 40 μm, 20 μm, 10 μm, 5 μm, 3 μm, 2 μm, 1 μm, or 0.5 μm. For example, the pharmaceutical composition can have at least about 10% of the cumulative total of the particles having a particle size of less than or equal to about 160 μm, 100 μm, 40 μm, 20 μm, 5 μm, 2 μm, 1 μm, 0.5 μm, or 0.1 μm. In the pharmaceutical composition, the particles can have a median diameter of, for example, less than or equal to about 160 μm, 40 μm, 20 μm, 10 μm, 5 μm, 4 μm 3 μm, 2 μm, 1 μm, 0.5 μm, 0.3 μm, or 0.2 μm. For example, the particles can have a median diameter of from about 0.2 μm to about 50 μm, or a median diameter of from about 0.5 μm to about 30 μm. For example, the pharmaceutical composition can have the cumulative total of particles having a ratio of mean diameter over median diameter of at most about 2 μm. The pharmaceutical invention can have particles that include the compound in a crystalline state, in at least two different polymorph states.

In some embodiments, the pharmaceutical composition includes a compound of Formula I or a polymorph thereof in particle form, where the particle or particles are less than 20 micron, 10 micron, 5 micron, 2 micron, 1 micron or 0.5 micron.

The present invention provides a substantially pure compound of Formula II,

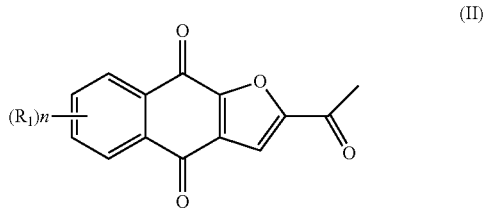

(II)

wherein each $R_1$ is independently H, Cl, or F; and n is 0, 1, 2, 3, or 4. In some embodiments, the compound of Formula II is in particle form.

In some embodiments, the substantially pure compound is Compound 1. In some embodiments, Compound 1 is in particle form.

In some embodiments, the substantially pure compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof.

In some embodiments, the substantially pure compound is a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

In some embodiments, the polymorph of Compound 1 is in particle form.

In some embodiments, the compound, product and or pharmaceutical composition has a purity of at least about 80%, about 85%, about 90%, about 95%, or about 99%. In some embodiments, the compound, product and or pharmaceutical composition has a purity of at least about 95.5%, about 96%, about 96.5%, about 97%, about 97.5%, about 98%, about 98.5%, about 99%, or about 99.5%. In some embodiments, the compound, product and or pharmaceutical composition has a purity of at least about 99.1%, about 99.2%, about 99.3%, about 99.4%, about 99.5%, about 99.6%, about 99.7%, about 99.8%, or about 99.9%.

In some embodiments, the compound, product and/or pharmaceutical composition has impurities of at most about 10%, about 5%, about 1%, about 0.15%, or about 0.5%. In some embodiments, the compound, product and or pharmaceutical composition contains, for each single impurity, at most about 0.5%, about 0.2%, about 0.15%, or about 0.1%. In a further embodiment, the impurities are one or more from the group consisting of 2-acetyl-2,3-dihydronaphtho[2,3-b]furan-4,9-dione, 2,6-Diacetyl-naphtho[2,3-b]furan-4,9-dione, 2,7-Diacetyl-naphtho[2,3-b]furan-4,9-dione, 3-Acetyl-naphtho[2,3-b]furan-4,9-dione, Naphtho[2,3-b]furan-4,9-dione, Naphtho[2,3-b]furan-4,9-dione, Naphtho[2,3-b]furan-4,9-diol, and 1-(4,9-Dihydroxy-naphtho[2,3-b]furan-2-yl)-ethanone.

In some embodiments, the impurities include a residual solvent. In some embodiments, the solvent is selected from the group consisting of ethyl acetate (EtOAc), toluene, Ethanol, methanol, chloroform, and $CH_2Cl_2$/hexane.

In some embodiments, the purity is determined with HPLC (High Performance Liquid Chromatography). In some embodiments, the purity is determined with NMR (Nuclear Magnetic Resonance). In a further embodiment, the purity is determined with both HPLC and NMR.

The invention also provides a polymorph of Compound 1 in a particle form, where the compound is in a highly purified form, product and/or pharmaceutical composition. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

The polymorph of Compound 1 is in a particle form. In some embodiments, the polymorph of Compound 1 is in a particle form, where the particle has a diameter of less than or equal to about 160 μm, about 150 μm, about 120 μm, about 100 μm, about 50 μm, about 40 μm, or about 20 μm. In some embodiments, the polymorph of Compound 1 in particle form is in a population of particles, where the population of particles have a $D_{50}$ (i.e., the median point of the particle size distribution that divides the distribution in two equal parts) of less than or equal to about 160 μm, about 150 μm, about 120 μm, about 100 μm, about 50 μm, about 40 μm, or about 20 μm. In some embodiments, the polymorph of Compound 1 is in a particle form, where the particle has a diameter of less than or equal to about 10 μm, about 5 μm, about 4 μm, about 3 μm, about 2 μm, about 1 μm, about 0.5 μm, about 0.2 μm, or about 0.1 μm. In some embodiments, the polymorph of Compound 1 in particle form is in a population of particles, where the population of particles have a $D_{50}$ of less than or equal to about 10 μm, about 5 μm, about 4 μm, about 3 μm, about 2 μm, about 1 μm, about 0.5 μm, or about 0.2 μm.

A fraction of the cumulative total of the particles of a polymorph of Compound 1 can have a diameter or $D_{50}$ of less than or equal to about 200 μm. In some embodiments, a fraction of a set of particles can be at least about 1%, at least about 5%, at least about 10%, at least about 20%, or at least about 30% of the total number of particles in the set. In some embodiments, the fraction is a substantial fraction. For example, a "substantial fraction" of a set of particles can be at least about 99%, at least about 95%, at least about 90%, at least about 85%, at least about 80%, at least about 75%, at least about 70%, at least about 60%, or at least about 50% of the total number of particles in the set.

In some embodiments, the population of particles of a polymorph of Compound 1 can have at least about 90% of the cumulative total of particles having a particle size of less than or equal to about 160 μm, 100 μm, 40 μm, 20 μm, 10 μm, 5 μm, 3 μm, or 2 μm, 1 μm or 0.5 μm. For example, the population of particles of a polymorph of Compound 1 can have at least about 50% of the cumulative total of particles having a particle size of less than or equal to about 160 μm, 100 μm, 40 μm, 20 μm, 10 μm, 5 μm, 3 μm, 2 μm, 1 μm, or 0.5 μm. For example, the population of particles of a polymorph of Compound 1 can have at least about 10% of the cumulative total of the particles having a particle size of less than or equal to about 160 μm, 100 μm, 40 μm, 20 μm, 5 μm, 2 μm, 1 μm, 0.5 μm, or 0.1 μm. In the population of particles of a polymorph of Compound 1, the particles can have a median diameter of, for example, less than or equal to about 160 μm, 40 μm, 20 μm, 10 μm, 5 μm, 4 μm, 3 μm, 2 μm, 1 μm, 0.5 μm or 0.2 μm. For example, the particles can have a median diameter of from about 0.002 μm to about 50 μm, or a median diameter of from about 0.2 μm to about 30 μm. For example, the population of particles of a polymorph of Compound 1 can have the cumulative total of particles having a ratio of mean diameter over median diameter of at most about 2. The population of particles of a polymorph of Compound 1 can have particles that include the compound in a crystalline state, in at least two different polymorph states.

In some embodiments, the polymorph of Compound 1 is in a particle form, where the particle has a diameter of less than or equal to about 20 micron, 10 micron, 5 micron, or 2 3 micron, 2 micron, 1 micron, 0.5 micron, 0.2 micron, or 0.1 micron. In some embodiments, the polymorph of Compound 1 in particle form is in a population of particles, where the population of particles have a $D_{50}$ of less than or equal to about 20 micron, 10 micron, 5 micron, 4 micron, 5 micron, 3 micron, 2 micron, 1 micron, 0.5 micron or 0.2 micron.

The present invention also provides a pharmaceutical composition, which includes a therapeutically effective amount of the substantially pure naphthofuran compound and a pharmaceutically acceptable carrier, excipient, or diluent. The excipient can include, for example, a glycerol ester of a fatty acid, a glycerol ester of a saturated fatty acid, a glycerol ester of a saturated fatty acid having from 8 to 18 carbons, glyceryl laurate, polyethylene glycol, cellulose, microcrystalline cellulose, carboxymethylcellulose, a phosphatidylcholine, a lipid, a sterol, cholesterol, a surfactant, a polysorbate, and/or a polyoxyethylene sorbitan alkylate.

In some embodiments according to the invention, an item of manufacture can include a container containing a therapeutically effective amount of the pharmaceutical composition and a pharmaceutically acceptable excipient.

A method for producing a compound, product and/or pharmaceutical composition according to some embodiments of the invention can include milling the compound to form the particles. For example, the compound can be ball milled, roll milled, jet milled, wet milled, ultrasonically milled, ground, or treated with a combination of these and/or other milling procedures. The temperature of the compound can be reduced, for example, reduced to a cryogenic temperature, and milled. Such reduction in temperature can render the compound more brittle and more amenable to particle size reduction by milling.

A method for producing a compound, product and/or pharmaceutical composition according to some embodiments of the invention can include crystallization. The particle size distribution (PSD) obtained during crystallization is influenced by a combination of various mechanisms that occur during crystallization, such as nucleation, growth, aggregation, attrition, breakage, etc. When the particle size cannot be consistently controlled during crystallization to meet the desired specifications, an extra processing step such as dry milling can be included.

In some embodiments according to the present invention, a composition for reducing or inhibiting the replication or spread of neoplastic cells includes a set of particles selected by the following method. A compound according to Formula I or a salt or solvate thereof can be provided.

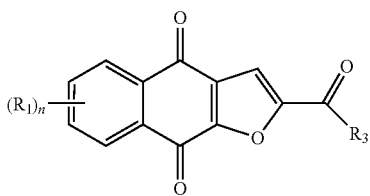

Formula I

In some embodiments, Compound 1 or a salt or solvate thereof can be provided. In some embodiments, a polymorph of Compound 1 can be provided. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399. In some embodiments, the polymorph is a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

At least one set of particles including the compound can be prepared. The particle size distribution of each at least one set of particles can be determined. At least one set of particles can be administered to neoplastic cells and to normal cells at a predetermined concentration and for a predetermined period of time. The effect of the particles on the metabolism and/or division of the neoplastic cells and the normal cells can be observed. An effectivity rating can be assigned to each set of particles based on the effect of the particles on the neoplastic cells. A toxicity rating can be assigned to each set of particles based on the effect of the particles on the normal cells. The effectivity rating and/or the toxicity rating of the at least one set of particles having a first particle size distribution can be compared with the effectivity rating and/or the toxicity rating of at least one other set of particles having a particle size distribution different than the first particle size distribution. The set of particles having an effectivity rating greater than, a toxicity rating less than, and/or a weighted effectivity rating and toxicity rating sum greater than the at least one other set of particles can be selected as an optimum set. For example, the particle size distribution of the optimum set of particles can be identified as an optimum particle size distribution. For example, the optimum set of particles can be included in the composition. For example, the effectivity rating can be proportional to antitumor activity. For example, the effectivity rating can be based on inhibition of metabolism and/or division of the neoplastic cells. For example, the toxicity rating can be inversely proportional to tolerability. For example, the toxicity rating can be based on inhibition of metabolism and/or division of normal cells. For example, the at least one set of particles can be administered to the neoplastic cells and to the normal cells in vitro. For example, the effectivity rating can be the $IC_{50}$ of the neoplastic cells. For example, the toxicity rating can be the $IC_{50}$ of the normal cells. For example, the at least one set of particles can be administered to the neoplastic cells and to the normal cells in vivo in a test animal. The test animal can be, for example, a mammal, primate, mouse, rat, guinea pig, rabbit, or dog. The effectivity rating can be the decrease in volume of the neoplastic cells, and the toxicity rating can be the decrease in mass of the test animal.

In some embodiments, preparing the one set of particles including the compound can include isolating particles of a predetermined particle size distribution by dissolving and dispersing the compound, dissolving and dispersing the compound with a microfluidic technique, dissolving and dispersing the compound with cavitation or nebulization, milling the compound, ball milling the compound, roll milling the compound, jet milling the compound, wet milling the compound, ultrasonically milling the compound, grinding the compound, and/or sieving the compound. The particles can be suspended in a pharmaceutically acceptable excipient. Determining the particle size distribution can include using a technique selected from the group consisting of sieve analysis, optical microscopic counting, electron micrograph counting, electroresistance counting, sedimentation time, laser diffraction, acoustic spectroscopy, and combinations.

A method of treating a neoplasm or other cell proliferation disorder can include administering to a human, mammal, or animal afflicted with a neoplasm a therapeutically effective amount of a composition including an optimum set of particles of the composition having an optimum particle size and distribution.

The present invention provides a process of preparing a naphthofuran compound. The process includes reacting a naphthodihydrofurane compound or a mixture including the naphthodihydrofurane compound with an oxidizing agent in a first solvent. In some embodiments, the mixture further includes a naphthofuran compound. In some embodiments, the naphthofuran compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the oxidizing agent is manganese dioxide. In some embodiments, the first solvent is toluene. In some embodiments, the process further includes filtering the oxidization product through a pad of activated carbon. In some embodiments, the process further includes crystallizing the naphthofuran compound by evaporating the first solvent. In some embodiments, the process further includes re-crystallizing the naphthofuran compound with a second solvent. In some embodiments, the second solvent is ethyl acetate. In some embodiments, the process further includes slurrying the naphthofuran compound with a second solvent, heating the slurry, and cooling the slurry.

The present invention provides a process of preparing a substantially pure naphthofuran compound. The process includes crystallizing a naphthofuran compound with a first solvent, and re-crystallizing the naphthofuran compound with a second solvent. The present invention provides another process of preparing a substantially pure naphthofuran compound. The process includes crystallizing a naphthofuran compound with a first solvent, slurrying the crystalline naphthofuran compound with a second solvent, heating the slurry, and cooling the slurry. In some embodiments, the naphthofuran compound selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the first solvent is toluene. In some embodiments, the second solvent is ethyl acetate.

The present invention provides a naphthofuran compound prepared by any one of the above processes. In some embodiments, the naphthofuran compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the naphthofuran compound has a purity of at least about 80%, about 85% or about 90%, about 95%, or about 99%. In some embodiments, the naphthofuran compound has impurities of at most about 10%, about 5%, about 2%, or about 1%, about 0.5%, about 0.2%, about 0.15%, or about 0.1%.

The invention provides methods for preparing particles of Compound 1, including particles of a polymorph of Compound 1, particles of highly pure forms of Compound 1 and particles of highly pure forms of a polymorph of Compound 1. In some embodiments, particles having a desired median particle size, for example, about 20 microns, are produced by milling crystals of Compound 1, including crystals of a purified form of Compound 1, crystals of a polymorph of Compound 1 and/or crystals of a purified form of a polymorph of Compound 1. For example, the crystals are milled using a jet milling method where the venturi pressure is about 40, the mill pressure is about 100, and the feed rate is approximately 1304 g/hour.

The invention also provides kits and/or methods for treating a specific, selected patient population suitable for therapeutic administration of a compound of the disclosure by detecting the level of expression of one or more biomarkers associated with cancer stemness. A biomarker is deemed to be associated with cancer stemness when its expression is elevated in patient or sample from a patient suffering from a cancer known to have cancer stem cells and/or known to have aberrant Stat3 pathway activities as compared a baseline, control or normal level of expression of the same marker, e.g., the level in a patient that is not suffering from a cancer known to have cancer stem cells and/or known to have aberrant Stat3 pathway activities.

In some embodiments, the biomarker associated with cancer stemness is phosphorylated STAT3 (p-STAT3). In some embodiments, the biomarker associated with cancer stemness is β-catenin. In some embodiments, the biomarker associated with cancer stemness is NANOG. In some embodiments, a combination of biomarkers associated with cancer stemness is used, where the combination is selected from the group consisting of two or more of p-STAT3, β-catenin, and NANOG. In some embodiments, a combination of biomarkers associated with cancer stemness is used, where the combination is selected from the group consisting of three of p-STAT3, β-catenin, and NANOG.

In the methods and/or kits of the disclosure, the level of expression of one or more cancer sternness markers is detected in a patient or a sample from a patient, and where the patient or sample has an elevated level of one or more cancer stemness markers as compared to a control level of expression, the patient is then administered a therapeutically effective amount of a compound of the disclosure.

In some embodiments of these methods, the method is an in vivo method. In some embodiments of these methods, the method is an in situ method. In some embodiments of these methods, the method is an ex vivo method. In some embodiments of these methods, the method is an in vitro method.

The invention also provides kits and/or methods for of identifying or otherwise refining, e.g., stratifying, a patient population suitable for therapeutic administration of a compound of the disclosure by detecting the level of expression of one or more biomarkers associated with cancer stemness. A biomarker is deemed to be associated with cancer stemness when its expression is elevated in patient or sample from a patient suffering from a cancer known to have cancer stem cells and/or known to have aberrant Stat3 pathway activities as compared a baseline, control or normal level of expression of the same marker, e.g., the level in a patient that is not suffering from a cancer known to have cancer stem cells and/or known to have aberrant Stat3 pathway activities.

In some embodiments, the biomarker associated with cancer stemness is phosphorylated STAT3 (p-STAT3). In some embodiments, the biomarker associated with cancer stemness is β-catenin. In some embodiments, the biomarker associated with cancer stemness is NANOG. In some embodiments, a combination of biomarkers associated with cancer stemness is used, where the combination is selected from the group consisting of two or more of p-STAT3, β-catenin, and NANOG. In some embodiments, a combination of biomarkers associated with cancer stemness is used, where the combination is p-STAT3, β-catenin, and NANOG.

In the methods and/or kits of the disclosure, the level of expression of one or more cancer stemness markers is detected in a patient or a sample from a patient, and where the patient or sample has an elevated level of one or more cancer stemness markers as compared to a control level of expression, the patient is then administered a therapeutically effective amount of a compound of the disclosure.

In some embodiments of these methods, the method is an in vivo method. In some embodiments of these methods, the method is an in situ method. In some embodiments of these methods, the method is an ex vivo method. In some embodiments of these methods, the method is an in vitro method.

BRIEF DESCRIPTION OF THE DRAWINGS

FIG. 6A depicts the relationship between Progression Free Survival (PFS) and exposure of a Compound of the Invention in colorectal cancer (CRC) patients. In CRC patients, a statistically significant difference was seen in PFS between those with Compound of the Invention plasma concentrations above 2.0 uM for greater than 4 hours and those who did not reach that level of exposure. FIG. 6B depicts the overall survival (OS) in evaluable CRC patients. OS of evaluable CRC patients treated with a Compound of the Invention (defined as ≥4 weeks of Compound of the Invention, 80% compliance) compared with historical controls [Cetuximab for the treatment of colorectal cancer, 2007, N. Engl. J. Med. 357 2040-2048]. FIG. 6C depicts PFS in evaluable CRC patients. PFS of evaluable CRC patients treated with a Compound of the Invention (defined as ≥4 weeks of Compound of the Invention, 80% compliance) compared historical controls (Open-Label Phase III Trial of Panitumumab Plus Best Supportive Care Compared with Best Supportive Care Alone in Patients with Chemotherapy-Refractory Metastatic Colorectal Cancer, 2007, J. Clin. Onc. 25: 1658-1665].

FIGS. 7A and 7B depict representative slides of archival tissue samples from CRC patients that were analyzed by immunohistochemistry (IHC) with antibodies against phosphorylated STAT3 (p-STAT3) and β-catenin. FIGS. 7C and 7D depict an analysis of CRC patients treated with a Compound of the Invention that demonstrated a trend towards improvement in survival for patients with high p-STAT3 (compared with patients having low or negative p-STAT3), and a significant improvement in survival for patients with nuclear β-catenin localization (compared with patients having β-catenin localized to the cell membranes).

DETAILED DESCRIPTION OF THE INVENTION

Figure 1:
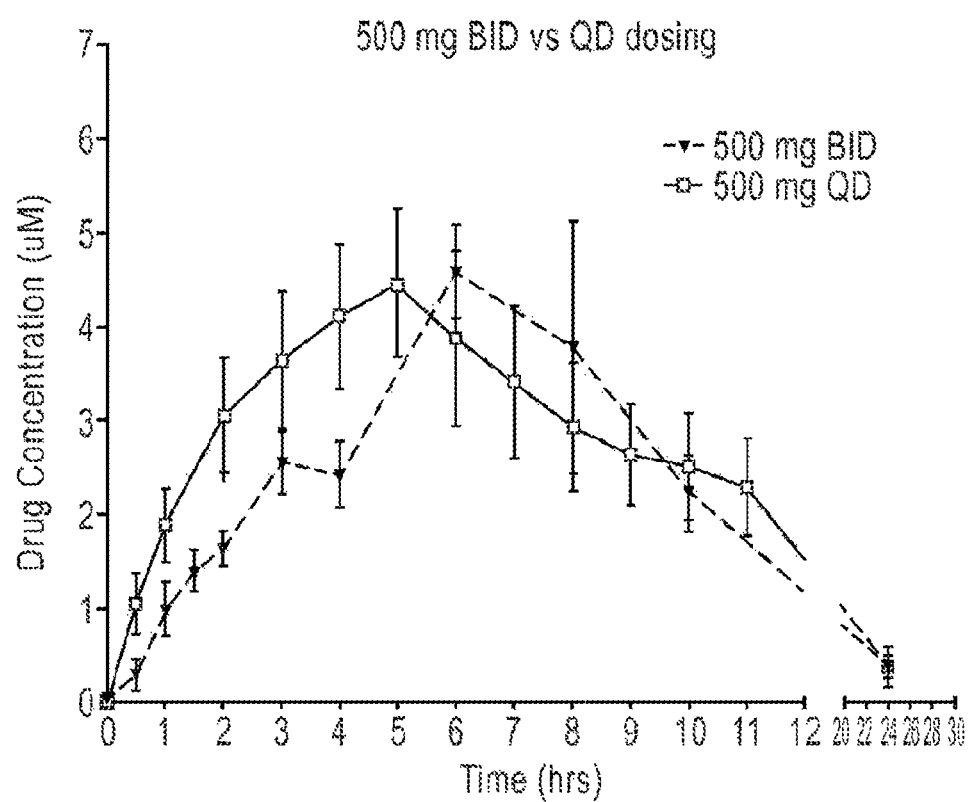
FIG. 1 is a graph that compares the pharmacokinetics of BID dosing versus QD dosing in patients, where the patients were dosed at 500 mg during each dose. Medication was administered with a four-hour interval in between the two doses during the same day for the 500 mg BID regimen.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without parting from the spirit and scope of the invention. All references cited herein are incorporated by reference as if each had been individually incorporated.

In this text, a "substantial fraction" of a set of particles can be at least about 99%, at least about 95%, at least about 90%, at least about 85%, at least about 80%, at least about 75%, at least about 70%, at least about 60%, or at least about 50% of the total number of particles in the set.

The anti-cancer stem cell activity of a composition can be determined in vitro or in vivo. For example, antitumor activity of a composition can be determined in vitro by administering the compound and measuring the self-renewal and survival of cancer stem cells, For example, the antitumor activity of a compound can be assessed in vitro by comparing the behavior of tumor cells to which the compound has been administered with the behavior of tumor cells to which the compound has not been administered (a control). For example, antitumor activity of a composition can be determined in vivo by measuring, in an animal to which the compound has been administered, the change in volume of a tumor, by applying a metastatic model, and/or by applying an orthotopic model. For example, the antitumor activity of a compound can be assessed in vivo by comparing an animal to which the compound has been administered to an animal to which the compound has not been administered (a control).

The tolerability of a composition can be determined in vitro or in vivo. For example, tolerability of a composition can be determined in vitro by administering the compound and measuring the division rate of normal cells, by measuring the nutrient uptake of normal cells, by measuring indicators of metabolic rate of normal cells other than nutrient uptake, by measuring the growth of normal cells, and/or by measuring another indicator of the vitality of normal cells. For example, the tolerability of a compound can be assessed in vitro by comparing the behavior of normal cells to which the compound has been administered with the behavior of normal cells to which the compound has not been administered (a control). For example, tolerability of a composition can be determined in vivo by measuring, in an animal to which the compound has been administered, body weight or food intake or making clinical observations, such as hair retention or loss, activity, and/or responsiveness to stimuli. For example, the tolerability of a compound can be assessed in vivo by comparing an animal to which the compound has been administered to an animal to which the compound has not been administered (a control).

A compound, product and/or pharmaceutical composition can be assigned an effectivity rating and/or a toxicity rating. For example, the effectivity rating can be proportional to antitumor activity or can be a monotonically increasing function with respect to antitumor activity. For example, the toxicity rating can be inversely proportional to tolerability or can be a monotonically decreasing function with respect to tolerability. A naphthofuran compound has been reported to lack in vivo antitumor activity. See, M. M. Rao and D. G. I. Kingston, J. Natural Products, 45(5) (1982) 600-604. Furthermore, the compound has been reported to be equally toxic to cancer cells and normal cells. That is, the compound was reported as killing both cancer cells and normal cells equally, concluding the compound has no potential for cancer treatment. See, K. Hirai K. et al., Cancer Detection and Prevention, 23(6) (1999) 539-550; Takano A. et al., Anticancer Research 29:455-464, 2009.

However, experimental studies reported herein indicate that when the compound is administered as particles having an appropriate particle size distribution to achieve a certain pharmacokinetic exposure as described in this publication, the compound does have selective antitumor activity.

For the purposes of the present invention, "bioavailability" of a drug is defined as the relative amount of drug from an administered dosage form which enters the systemic circulation and the rate at which the drug appears in the blood stream Bioavailability is governed by at least three factors: (i) absorption which controls bioavailability, followed by (ii) its tissue re-distribution and (iii) elimination (metabolic degradation plus renal and other mechanisms).

"Absolute bioavailability" is estimated by taking into consideration tissue re-distribution and biotransformation (i.e., elimination) which can be estimated in turn via intravenous administration of the drug. Unless otherwise indicated, "HPLC" refers to high performance liquid chromatography; "pharmaceutically acceptable" refers to physiologically tolerable materials, which do not typically produce an allergic or other untoward reaction, such as gastric upset, dizziness and the like, when administered to a mammal; "mammal" refers to a class of higher vertebrates including man and all other animals that nourish their young with milk secreted by mammary glands and have the skin usually more or less covered with hair; and "treating" is intended to encompass relieving, alleviating, or eliminating at least one symptom of a disease(s) in a mammal.

The term "treatment", as used herein, is intended to encompass administration of compounds according to the invention prophylactically to prevent or suppress an undesired condition, and therapeutically to eliminate or reduce the extent or symptoms of the condition. Treatment also includes preventing the relapse of an undesired condition, delaying the progression of an undesired condition, and preventing or delaying the onset of an undesired condition. Treatment according to the invention is given to a human or other mammal having a disease or condition creating a need of such treatment. Treatment also includes application of the compound to cells or organs in vitro. Treatment may be by systemic or local administration.

An effective amount is the amount of active ingredient administered in a single dose or multiple doses necessary to achieve the desired pharmacological effect. A skilled practitioner can determine an effective dose for an individual patient or to treat an individual condition by routine experimentation and titration well known to the skilled clinician. However, unexpected clinical responses from a patient population to a pharmaceutical formulation or composition may dictate unforeseen changes or adjustment to an aspect of the treatment such as the dosage, intervals in between drug administrations, and/or ways of drug administration. The actual dose and schedule may vary depending on whether the compositions are administered in combination with other drugs, or depending on inter-individual differences in pharmacokinetics, drug disposition, and metabolism. Similarly, amounts may vary for in vitro applications. Where disclosed herein, dose ranges, unless stated otherwise, do not necessarily preclude use of a higher or lower dose of a component, as might be warranted in a particular application.

The descriptions of pharmaceutical compositions provided herein include pharmaceutical compositions which are suitable for administration to humans. It will be understood by the skilled artisan, based on this disclosure, that such compositions are generally suitable for administration to any mammal or other animal. Preparation of compositions suitable for administration to various animals is well understood, and the ordinarily skilled veterinary pharmacologist can design and perform such modifications with routine experimentation based on pharmaceutical compositions for administration to humans.

Compound Structure and Properties

A naphthofuran compound of Formula I, such as 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, was practically insoluble in water and a broad panel of solvents tested, including DMSO (dimethyl sulfoxide), N-methylpyrrolidine, DMA (dimethylacetamide), ethanol, PEG400 (polyethylene glycol 400), propylene glycol, Cremophor EL (polyethoxylated castor oil), Labrasol (Caprylocaproyl Macrogolglycerides (Polyoxylglycerides)), Labrafil M (vegetable oil PEG-6 (polyethylene glycol) ester), and Capryol (propylene glycol caprylate). The naphthofuran compound may be soluble in a range of polar organic solvents, such as certain halocarbons, e.g., chlorocarbons, like methylene chloride, esters, ethyl acetate, carboxylic acids, like acetic acid, ketones, like acetone, and alcohols, like methanol. The naphthofuran compound was found to be soluble in methylene chloride and ethyl acetate.

Some other compounds that may exhibit an improvement in their pharmacokinetic profile with a decrease in particle size of the form in which they are administered to an animal, a mammal, or a human, as observed for the compound tested in examples, include those presented as Formula I, and salts and solvates thereof.

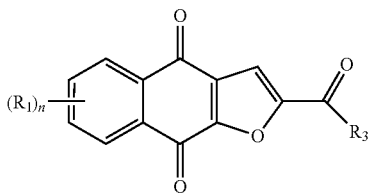

Formula I

In Formula I, the notation $(R_1)_n$ indicates that an $(R_1)$ substituent is independently substituted at each available position along the benzene ring. For example, with n equal to 4, the four $R_1$ substituents may all be the same, or they may each be different from any other. For example, each $(R_1)$ can be independently selected from the group consisting of hydrogen, halogen, fluorine, cyano, nitro, $CF_3$, $OCF_3$, alkyl, methyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NH_2$. Alkyl can include moieties having, for example, from 1 to 8 carbon atoms connected by single bonds, alkenyl can include moieties having, for example, from 2 to 8 carbon atoms connected by one or more double bonds, and alkynyl can include moieties having, for example, from 2 to 8 carbon atoms connected by one or more triple bonds. Substituents can include moieties such as hydrogen, halogen, cyano, nitro, aryl, $OR_a$, $SR_a$, and $NH_2$. For example, each $(R_1)$ can be independently selected from the group consisting of hydrogen, methyl, F (fluorine), Cl (chlorine), Br (bromine), I (iodine), OH (hydroxyl), and $NH_2$ (amine). For example, $R_3$ can be selected from the group consisting of hydrogen, halogen, fluorine, cyano, $CF_3$, $OCF_3$, alkyl, methyl, substituted alkyl, halogen-substituted alkyl, hydroxyl-substituted alkyl, amine-substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NR_bR_c$. For example, $R_3$ can be selected from the group consisting of methyl and $C(R_8)_3$. Each $(R_8)$ can be independently selected from the group consisting of hydrogen, methyl, F (fluorine), Cl, Br, I, OH, and $NH_2$. For example, at most two of the independently selected $(R_1)$ substituents and the $(R_8)$ substituents can be selected to be F (fluorine), with the remainder being selected to be hydrogen.

In some embodiments, the compound of Formula I is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, an enantiomer, diastereomer, tautomer, and a salt or solvate thereof. For example, each $(R_1)$ can be selected to be hydrogen and $R_3$ can be selected to be methyl, so that the compound of Formula I is 2-acetylnaphtho[2,3-b]furan-4,9-dione. For example, each $R_a$ can be independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, and substituted aryl. For example, each $R_b$ and $R_c$ can be independently selected from the group consisting of, hydrogen, alkyl, substituted alkyl, cycloalkyl, substituted cycloalkyl, heterocycle, substituted heterocycle, aryl, and substituted aryl. Alternatively, an $R_b$ and $R_c$ together with the N to which they are bonded can form a heterocycle or substituted heterocycle.

Polymorphs

Naphthofuran compounds of the invention include polymorphs. In some embodiments, the polymorph is a polymorph of a compound according to Formula I. In some embodiments, the polymorph is a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399. This polymorph is referred to herein as "Crystal Form 1," "Form 1," or "XRPD1" and these terms are used interchangeably. In some embodiments, the polymorph is a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399. This polymorph is referred to herein as "Crystal Form 2," "Form 2," or "XRPD2" and these terms are used interchangeably. In some embodiments, the polymorph is a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399. This polymorph is referred to herein as "Crystal Form 3," "Form 3," or "XRPD3" and these terms are used interchangeably.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

Figure 7A:
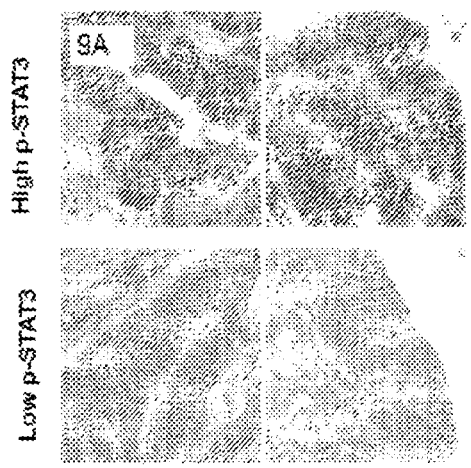
FIGS. 7A-7D show p-STAT3 and nuclear β-catenin as predicative biomarkers of practicing a method according to the invention.
Figure 7B:
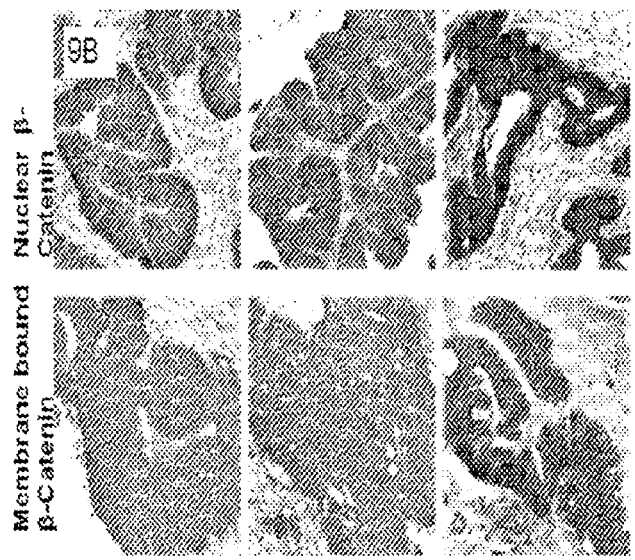
Figure 7C:
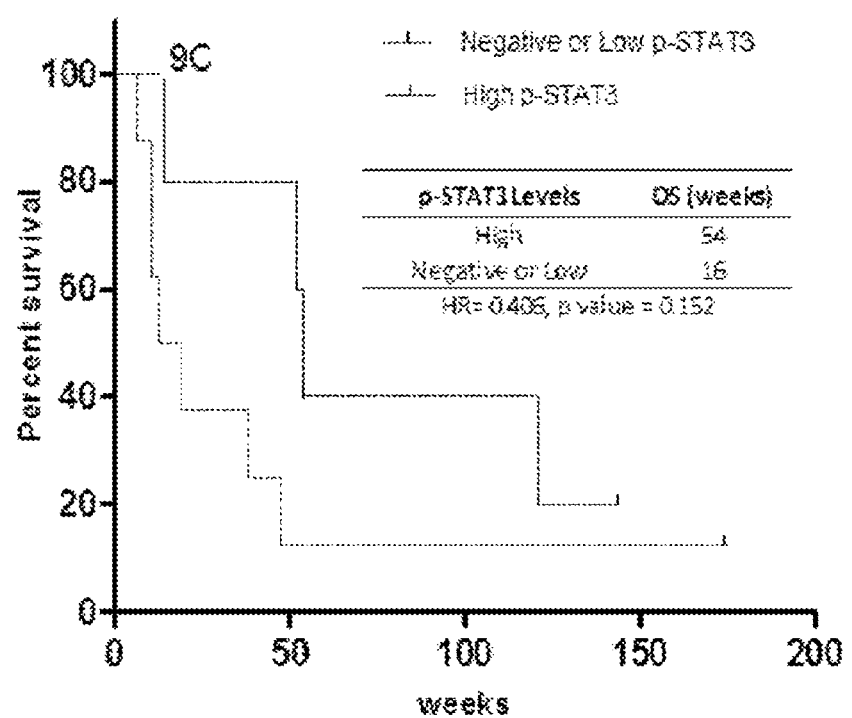
Figure 7D:
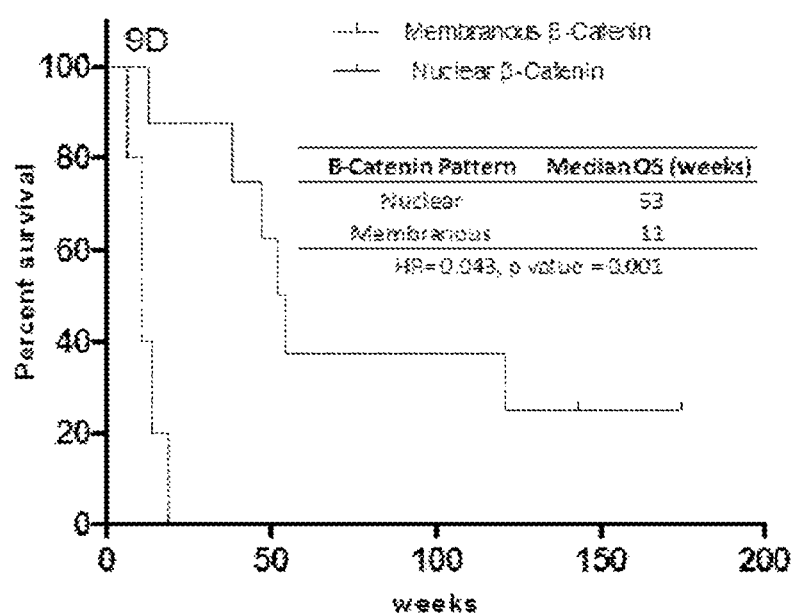

Crystal Form 3 has been shown to share a similar, but different, X-ray powder diffraction (XRPD) pattern as Form 1, and displayed very different crystalline habit than Form 1 (FIGS. 7A and B of WO 2011/116398 and WO 2011/116399). Form 3 can only be generated from Form 1 using a specially designed slurry process described herein. This polymorph has been successfully manufactured by a cGMP process and received approval from FDA and Health Canada to be used in clinical trials. Form 3 has also shown desirable pharmacokinetics (FIG. 12 of WO 2011/116398 and WO 2011/116399), safety.

The synthetic process for preparing Crystal Form 2 is shown in FIGS. 5A-5B of WO 2011/116398 and WO 2011/116399. Briefly, charged 3-butene-2-one (451.2 grams) is added to a 2 liter 3 neck round bottom flask equipped with a mechanical stirrer, thermometer, and addition funnel. To the addition funnel is added bromine (936.0 grams). After the contents in the flask have cooled to −5° C., the bromine is dropped into the flask with vigorous stirring and maintaining temperature at −5° C. over 30 minutes. The mixture is stirred for an additional 15 minutes at −5° C., and then is split into 4 equal portions. Each portion of the mixture along with tetrahydrofuran (2133.6 grams) is loaded into a 22 liter 4 neck round bottom flask equipped with a mechanical stirrer, thermometer, and addition funnel. Charged DBU (1,3-Diazabicyclo[5.4.0]undec-7-ene, 222.9 grams) is added to the addition funnel. The DBU is dropped into the flask with vigorous stirring and maintaining temperature at 0° C.-5° C. over 30 minutes. The mixture is stirred for an additional 15 min at 0° C.-5° C. 2-hydroxy-1,4-naphthoquinone (231 grams) is then added into the flask. Additional DBU (246.0 grams) is charged into the addition funnel and then dropped into the mixture in the flask at such a rate that the temperature of the reaction mixture does not exceed 40° C. After the addition of DBU is complete, the resulting mixture is stirred overnight at room temperature, and a sample of the reaction mixture is taken for HPLC analysis. To the reaction mixture, water (10.8 liters) is charged, and the resulting mixture is cooled to 0° C.-3° C. for at least 30 minutes, and then filtered via vacuum filter.

The filtered solid is rinsed with 5% aqueous sodium bicarbonate (3 liters), water (3 liters), 1% aqueous acetic acid (3 liters) and ethanol twice (2×1 liter) successively. The rinsed solid is stored and pooled together from other batches. The combined crude product (28.73 kg) is loaded along with ethyl acetate (811.7 kg) into a 500 gallon vessel equipped with a mechanical stirrer, thermometer, and a condenser. Under nitrogen atmosphere, the mixture is heated to reflux (72° C.) for 2 hours, and then filtered with a 10 micron cartridge filter containing an active carbon layer to remove insolubles. Fresh hot ethyl acetate (10 kg) is used to rinse the vessel, transfer line and filter. The combined filtrate is cooled to 0-5° C. and held at this temperature for 2 hours, and then is filtered with 20 inch Buchner filter. The filtered solid product is rinsed with 0-5° C. ethyl acetate (5.7 kg), and dried under vacuum at 40° C. to a constant weight. The remaining filtrate is reduced in volume by 63% by evaporation, and the crystallization process is repeated again to generate a second crop of product which was also dried under the same condition as the first crop of product. Both crops obtained are Crystal Form 2. The first crop produced (0.5 kg) had a 99.5% purity by HPLC (~95% by NMR). The second crop produced (1.09 kg) had a 98.9% purity by HPLC (~90% by NMR).

The synthetic process for preparing Crystal Form 3 is shown in FIGS. 6A-6D of WO 2011/116398 and WO 2011/116399. The steps are outlined briefly herein. Step 1: 3-Butene-2-one (methyl vinyl ketone, MVK) is brominated using bromine. No additional solvent is used. The intermediate 3,4-dibromobutan-2-one is dissolved in tetrahydrofuran (THF) and reacted with 1,8-diazabicyclo[5.4.0]undec-7-ene (DBU) to form a second intermediate, 3-bromo-3-buten-2-one. Once this reaction is complete, 2-hydroxy-1,4-naphthoquinone (HNQ) is added. A second portion of DBU is added, and the mixture is exposed to air. The reaction is quenched with water and the solids are collected by filtration. These solids are washed with aqueous sodium bicarbonate, aqueous acetic acid, water, and ethanol. The product is isolated by slurrying in ethanol and collecting the solids. Step 2: Residual amounts of the 2-acetyl-2,3-dihydronaphtho[2,3-b]furan-4,9-dione that accompany the desired 2-acetyl-4H,9H-naphtho[2,3-b]furan-4,9-dione (Compound 1) are oxidized to Compound 1 with activated manganese dioxide in toluene. The mixture is filtered through a cake of charcoal and Celite. The filtrate is concentrated to precipitate the product, which is filtered and dried. Step 3: The solids are slurried in ethyl acetate (25 mL/g purified Compound 1) at 75° C.-80° C. for about 5 hr, collected by filtration, and dried. Compound 1 produced with this method is Crystal Form 3. Compound 1 produced with this method without the slurry process yielded Crystal Form 1.

Effect of Compound Particle Size Distribution on Blood Plasma Drug Concentration Administering the naphthofuran compound in the form of particles having defined particle size, e.g., a reduced particle size, was found to enhance plasma drug concentration in vivo. Herein, unless otherwise noted, the terms "size" and "diameter" will be used interchangeably to describe particles. It is to be understood that the use of the term "diameter" does not necessarily imply that a particle has a perfectly or approximately spherical form. For example, "diameter" can be used as an approximation of the size of a particle, for example, the diameter of a sphere of equivalent volume to a non-spherical particle.

Herein, unless otherwise indicated, the term "blood plasma concentration", "blood molar concentration", and "blood concentration" are used interchangeably. The term "neoplasm" can be used to describe cells which exhibit an abnormal pattern of growth. Such a neoplasm can include tumors, both benign and malignant, e.g., solid tumors, as well as other cell growth disorders, such as leukemia, that have no defined shape and are not confined to a specific region of a human or animal body. Thus, "neoplasm" includes both cancerous and non-cancerous neoplastic cells and tissues. Herein, unless otherwise stated, made clear, or referring to a specific study or experiment, the terms "tumor" and "cancer" are to be understood as referring to the broader class of all neoplasms, including those that are not confined to a specific region of a human or animal body. However, the more limited term "solid tumor" is to be understood as not including cell growth disorders, such as leukemia, that have no defined shape and are not confined to a specific region of a human or animal body.

A neoplasm can exhibit none, one, or more than one of the following characteristics: solid form (a solid tumor), malignancy, metastasis, or Stat 3 pathway activity. A neoplasm can, for example, include a cancer stem cell. A neoplasm can be, for example, a carcinoma, sarcoma, adenocarcinoma, lymphoma, or a hematological malignancy.

Absorption has been defined as the process by which a drug is taken from the site of administration to the site of measurement within the body. See, M. Rowland, T. N. Tozer (1995) Clinical pharmacokinetics: Concepts and applications. Lippincott Williams & Wilkins. Oral drug absorption is often referred to as drug transfer across the apical membrane of the enterocyte, because the apical membrane is considered to be the rate limiting step for permeation of the membrane. See, U. Fagerholm & H. Lennemais (1995) Experimental estimation of the effective unstirred water layer thickness in the human jejunum, and its importance in oral drug absorption, Eur J Pharm Sci 3: 247-253; M. B. Lande, J. M. Donovan & M. L. Zeidel (1995) The relationship between membrane fluidity and permeabilities to water, solutes, ammonia, and protons, J Gen Physiol 106: 67-84. Permeability is a general term describing how readily the drug is transferred through a membrane. The specific permeability characteristics of a drug are dependent on its physico-chemical properties, including lipophilicity, charge, size, and polar surface area. See, Rowland & Tozer 1995; C. A. Lipinski, F. Lombardo, B. W. Dominy & P. J. Feeney (2001) Experimental and computational approaches to estimate solubility and permeability in drug discovery and development settings, Adv Drug Deliv Rev 46: 3-26. The rate of absorption is dependent on the permeability of the drug, surface area of the membrane, and the concentration gradient over the membrane. The concentration gradient is the driving force for passive diffusion, the most common mechanism for drug membrane transport. For oral administration, the drug is mainly absorbed by intestine. Human intestine is about 5-8 meters long and has a total surface area of almost 200 square meters while mouse intestine is only about 10-20 cm long. Therefore, one can predict that a drug with a larger particle size may have a higher or same absorption rate in human as a drug with a smaller particle size does in mouse, despite the permeability of the drug with a larger particle size being lower than that of the drug with a smaller particle size.

For example, a distribution of particle sizes of a compound according to Formula I, having a median diameter of less than or equal to about 200 μm, 150 μm, 100 μm, 80 μm, 60 μm, 40 μm, 20 μm, 10 μm, 5 μm, 4 μm, 3 μm, 2 μm, 1 μm, 0.5 μm or 0.2 μm can be predicted to result in a selective antitumor activity when administered in a pharmaceutical formulation, e.g., for the treatment of a cancer or tumor. For example, the distribution of particle sizes can be such that the particles have a median diameter of from about 0.02 μm to about 5 μm, or from about 0.2 μm to about 4 μm. For example, the distribution of particle sizes can be such that the particles have a median diameter of less than or equal to about 5 μm, a ratio of mean diameter over median diameter of at most about 2, and a ratio of mode diameter over median diameter of at least about 0.25.

The term "particle" can refer to an aggregate of a compound of Formula I. The term "mean" can refer to the sum of the sizes of all particles divided by the total number of particles. The term "median" can refer to, e.g., a diameter of which one-half of the particles have a greater diameter and one-half of the particles have a lesser diameter. The term "mode" can indicate the most frequently-occurring particle size value. The term "cumulative total" can refer to all particles.

The selective antitumor activity achieved by administration of the naphthofuran compound particles may depend not only on the size distribution of the particles, e.g., the volumes of particles or diameters representative of those volumes, but also on the shape and distribution of shapes of the particles. For example, a set of particles having a needle-like shape may result in a different pharmacokinetic profile than a set of particles having a spherical shape. Thus, it may be desirable to measure the shape and shape distribution of the particles to be administered and/or use a process that produces particles with predetermined shape and shape distribution, for example, a nearly uniform shape, e.g., the particles being approximations of spheres. For example, the sphericity, Ψ, of a particle can be defined as $$\Psi = \frac{\pi^{1/3}(6V_P)^{2/3}}{A_P},$$

where $V_p$ is the volume of the particle and $A_p$ is the surface area of the particle. A sphere has a sphericity of Ψ=1, and the closer the sphericity of a particle is to unity, the more closely the shape of the particle approximates a sphere. By way of comparison, a tetrahedron has a sphericity of about 0.671, a cube has a sphericity of about 0.806, an octahedron has a sphericity of about 0.846, a dodecahedron has a sphericity of about 0.910, and an icosahedron has a sphericity of about 0.939. Because the form of a sphere minimizes surface area for a given volume, a particle that is nearly spherical may be expected to dissolve more slowly than a particle of the same volume that is less nearly spherical. The mean sphericity of a set of spheres can be defined as $$\Psi_m = \frac{\pi^{1/3}(6\Sigma V_P)^{2/3}}{\Sigma A_P},$$

where $\Sigma V_p$ is the total volume of all the particles and $\Sigma A_p$ is the total surface area of all the particles. For example, particles of a compound according to Formula I administered may have a mean sphericity of at least about 0.8, or a mean sphericity of at least about 0.9.

The size, size distribution, shape, shape distribution, and factors such as surface roughness or irregularity of the particles can affect the mean specific surface area of the set of Compound 1 particles administered in a pharmaceutical formulation. The mean specific surface area can be defined as $\Sigma A_p/\Sigma m_p$, where $\Sigma A_p$ is the total surface area of the particles and $\Sigma m_p$ is the total mass of the particles. The greater the mean specific surface area of the particles, the faster the expected dissolution of the particles.

The particles of a compound according to Formula I in a pharmaceutical formulation can include the naphthofuran compound in a crystalline state across different particles or within the same particle. The crystalline state may include one or more polymorphs, across different particles or within the same particle. As will be appreciated by one of skill in the art, it is expected that the dissolution rate of the particles can be effected by the state of matter in the compound particles, for example, whether crystalline, of a first polymorph, or a second polymorph.

One or more of a range of techniques can be applied to determine the size and/or size distribution of particles of a compound according to Formula I in a pharmaceutical formulation. For example, sieve analysis, optical microscopic counting, electron micrograph counting, electroresistance counting, sedimentation time, laser diffraction, and/or acoustic spectroscopy can be applied. Some or all of these techniques or variations thereof can be applied to determine the shape, shape distribution, and/or specific area of the naphthofuran compound particles in a pharmaceutical formulation. A BET isotherm and/or air permeability specific surface technique can be applied to determine the specific area of particles of a compound according to Formula I in a pharmaceutical formulation.

Processes for Generating Naphthofuran Compounds

WO 2009/036099 and WO 2009/036101 disclose a process for the preparation of a naphthofuran compound of Formula II as follows.

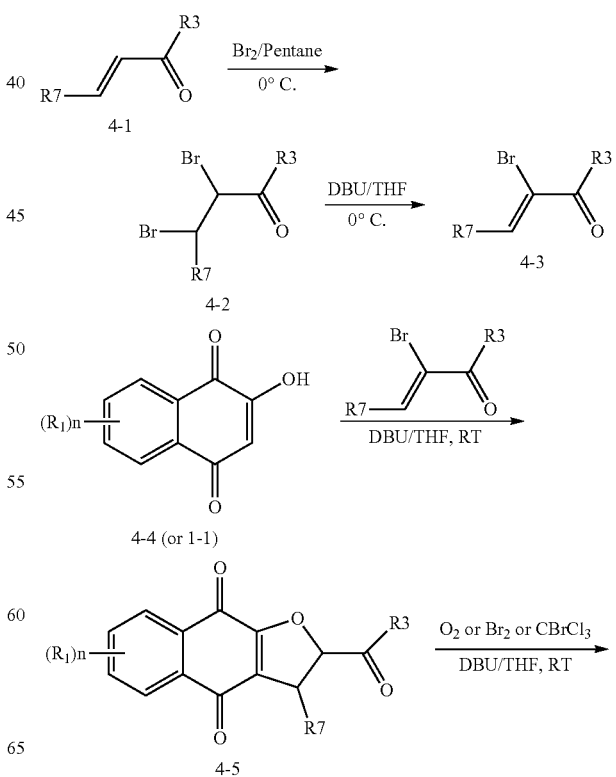

-continued

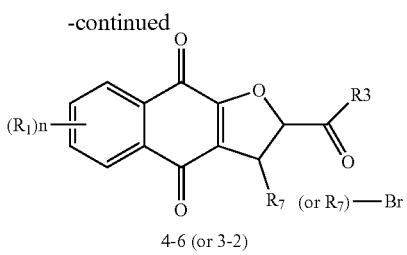

4-6 (or 3-2)

DBU: 1, 8-Diazabicyclo[5.4.0]undec-7-ene;
THF: Tetrahydrofuran;
RT: room temperature In this process, 3-bromo-3-buten-2-one (4-3) is reacted with 2-hydroxy-1,4-naphthoquinone (4-4) in an open air container, resulting in 2,3-dihydronaphtho[2,3-b]furan-4,9-dione (4-5). 2,3-dihydronaphtho[2,3-b]furan-4,9-dione (4-5) is oxidized by oxygen from open air to become naphtho[2,3-b]furan-4,9-dione (4-6). With naphtho[2,3-b]furan-4,9-dione produced by this process. However, during further development of the compound, it was determined that this process still generated significant various impurities which hinders the potential clinical applications of these compounds. In some embodiments, one of the impurities is 2,3-dihydronaphtho[2,3-b]furan-4,9-dione (4-5).

In one aspect, the present invention provides an improved process for the preparation of naphthofuran. The improved process minimizes the impurities, and thereby produces substantially pure naphthofuran. As used herein the term "substantially pure" refers to a preparation including at least about 80% or more, measured as % area HPLC, of the compound of the present invention. In some embodiments, the naphthofuran is naphtho[2,3-b]furan-4,9-dione and its related compounds (4-6).

In some embodiments, the process of the present invention includes one or more of the methods shown in the working examples provided herein. In some embodiments, the process includes one or more of the methods shown in Examples 1, 2 and/or 5 provided herein.

In some embodiments, the process of the present invention includes oxidizing the crude product of coupling of 3-bromo-3-buten-2-one (4-3) and 2-hydroxy-1,4-naphthoquinone (4-4) with an oxidizing agent in a first solvent. In a further embodiment, the oxidizing agent is manganese dioxide ($MnO_2$). In an even further embodiment, the crude product is isolated before it is oxidized. In some embodiments, the first solvent is toluene or chloroform.

In some embodiments, the process of the present invention further includes treating the aged oxidation mixture with charcoal to get rid of certain impurities. In a further embodiment, the aged oxidation mixture is filtered with a pad of activated carbon. In an even further embodiment, the mixture is filtered at around 100° C.

In some embodiments, the process of the present invention further includes crystallizing the product from the filtrate. In a further embodiment, the product is crystallized by concentrating the filtrate with evaporation, and cooling down.

In some embodiments, the process of the present invention further includes re-crystallizing the product with a second solvent. In a further embodiment, the second solvent is ethyl acetate.

In an alternative embodiment, the process of the present invention further includes slurrying in a second solvent the product crystallized from the first solvent, heating the slurry, and cooling the slurry. In a further embodiment, the second solvent is ethyl acetate. In some embodiments, the product is slurried and heated only to partial dissolution. In a further embodiment, the volume of the second solvent used to slurry the product is about 1/10, 1/5, 1/4, 1/3, 1/2, or 2/3 of the volume for the complete dissolution of the product in the heated condition.

The present invention also provides a naphthofuran compound prepared by the process of the present invention. In some embodiments, the naphthofuran compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In a further embodiment, the naphthofuran compound is prepared by the process including reacting the isolated crude product of the coupling of 2-hydroxy-1,4-naphthoquinone (4-4) and 3-Bromo-3-buten-2-one (4-3) with manganese dioxide in the presence of toluene. In an even further embodiment, the process further includes filtering the aged reaction mixture with a pad of activated carbon.

In another aspect, the present invention provides substantially pure naphthofuran compounds.

In some embodiments, the present invention provides a substantially pure compound selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof.

In some embodiments, the present invention provides a substantially pure compound of Formula II,

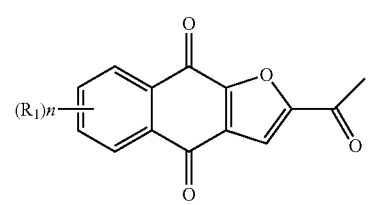

(II)

wherein each $R_1$ is independently H, Cl, or F; and n is 0, 1, 2, 3, or 4.

As used herein, "substantially pure" refers to a purity of at least about 80%. In some embodiments, the purity of a compound of the present invention has a purity of at least about 85%, about 90%, about 95%, or about 99%. In a further embodiment, the purity of a compound of the present invention has a purity of at least about 99.5%, or about 99.8%. In an even further embodiment, the purity of a compound of the present invention has a purity of at least about 99.85%, about 99.90%, about 99.94%, about 99.95%, or about 99.99%. In some embodiments, the compound of the present invention is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the compound of the present invention is a polymorph. In some embodiments, the compound of the present invention is a polymorph of a compound according to Formula I. In some embodiments, the compound of the present invention is a polymorph of Compound 1.

The typical impurities that may be present in a compound of the present invention include one or more selected from the group consisting of by-product, isomer, intermediate, and solvent. In some embodiments, the impurities that may be present in a compound of the present invention is at most about 10%, about 8%, about 5%, about 2%, or about 1% relative to the compound of Formula II. In a further embodiment, the impurities that may be present in a compound of the present invention is at most about 0.5%, about 0.2%, about 0.15%, or about 0.1% relative to the compound of Formula II. In an even further embodiment, the impurities that may be present in a compound of the present invention is at most about 0.05%, about 0.02%, or about 0.01% relative to the compound of Formula II. In some embodiments, the substantially pure compound of Formula II have at most about 500, 200, 100, 50, 20, 10, 5, 2, 1, 0.5, 0.2, 0.15, 0.1, or 0 parts per million (p.p.m.) of residual by-product or by-products relative to the compound of Formula II.

In some embodiments, the impurities include one or more by-products selected from the group consisting of 2-acetyl-2,3-dihydronaphtho[2,3-b]furan-4,9-dione, 2,6-Diacetyl-naphtho[2,3-b]furan-4,9-dione, 2,7-Diacetyl-naphtho[2,3-b]furan-4,9-dione, 3-Acetyl-naphtho[2,3-b]furan-4,9-dione, Naphtho[2,3-b]furan-4,9-dione, Naphtho[2,3-b]furan-4,9-dione, Naphtho[2,3-b]furan-4,9-diol, and 1-(4,9-Dihydroxy-naphtho[2,3-b]furan-2-yl)-ethanone.

In some embodiments, the impurities include manganese (Mn).

The purity of a compound of the present invention may be determined with various devices. In some embodiments, the purity is determined with HPLC (High Performance Liquid Chromatography). In some embodiments, the purity is determined with NMR (Nuclear Magnetic Resonance). In a further embodiment, the purity is determined with HPLC and NMR.

These highly pure compositions containing Compound 1 exhibit a significantly improved safety profile in animal experiments compared to less pure compositions that contain Compound 1. No signs of any adverse effects of highly pure Compound 1 have been observed in mice. In addition, these highly pure compositions containing Compound 1 have been tested in patients and have demonstrated exceptional safety. For example, FIG. 13 of WO 2011/116398 and WO 2011/116399 illustrates the toxicity observed with a composition with about 90% purity for Compound 1, while FIG. 14 of WO 2011/116398 and WO 2011/116399 illustrates that the highly pure compositions having about 95% or greater purity for Compound 1 are safe and effective. In a Phase 1 study, the dose of Compound 1 was escalated from 20 mg to 2000 mg/day, and a maximum tolerated dose (MTD) not reached. No dose-limiting toxicity was observed. Patients tolerated Compound 1 very well without drug-induced adverse effects, which is in sharp contrast to cancer chemotherapeutics. The clinical safety profile of the substantially pure compositions of Compound 1 is among the best for oncology drugs in history.

Pharmaceutical Formulations

Certain excipients or enhancers were found to enhance the oral bioavailability of particles of a compound according to Formula I of a given particle size distribution in a pharmaceutical formulation. For example, the addition of the pharmaceutically compatible excipient GELUCIRE™ 44/14 (a polyethylene glycol glyceryl laurate produced by Gattefossé) can increase the bioavailability of Compound 1 having a median particle size of less than or equal to about 20 microns. Examples of other excipients that can be used to enhance or control oral bioavailability include surfactants, such as TWEEN 80™ or TWEEN 20™ (a polysorbate, i.e., a polyoxyethylene sorbitan monolaurate) or certain lipids, such as phosphatidylcholines, e.g., dimyristoylphosphatidylcholine (DMPC). Surfactants include compounds that are amphiphilic and contain both hydrophobic and hydrophilic groups. Other excipients can include, for example, a glycerol ester of a fatty acid, a glycerol ester of a saturated fatty acid, a glycerol ester of a saturated fatty acid having from 8 to 18 carbons, glyceryl laurate, polyethylene glycol, a polyoxyethylene sorbitan alkylate, cellulose or cellulose derivatives, such as microcrystalline cellulose and carboxymethyl cellulose (CMC), as well as lipids, such as sterols, e.g., cholesterol. Other excipients can include antioxidants, such as Vitamin E. Other excipients and additional components can be included in a pharmaceutical formulation according to the present invention, as will be appreciated by one of skill in the art. For example, other active agents, standard vehicles, carriers, liquid carriers, saline, aqueous solutions, diluents, surface active agents, dispersing agents, inert diluents, granulating and disintegrating agents, binding agents, lubricating agents, glidants, discharging agents, sweetening agents, flavoring agents, coloring agents, preservatives, physiologically degradable compositions such as gelatin, aqueous vehicles and solvents, oily vehicles and solvents, suspending agents, dispersing or wetting agents, suspending agents, emulsifying agents, demulcents, buffers, salts, thickening agents, gelatins, fillers, emulsifying agents, antioxidants, antibiotics, antifungal agents, stabilizing agents, water, glycols, oils, alcohols, crystallization retarding agents (e.g., to retard crystallization of a sugar), starches, sugars, sucrose, surface active agents, agents to increase the solubility of any other ingredient, such as a polyhydroxy alcohol, for example glycerol or sorbitol, pharmaceutically acceptable polymeric or hydrophobic materials, and other components can be included. The appropriate additional agent or agents to add will depend on the dosage form (e.g., injectable solution, capsule, or pill), as will be appreciated by one skilled in the art.

The compound according to Formula I of the present invention may be formulated into "pharmaceutical compositions". Embodiments according to the present invention include various dosage forms including a compound, which can be useful, for example, for treating a patient. For example, oral dosage forms can include a tablet, pill, capsule (hard or soft), caplet, powder, granule, suspension (e.g., in an aqueous or oily vehicle), solution (e.g., in an aqueous or oily vehicle), gel, cachet, troche, lozenge, syrup, elixir, emulsion, draught, oil-in-water emulsion, or a water-in-oil emulsion. Because of their ease in administration, tablets and capsules may represent a preferred oral dosage. Solid oral dosage forms may be sugar coated or enteric coated by standard techniques. For example, nasal and other mucosal spray formulations (e.g. inhalable forms) can include purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier, of an inhalant, or of an aerosol. Such formulations may be delivered by any suitable means or method, e.g., by nebulizer, atomizer, metered dose inhaler, or the like. For example, a pharmaceutical composition according to the present invention may be administered topically, for example, in the form of an ointment, cream, or suppository. For example, a pharmaceutical composition according to the present invention may be administered by injecting an injectant. Thus, a dosage form according to the present invention can have, for example, a solid, semi-solid, liquid, or gaseous form. Suitable dosage forms include but are not limited to oral, rectal, sub-lingual, mucosal, nasal, ophthalmic, subcutaneous, intramuscular, intravenous, parenteral, transdermal, spinal, intrathecal, intra-articular, intra-arterial, sub-arachinoid, bronchial, lymphatic, and intra-uterile administration, and other dosage forms for systemic delivery of active ingredients. An active ingredient, for example, a compound according to Formula I may be contained in a formulation that provides quick release, sustained release, delayed release, or any other release profile known to one skilled in the art after administration to a subject (patient). The mode of administration and dosage form selected for a given treatment is closely related to the therapeutic amounts of the compounds or compositions which are desirable and efficacious for the given treatment application as well as factors such as the mental state and physical condition of the subject (patient).

A pharmaceutical composition of the invention may be prepared, packaged, or sold in bulk, as a single unit dose, as a plurality of single unit doses, or in a multi-dose form. As used herein, a "unit dose" is a discrete amount of the pharmaceutical composition including a predetermined amount of the active ingredient. The amount of the active ingredient in each unit dose is generally equal to the total amount of the active ingredient that would be administered or a convenient fraction of a total dosage amount such as, for example, one-half or one-third of such a dosage. A formulation of a pharmaceutical composition of the invention suitable for oral administration may be in the form of a discrete solid dosage unit. Each solid dosage unit contains a predetermined amount of the active ingredient, for example a unit dose or fraction thereof. As used herein, an "oily" liquid is one which includes a carbon or silicon based liquid that is less polar than water. In such pharmaceutical dosage forms, the active agent preferably is utilized together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof. The compositions of the present invention can be provided in unit dosage form, wherein each dosage unit, e.g., a teaspoon, tablet, capsule, solution, or suppository, contains a predetermined amount of the active drug or prodrug, alone or in appropriate combination with other pharmaceutically active agents. The term "unit dosage form" refers to physically discrete units suitable as unitary dosages for human and animal subjects, each unit containing a predetermined quantity of the composition of the present invention, alone or in combination with other active agents, calculated in an amount sufficient to produce the desired effect.

Dosage forms of the present pharmaceutical composition can be prepared by techniques known in the art and contain a therapeutically effective amount of an active compound or ingredient. Any technique known or hereafter developed may be used for the preparation of pharmaceutical compositions or formulations according to the invention. In general, preparation includes bringing the active ingredient into association with a carrier or one or more other additional components, and then, if necessary or desirable, shaping or packaging the product into a desired single- or multi-dose unit. Powdered and granular formulations according to the invention may be prepared using known methods or methods to be developed. Such formulations may be administered directly to a subject, or used, for example, to form tablets, fill capsules, or prepare an aqueous or oily suspension or solution by addition of an aqueous or oily vehicle thereto. A tablet may be made by compression or molding, or by wet granulation, optionally with one or more accessory ingredients. Compressed tablets may be prepared by compressing, in a suitable device, the active ingredient in a free-flowing form such as a powder or granular preparation. Molded tablets may be made by molding, in a suitable device, a mixture of the active ingredient, a pharmaceutically acceptable carrier, and at least sufficient liquid to moisten the mixture. Tablets may be non-coated, or they may be coated using methods known in the art or methods to be developed. Coated tablets may be formulated for delayed disintegration in the gastrointestinal tract of a subject, for example, by use of an enteric coating, thereby providing sustained release and absorption of the active ingredient. Tablets may further include ingredients to provide a pharmaceutically elegant and palatable preparation. Hard capsules including the active ingredient may be made using a physiologically degradable composition, such as gelatin. Such hard capsules include the active ingredient. Soft gelatin capsules including the active ingredient may be made using a physiologically degradable composition, such as gelatin. Such soft capsules include the active ingredient, which may be mixed with water or an oil medium. Liquid formulations of a pharmaceutical composition of the invention that are suitable for administration may be prepared, packaged, and sold either in liquid form or in the form of a dry product intended for reconstitution with water or another suitable vehicle prior to use. Liquid suspensions, in which the active ingredient is dispersed in an aqueous or oily vehicle, and liquid solutions, in which the active ingredient is dissolved in an aqueous or oily vehicle, may be prepared using conventional methods or methods to be developed. Liquid suspension of the active ingredient may be in an aqueous or oily vehicle. Liquid solutions of the active ingredient may be in an aqueous or oily vehicle. To prepare such pharmaceutical dosage forms, an active ingredient, e.g., a naphthofuran, can be intimately admixed with a pharmaceutical carrier according to conventional pharmaceutical compounding techniques. The carrier may take a wide variety of forms depending on the form of preparation desired for administration. In preparing the compositions in oral dosage form, any of the usual pharmaceutical media may be employed.

In some embodiments according to the present invention, an item of manufacture includes a container containing a therapeutically effective amount of a pharmaceutical composition including a compound according to Formula I. The container can include a pharmaceutically acceptable excipient. The container can include printed labeling instructions. For example, the printed labeling can indicate the dosage and frequency with which the pharmaceutical composition should be administered, and whether the composition should be administered with food or within a defined period of time before or after ingestion of food. The composition can be contained in any suitable container capable of holding and dispensing the dosage form that will not significantly interact with the composition. The labeling instructions can be consistent with the methods of treatment described herein. The labeling can be associated with the container by a means that maintains a physical proximity of the two. By way of non-limiting example, the container and the labeling may both be contained in a packaging material such as a box or plastic shrink wrap or may be associated with the instructions being bonded to the container such as with glue that does not obscure the labeling instructions or other bonding or holding means.

In some embodiments of the invention, a pharmaceutical composition includes a therapeutically effective amount of an active ingredient that is a Compound of the Invention, e.g., (a) a compound according to Formula I, b) polyoxylglycerides of which hydrophilic-lipophilic balance (HLB) is more than 10, and (c) polyoxylglycerides of which HLB is less than 10. More preferably, a pharmaceutical composition further comprising (d) a surfactant.

Preferable examples of the polyoxylglycerides of which HLB is more than 10 include the one of which HLB is between 10 and 17, more preferably the one of which HLB is between 12 and 15. Further preferable examples include the one that is solid or semi-solid at 25 degrees Celsius, preferably the one of which melting point is more than 30 degrees Celsius, more preferably the one of which melting point is between 33-64 degrees Celsius, even more preferably the one of which melting point is between 40-55 degree Celsius. Specific example includes lauroyl polyoxylglycerides, more specifically lauroyl polyoxyl-32 glycerides, such as Gelucire™44/14, and stearoyl polyoxylglycerides, more specifically stearoyl polyoxyl-32 glycerides, such as Gelucire™50/13 are preferred. More preferable specific examples include lauroyl polyoxylglycerides, more specifically lauroyl polyoxyl-32 glycerides, such as Gelucire™44/14.

Preferable examples of the polyoxylglycerides of which HLB is less than 10 include the one of which HLB is between 2 and 8, more preferably the one of which HLB is between 3 and 7. Specific examples include linoleoyl polyoxylglycerides, such as Labrafil™ M2125CS, leoyl polyoxylglycerides, such as Labrafil™ M1944CS, and lauroyl polyoxyl-6 glycerides, such as Labrafil™ M2130CS. More preferable specific examples include linoleoyl polyoxylglycerides, and oleoyl polyoxylglycerides.

Examples of a surfactant includes sodium lauryl sulfate (SLS) or sodium dodecyl sulfate (SDS), polyoxyethylene sorbitan monolaurate (a polysorbate, preferably TWEEN 80™ or TWEEN 20™), certain lipids, such as phosphatidylcholines, e.g., dimyristoylphosphatidylcholine (DMPC). Surfactants include compounds that are amphiphilic and contain both hydrophobic and hydrophilic groups. Preferable surfactant is sodium lauryl sulfate (SLS) or sodium dodecyl sulfate (SDS).

The active ingredient may be included in the range from 5% to 50% for a weight of formulation. The surfactant may be included in the range from 0.05% to 5% for a weight of formulation. The polyoxylglycerides of which HLB is more than 10 may be included in the range from 5% to 80% for a weight of formulation. The polyoxylglycerides of which HLB is less than 10 may be included in the range from 5% to 80% for a weight of formulation. The ratios between the polyoxylglycerides of which HLB is more than 10 and the polyoxylglycerides of which HLB is less than 10 is from about 90/10 to about 10/90. Preferably, the ratio is from about 80/20 to about 20/80, more preferably, is from about 40/60 to about 80/20. The composition may consist of, by weight, about 27.18% in the active ingredient, about 0.27% in the surfactant, about 14.51% in the polyoxylglycerides of which HLB is more than 10, and about 58.04% in the polyoxylglycerides of which HLB is less than 10. A 125 mg capsule embodiment may consist of 125 mg of the active ingredient, about 1.2 mg of the surfactant, about 66.8 mg of the polyoxylglycerides of which HLB is more than 10, and about 267 mg of the polyoxylglycerides of which HLB is less than 10. An 80 mg capsule embodiment may consist of about 80 mg of the active ingredient, about 0.8 mg of the surfactant, about 42.7 mg of the polyoxylglycerides of which HLB is more than 10, and about 170.9 mg of the polyoxylglycerides of which HLB is less than 10. Embodiments of the invention include items of manufacture where any of the above pharmaceutical compositions is housed in a capsule, e.g., a LIcap capsule. The capsule is preferable of size 1 or smaller, e.g., size 2.

Processes for Making Pharmaceutical Formulations Having Selected Particle Size Distribution and Identifying an Optimum Particle Size Distribution Milling Processes In a method according to the present invention, a milling or grinding process can be used to reduce the size of particles of an active ingredient or compound according to Formula I. For example, a milling or grinding process can be suitable for producing particles having a median size of 200 µm, 150 µm, 100 µm, 40 µm, 20 µm, 5 µm, 2 µm or greater or lesser size. Such a milling or grinding process can include, for example, ball milling, roll milling, jet milling, wet milling, ultrasonic milling, grinding, and combinations. For example, the process can reduce particle size by impacting particles with a hard surface, or by subjecting the particles to high pressure, e.g., squeezing a particle between two surfaces. For example, in jet milling, a stream of gas entrains particles and accelerates them to high velocities. The particles then impact other particles and walls and fracture into smaller particles. For example, in wet milling, particles are combined with a liquid, and the resultant slurry is passed through a high shear mixer to fracture the particles. For example, in ultrasonic milling, particles, for example, in a slurry, are exposed to ultrasonic radiation. Cavitation induced by the ultrasound can fracture the particles into particles of smaller size.

It can be advantageous to lower the temperature of the particles prior to subjecting them to the milling or grinding operation. For example, the temperature can be lowered to a cryogenic temperature, e.g., by exposing the particles to or immersing the particles in a cryogenic fluid, such as liquid nitrogen. Such lowering of the temperature can render the particles more brittle and more susceptible to having their size reduced in the milling or grinding operation. Subsequent to the milling or grinding process, a selection process, such as sieving, can be used to narrow the range of particle sizes.

Crystallizing Process

Crystallization is the main separation and purification step for the manufacturing of drug substances. Crystallization can also be utilized to control particle size. The particle size distribution (PSD) obtained during crystallization is influenced by a combination of various mechanisms that occur during crystallization, such as nucleation, growth, aggregation, attrition, breakage, etc. Control of PSD during crystallization is critical to achieving the desired product properties. When the particle size cannot be consistently controlled during crystallization to meet the desired specifications, an extra processing step such as dry milling can be included. (Braat, et al Crystallization: Particle Size Control, *Encyclopedia of Pharmaceutical Technology: Third Edition*, Published on 2 Oct. 2006)

Methods for Treatment of Cancer

A method according to the present invention for treating, delaying the progression of, preventing a relapse of, alleviating a symptom of, or otherwise ameliorating a human, mammal, or animal subject afflicted with a neoplasm includes administering a therapeutically effective amount of a pharmaceutical composition including particles of a predetermined size distribution, for example, a compound according to Formula I such as Compound 1, a pure compound, a pure product and/or a pure pharmaceutical composition, so that the volume growth of the neoplasm is slowed, the volume growth of the neoplasm is stopped, the neoplasm decreases in volume, and/or a cancerous neoplasm is killed. A few examples of types of neoplasms that may be amenable to treatment by this method include solid tumors, malignant tumors, cancers, refractory cancers, recurrent cancers, metastatic tumors, neoplasms including cancer stem cells, neoplasms in which the STAT3 pathway is implicated, carcinomas, and sarcomas. In some embodiments, the cancers that may be amenable to treatment by administration of particles of a compound according to Formula I are selected from the group consisting of esophageal cancer, gastroesophageal junction cancer, gastroesophageal adenocarcinoma, colorectal cancer, colon adenocarcinoma, rectal adenocarcinoma, colorectal adenocarcinoma, breast cancer, ovarian cancer, head and neck cancer, melanoma, chondrosarcoma, gastric adenocarcinoma, and adrenocorticoid. The STAT3 pathway may be implicated in these cancers. The CSC pathway may be implicated in these cancers.

In embodiments of the invention, a therapeutically effective amount of the Compound of the Invention or a pharmaceutically acceptable salt, solvate, hydrate, or prodrug thereof is administered to a patient or subject diagnosed of a cancer, wherein the cancer is gastroesophageal junction cancer, an esophageal cancer, or gastroesophageal adenocarcinoma. Optionally, an antimitotic agent such as paclitaxel is administered as a second/combinatorial agent for co-therapy. In one feature, the Compound of the Invention is administered to the subject in two daily doses totaling in a range from about 160 mg to about 1000 mg, preferably BID with an interval between administrations of the Compound in the range from about 4 hours to about 16 hours, more preferably of about 12 hours. The optional co-agent paclitaxel can be administered to the subject at a total weekly dose in a range from about 40 mg/m$^2$ to about 100 mg/m$^2$, e.g., at about 80 mg/m$^2$.

Cancer Stem Cells

In recent years, a new model of tumorigenesis has gained wide acceptance, where it is hypothesized that only a small fraction of the entire tumor mass are responsible for the tumorigenic activities within the tumor, whereas the old or clonal genetic model posits that all the mutated tumor cells contribute equally to such tumorigenic activities. This small fraction of tumorigenic cells, according to the new model, is transformed cells with stem-cell-like qualities and is called "cancer stem cells" (CSCs). Bonnet and Dick first demonstrated, in vivo, the presence of CSCs in acute myeloid leukemia (AML) during the 1990s. Their data showed that only a small subpopulation of human AML cells had the ability to transfer AML when transplanted into immunodeficient mice while other AML cells were incapable of inducing leukemia. Later, these CSCs were shown to have the same cellular markers, CD34$^+$/CD38$^-$, as primitive hematopoietic stem cells. (Bonnet, D., *Normal and leukaemic stem cells*. Br J Haematol, 2005. 130(4): p. 469-79). Since then, researchers have found CSCs conclusively in various types of tumors including those of the brain, breast, skin, prostate, colorectal cancer, and so on.

The CSC model of tumorigenesis would explain why tens or hundreds of thousands of tumor cells need to be injected into an experimental animal in order to establish a tumor transplant. In human AML, the frequency of these cells is less than 1 in 10,000. (Bonnet, D. and J. E. Dick, *Human acute myeloid leukemia is organized as a hierarchy that originates from a primitive hematopoietic cell*. Nat Med, 1997. 3(7): p. 730-7). Even though rare within a given tumor cell population, there is mounting evidence that such cells exist in almost all tumor types. However, as cancer cell lines are selected from a sub-population of cancer cells that are specifically adapted to grow in tissue culture, the biological and functional properties of cancer cell lines can undergo dramatic changes. Therefore, not all cancer cell lines contain CSCs.

Cancer stem cells share many similar traits with normal stem cells. For example, CSCs have self-renewal capacity, namely, the ability to give rise to additional tumorigenic cancer stem cells, typically at a slower rate than other dividing tumor cells, as opposed to a limited number of divisions. CSCs also have the ability to differentiate into multiple cell types, which would explain histological evidence that not only many tumors contain multiple cell types native to the host organ, but also that heterogeneity is commonly retained in tumor metastases. CSCs have been demonstrated to be fundamentally responsible for tumorigenesis, cancer metastasis, and cancer reoccurrence. CSCs are also called tumor initiating cells, cancer stem-like cells, stem-like cancer cells, highly tumorigenic cells, tumor stem cells, solid tumor stem cells, or super malignant cells.

The existence of cancer stem cells has fundamental implications for future cancer treatments and therapies. These implications are manifested in disease identification, selective drug targeting, prevention of cancer metastasis and recurrence, and development of new strategies in fighting cancer.

The efficacy of current cancer treatments is, in the initial stages of testing, often measured by the size of the tumor shrinkage, i.e., the amount of tumor mass that is killed off. As CSCs would form a very small proportion of the tumor and have markedly different biologic characteristics than their more differentiated progenies, the measurement of tumor mass may not necessarily select for drugs that act specifically on the stem cells. In fact, cancer stem cells appear to be resistant to radiotherapy (XRT) and also refractory to chemotherapeutic and targeted drugs. (Hambardzumyan, D., M. Squatrito, and E. C. Holland, Radiation resistance and stem-like cells in brain tumors. Cancer Cell, 2006. 10(6): p. 454-6; Baumann, M., M. Krause, and R. Hill, Exploring the role of cancer stem cells in radioresistance. Nat Rev Cancer, 2008. 8(7): p. 545-54; Ailles, L. E. and I. L. Weissman, Cancer stem cells in solid tumors. Curr Opin Biotechnol, 2007. 18(5): p. 460-6). Normal somatic stem cells are naturally resistant to chemotherapeutic agents—they have various pumps (such as MDR) that pump out drugs, and DNA repair proteins. Further, they also have a slow rate of cell turnover while chemotherapeutic agents target rapidly replicating cells. Cancer stem cells, being the mutated counterparts of normal stem cells, may also have similar mechanisms that allow them to survive drug therapies and radiation treatment. In other words, conventional chemotherapies and radiotherapies kill differentiated or differentiating cells, which form the bulk of the tumor that are unable to generate new highly tumorigenic cancer stem cells. The population of cancer stem cells that gave rise to the differentiated and differentiating cells, on the other hand, could remain untouched and cause a relapse of the disease. A further danger for conventional anti-cancer therapy is the possibility that chemotherapeutic treatment leaves only chemotherapy-resistant cancer stem cells, and the ensuing recurrent tumor will likely also be resistant to chemotherapy.

Since the surviving cancer stem cells can repopulate the tumor and cause relapse, it is imperative that anti-cancer therapies include strategies against CSCs (see FIG. 18 of WO 2011/116398 and WO 2011/116399). This is akin to eliminating the roots in order to prevent dandelions from regrowth even if the weed's ground level mass has been cut. (Jones, R. J., W. H. Matsui, and B. D. Smith, *Cancer stem cells: are we missing the target?* J Natl Cancer Inst, 2004. 96(8): p. 583-5). By selectively targeting cancer stem cells, it becomes possible to treat patients with aggressive, non-resectable tumors and refractory or recurrent cancers, as well as preventing the tumor metastasis and recurrence. Development of specific therapies targeting cancer stem cells may improve survival and the quality of life of cancer patients, especially for sufferers of metastatic cancers. The key to unlocking this untapped potential is the identification and validation of pathways that are selectively important for cancer stem cell self-renewal and survival. Unfortunately, though multiple pathways underlying tumorigenesis in cancer or self-renewal in embryonic and adult stem cells have been elucidated in the past, very few pathways have been identified and validated for cancer stem cell self-renewal and survival.

There has also been a lot of research into the identification and isolation of cancer stem cells. Methods used mainly exploit the ability of CSCs to efflux drugs, or are based on the expression of surface markers associated with cancer stem cells.

For example, since CSCs are resistant to many chemotherapeutic agents, it is not surprising that CSCs almost ubiquitously overexpress drug efflux pumps such as ABCG2 (BCRP-1) (Ho, M. M., et al., Side population in human lung cancer cell lines and tumors is enriched with stem-like cancer cells. Cancer Res, 2007. 67(10): p. 4827-33; Wang, J., et al., Identification of cancer stem cell-like side population cells in human nasopharyngeal carcinoma cell line. Cancer Res, 2007. 67(8): p. 3716-24; Haraguchi, N., et al., Characterization of a side population of cancer cells from human gastrointestinal system. Stem Cells, 2006. 24(3): p. 506-13; Doyle, L. A. and D. D. Ross, Multidrug resistance mediated by the breast cancer resistance protein BCRP (ABCG2). Oncogene, 2003. 22(47): p. 7340-58; Alvi, A. J., et al., Functional and molecular characterisation of mammary side population cells. Breast Cancer Res, 2003. 5(1): p. R1-8), and other ATP binding cassette (ABC) superfamily members (Frank, N.Y., et al., ABCB5-mediated doxorubicin transport and chemoresistance in human malignant melanoma. Cancer Res, 2005. 65(10): p. 4320-33; Schatton, T., et al., Identification of cells initiating human melanomas. Nature, 2008. 451(7176): p. 345-9). Accordingly, the side population (SP) technique, originally used to enrich hematopoietic and leukemic stem cells, was also employed to identify and isolate CSCs. (Kondo, T., T. Setoguchi, and T. Taga, *Persistence of a small subpopulation of cancer stem-like cells in the C6 glioma cell line*. Proc Natl Acad Sci USA, 2004. 101(3): p. 781-6). This technique, first described by Goodell et al., takes advantage of differential ABC transporter-dependent efflux of fluorescent dyes such as Hoechst 33342 to define and isolate a cell population enriched in CSCs (Doyle, L. A. and D. D. Ross, *Multidrug resistance mediated by the breast cancer resistance protein BCRP (ABCG2)*. Oncogene, 2003. 22(47): p. 7340-58; Goodell, M. A., et al., *Isolation and functional properties of murine hematopoietic stem cells that are replicating in vivo*. J Exp Med, 1996. 183(4): p. 1797-806). Specifically, the SP is revealed by blocking drug efflux with verapamil, at which point the dyes can no longer be pumped out of the SP.

Researchers have also focused on finding specific markers that distinguish cancer stem cells from the bulk of the tumor. Most commonly expressed surface markers by the cancer stem cells include CD44, CD133, and CD166. (Collins, A. T., et al., Prospective identification of tumorigenic prostate cancer stem cells. Cancer Res, 2005. 65(23): p. 10946-51; Li, C., et al., Identification of pancreatic cancer stem cells. Cancer Res, 2007. 67(3): p. 1030-7; Ma, S., et al., Identification and characterization of tumorigenic liver cancer stem/progenitor cells. Gastroenterology, 2007. 132(7): p. 2542-56; Prince, M. E., et al., Identification of a subpopulation of cells with cancer stem cell properties in head and neck squamous cell carcinoma. Proc Natl Acad Sci USA, 2007. 104(3): p. 973-8; Ricci-Vitiani, L., et al., Identification and expansion of human colon-cancer-initiating cells. Nature, 2007. 445(7123): p. 111-5; Singh, S. K., et al., Identification of a cancer stem cell in human brain tumors. Cancer Res, 2003. 63(18): p. 5821-8; Dalerba, P., et al., Phenotypic characterization of human colorectal cancer stem cells. Proc Natl Acad Sci USA, 2007. 104(24): p. 10158-63). Sorting tumor cells based primarily upon the differential expression of these surface marker(s) have accounted for the majority of the highly tumorigenic CSCs described to date. Therefore, these surface markers are well validated for identification and isolation of cancer stem cells from the cancer cell lines and from the bulk of tumor tissues.

Recent studies have uncovered the presence of cancer stem cells (CSCs) with an exclusive ability to regenerate tumors. These CSCs exist in almost all tumor types and are functionally linked with continued malignant growth, cancer metastasis, recurrence, and cancer drug resistance. CSCs and their more differentiated progenies appear to have markedly different biologic characteristics. Conventional cancer drug screenings depend on measurement of the amount of tumor mass, therefore, they may not necessarily select for drugs that act specifically on the CSCs. In fact, CSCs have been demonstrated to resistant to standard chemotherapies and radiotherapy, and to becoming enriched after standard anti-cancer treatments, which result in cancer refractory and recurrence. Methods of isolating these cells include but not limited to identification by their ability of efflux Hoechst 33342, identification by the surface markers these cells express, such as CD133, CD44, CD166, and others, and enrichment by their tumorigenic property. The mounting evidence linking cancer stem cells to tumorigenesis unravel enormous therapeutic opportunity of targeting cancer stem cells.

The data provided herein, combined with recent breakthroughs in CSC research, allows the present invention to provide an array of methods directed at inhibiting CSCs, methods directed at inhibiting both CSCs and heterogeneous cancer cells, and methods of treating cancers that have CSCs in specific or cancers in general. The present invention also provides related methods (e.g., manufacturing and drug candidate screening), materials, compositions and kits. The method can prevent the CSCs from self-renewal, such that it is no longer able to replenish its numbers by dividing into tumorigenic CSC cells. Or, the method can induce cell death in CSCs, or in both CSCs and heterogeneous cancer cells.

This method can be used to treat a subject's cancer. Cancers that are good candidates for such treatment include cancer(s) selected from the group consisting of esophageal cancer, gastroesophageal junction cancer, gastroesophageal adenocarcinoma, colorectal cancer, colon adenocarcinoma, rectal adenocarcinoma, colorectal adenocarcinoma, breast cancer, ovarian cancer, head and neck cancer, melanoma, chondrosarcoma, gastric adenocarcinoma, and adrenocorticoid.

Further, as CSCs have been demonstrated to be fundamentally responsible for tumorigenesis, cancer metastasis and cancer reoccurrence, any methods of the invention directed to inhibiting CSCs, or both CSCs and heterogeneous cancer cells, can be practiced to treat cancer that is metastatic, refractory to a chemotherapy or radiotherapy, or has relapsed in the subject after an initial treatment.

Figure 2:
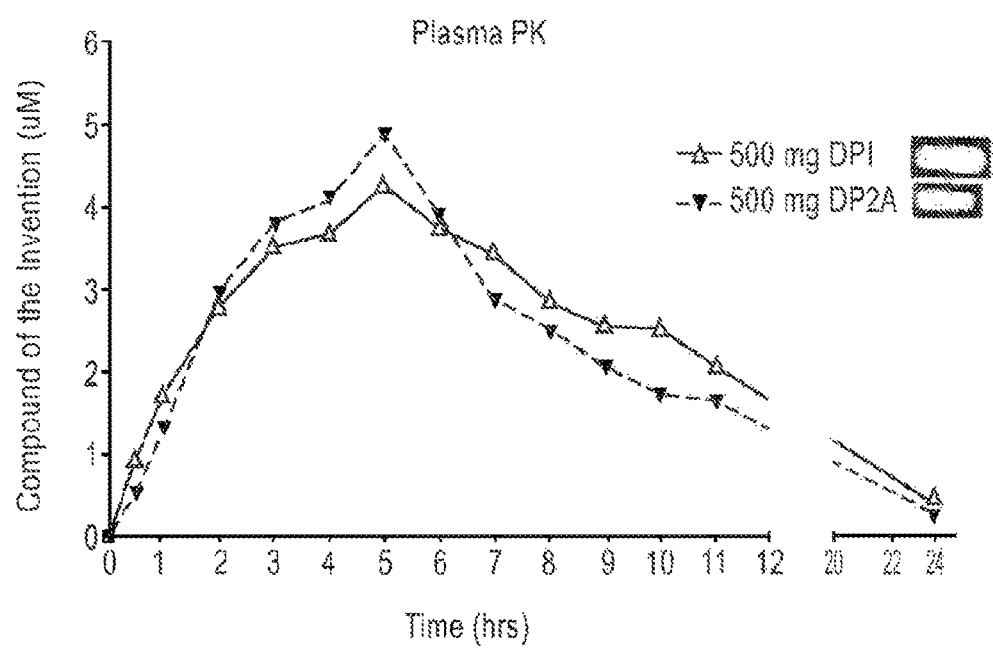
FIG. 2 is a graph that compares the pharmacokinetics of two different formulations of the Compound of the Invention. The two formulations result in different sizes of the capsule.

In some embodiments, the cancer stem cell inhibitor according to the present invention is: a compound of Formula 1, Compound 1, a polymorph of Compound 1, a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399, a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399, a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof, a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399, a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 12.3 degrees 2θ, a peak at least at about 15 degrees 2θ, a peak at least at about 23 degrees 2θ, a peak at least at about 23.3 degrees 2θ, a peak at least at about 24.6 degrees 2θ, and a peak at least at about 28.4 degrees 2θ and any combinations thereof, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof; a polymorph of a compound of Formula 1, Compound 1, a polymorph of Compound 1, a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399, a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399, a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof, a polymorph of 2-acetyl-4H, 9H-naphtho[2,3-b]furan-4,9-dione characterized by an X-ray diffraction pattern substantially similar to that set forth in FIG. 3 of WO 2011/116398 and WO 2011/116399, a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 12.3 degrees 2θ, a peak at least at about 15 degrees 2θ, a peak at least at about 23 degrees 2θ, a peak at least at about 23.3 degrees 2θ, a peak at least at about 24.6 degrees 2θ, and a peak at least at about 28.4 degrees 2θ and any combinations thereof, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof; or a substantially pure form of a compound of Formula 1, Compound 1, a polymorph of Compound 1, a polymorph of 2-acetyl-4H, 9H-naphtho[2,3-b]furan-4,9-dione characterized by an X-ray diffraction pattern substantially similar to that set forth in FIG. 1 of WO 2011/116398 and WO 2011/116399, a polymorph of 2-acetyl-4H, 9H-naphtho[2,3-b]furan-4,9-dione characterized by an X-ray diffraction pattern substantially similar to that set forth in FIG. 2 of WO 2011/116398 and WO 2011/116399, a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof, a polymorph of 2-acetyl-4H, 9H-naphtho[2,3-b] furan-4,9-dione characterized by an X-ray diffraction pattern substantially similar to that set forth in FIG. 3 of WO 2011/116398 and WO 2011/116399, a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 12.3 degrees 2θ, a peak at least at about 15 degrees 2θ, a peak at least at about 23 degrees 2θ, a peak at least at about 23.3 degrees 2θ, a peak at least at about 24.6 degrees 2θ, and a peak at least at about 28.4 degrees 2θ and any combinations thereof, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4, 9-dioxo-3a,4,9,9a-tetrahydro-naphtho[2,3-b]furan-2-yl)-vinyl ester dimethyl ester, an enantiomer, diastereomer, tautomer, and a salt or solvate thereof; a particle form of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2, 3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof (also referred to herein as the "Compound of the Invention").

The present invention provides a method of identifying a drug candidate capable of inhibiting a cancer stem cell. In some embodiments, the drug candidate is capable of inducing cell death in CSC or at least inhibiting its self-renewal. In a further embodiment, the drug candidate is capable of inducing cell death in CSC or at least inhibiting its self-renewal, and inducing cell death in heterogeneous cancer cells. Various phases in the pathway can be targeted for screening the drug candidate.

Accordingly, in another aspect, the Compound of the Invention can be used to formulate a pharmaceutical composition to treat or prevent disorders or conditions. In some embodiments, the cancer is selected from the group consisting of esophageal cancer, gastroesophageal junction cancer, gastroesophageal adenocarcinoma, colorectal cancer, colon adenocarcinoma, rectal adenocarcinoma, colorectal adenocarcinoma, breast cancer, ovarian cancer, head and neck cancer, melanoma, chondrosarcoma, gastric adenocarcinoma, and adrenocorticoid.

Accordingly, in an aspect, the present invention provides a method of inhibiting cancer stem cells where an effective amount of the Compound of the Invention is administered to the cells. Cancers known to have CSCs are good candidates for such treatments, and include but are not limited to: cancer(s) selected from the group consisting of esophageal cancer, gastroesophageal junction cancer, gastroesophageal adenocarcinoma, colorectal cancer, colon adenocarcinoma, rectal adenocarcinoma, colorectal adenocarcinoma, breast cancer, ovarian cancer, head and neck cancer, melanoma, chondrosarcoma, gastric adenocarcinoma, and adrenocorticoid.

Further, as CSCs have been demonstrated to be fundamentally responsible for tumorigenesis, cancer metastasis and cancer reoccurrence, any methods of the invention directed to inhibiting CSCs can be practiced to treat cancer that is metastatic, refractory to a chemotherapy or radiotherapy, or has relapsed in the subject after an initial treatment.

In some embodiments of the method, the cancer being treated is selected from the following group: esophageal cancer, gastroesophageal junction cancer, gastroesophageal adenocarcinoma, colorectal cancer, colon adenocarcinoma, rectal adenocarcinoma, colorectal adenocarcinoma, breast cancer, ovarian cancer, head and neck cancer, melanoma, chondrosarcoma, gastric adenocarcinoma, and adrenocorticoid. The cancer may implicate malfunction of the STAT3, Nanog and/or β-catenin pathway.

In an aspect, the present invention provides a method of treating cancer in a subject, where a therapeutically effective amount of a pharmaceutical composition including the Compound of the Invention is administered to the subject. The cancer may be metastatic, refractory or recurrent. The subject may be a mammal, e.g., a human being.

Treatment by administration of particles of, for example, a compound according to Formula I to a subject (patient) suffering from a neoplasm may be indicated for the following conditions. The neoplasm may be refractory to treatment by chemotherapy, radiotherapy, or hormone therapy. The neoplasm may not be amenable to surgical resection. The neoplasm may have relapsed in the subject (patient). Cancer stem cells have been implicated in the relapse of neoplasms; killing the cancer stem cells or inhibiting their self-renewal by a method according to the present invention may prevent the neoplasm from regenerating itself. Treatment by administration of particles of naphthofuran may slow or stop the volume growth of a neoplasm or decrease the volume of a neoplasm by, for example, inducing the death of, inhibiting the growth and/or division of, and/or selectively killing neoplastic cells. For example, a treatment according to the present invention may induce cell death of a cell of the neoplasm. For example, the treatment may act to inhibit the STAT3, Nanog and/or β-catenin pathway of a neoplastic cell.

Treatment by administration of particles of, for example, a Compound of the Invention to a subject (patient) suffering from a neoplasm may be used to prevent relapse of a neoplasm and/or as an adjuvant therapy to surgical resection.

A pharmaceutical composition including particles of, for example, a Compound of the Invention may be administered orally, as this is a convenient form of treatment. For example, the pharmaceutical composition may be administered orally no more than four times per day. Alternatively, the pharmaceutical composition can be administered intravenously or intraperitoneally.

Patient Screening Using Putative Biomarker

Figure 3A:
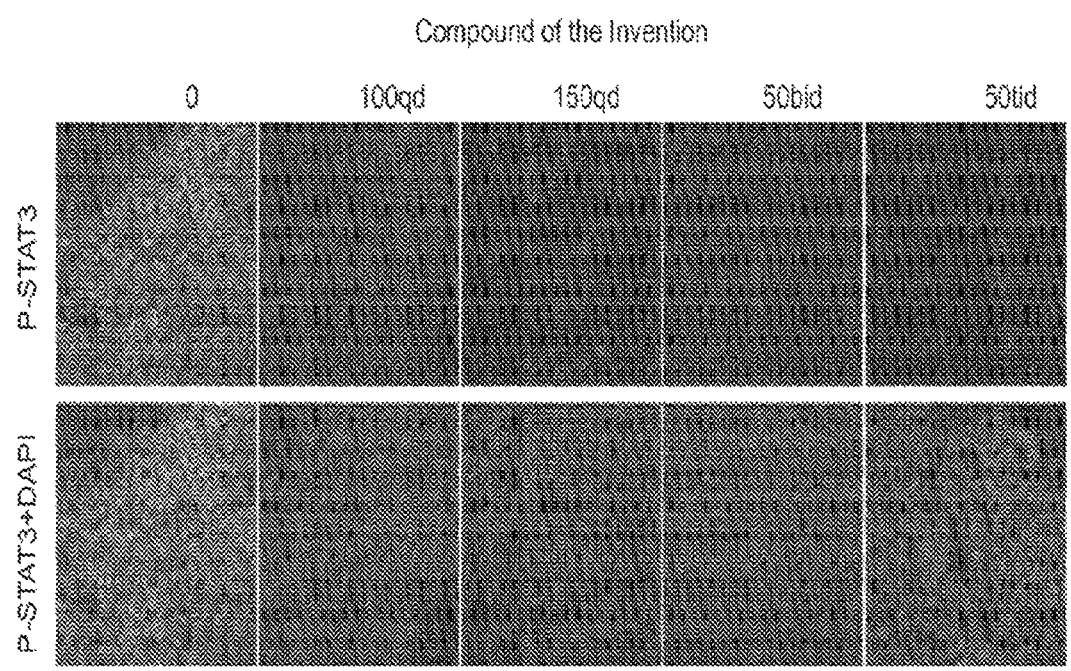
FIG. 3A consists of photographic images of tumor tissue samples from CRC patients visualized through immunohistochemistry using antibodies against phosphorylated STAT3 and DAPI (lower row).
Figure 3B:
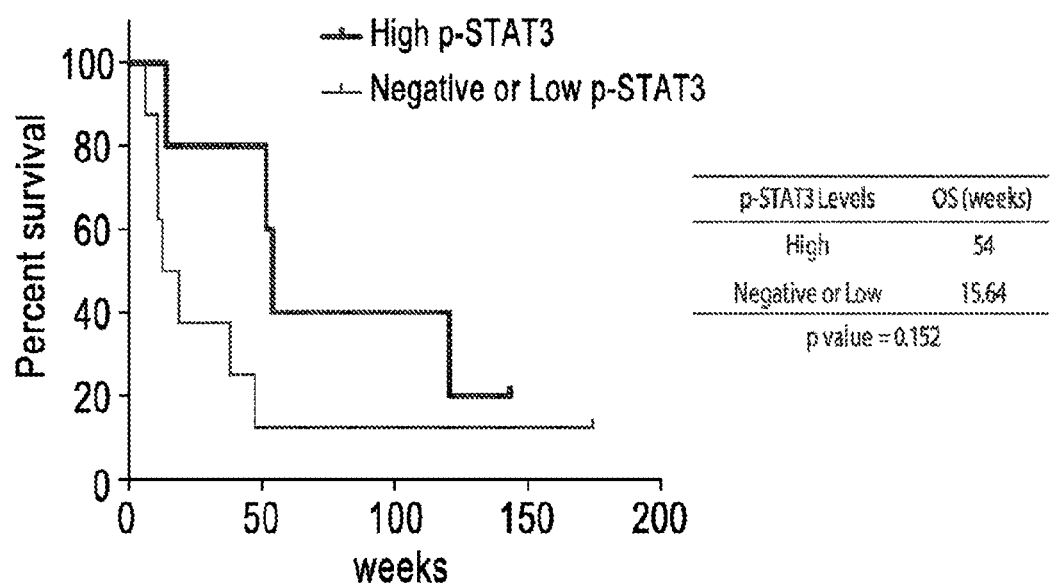
FIG. 3B is a chart showing a trend towards improvement in survival for patients with high p-STAT3 (compared with patients having low or negative p-STAT3).

Based on the discovery that phosphorylated STAT3 (p-STAT3) positivity and β-catenin expression in cellular nucleus can both, individually or in combination, serve as predictive biomarkers for higher likelihood of treatment efficacy using the Compound of the Invention (see Examples 9 and 10), the present invention provides ways to screen patients for recommendation of cancer treatments that involve the Compound of the Invention. Our data indicates a direct correlation between the level of p-STAT3 in tumor tissues before treatment and the chance of survival or treatment success with the Compound of the Invention. In other words, the higher the level of p-STAT3 found in a cancer patient before treatment, at least in colorectal cancer (CRC) patients, the higher overall survival (OS) is once treatment using the Compound of the Invention and related compositions (FIG. 3B). Accordingly, the present invention provides a method of treating cancer in a selected patient population or screening potential cancer patients for treatment, the method comprising the steps of: measuring a level of phosphorylated STAT3 (p-STAT3) in a biological sample (e.g., tumor tissue before treatment) obtained from a patient candidate diagnosed of a cancer (e.g., colorectal adenocarcinoma); confirming that the patient candidate's p-STAT3 level is above a benchmark level; and administering to the patient candidate a therapeutically effective amount of the Compound of the Invention or a pharmaceutically acceptable salt, solvate, hydrate, or prodrug thereof. The benchmark level may differ for different demographic sectors, and can be determined by one skilled artisan through routine experimentation.

Figure 4A:
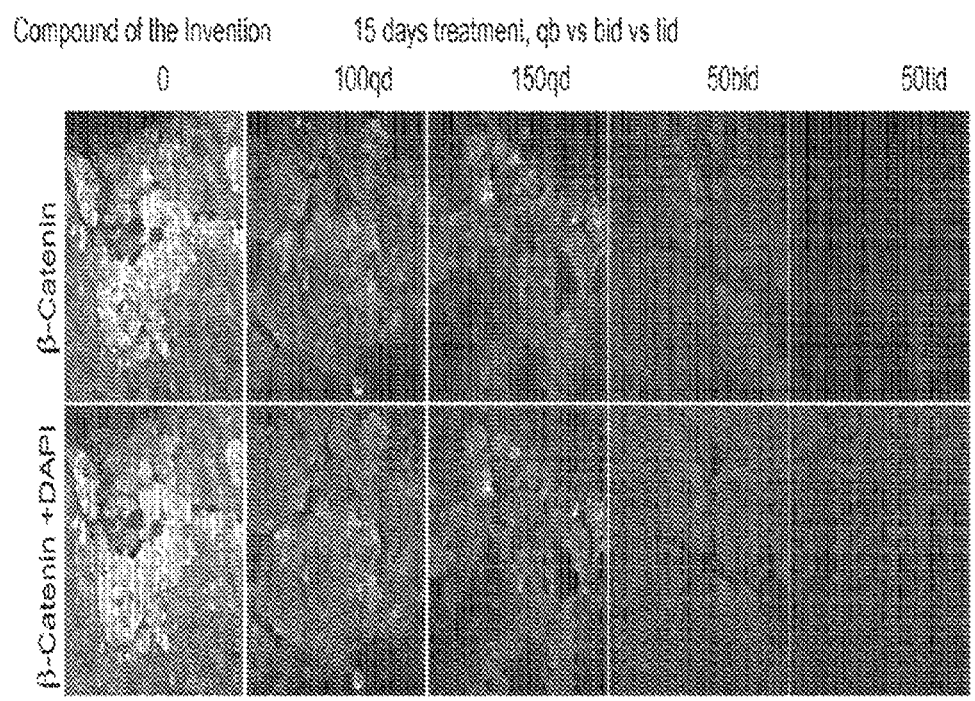
FIG. 4A consists of photographic images of tumor tissue samples from CRC patients visualized through immunohistochemistry using antibodies against β-catenin and DAPI (lower row).
Figure 4B:
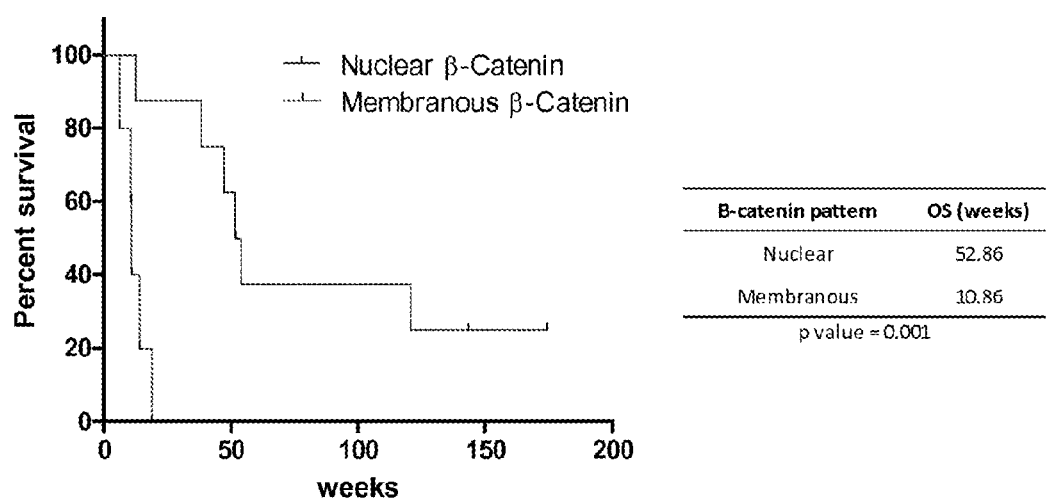
FIG. 4B is a chart showing a trend towards improvement in survival for patients with nuclear β-catenin localization (compared with patients having β-catenin localized to the cell membrane).

Similarly, because our data indicates a direct correlation between the level of expression or localization of β-catenin, an oncogene closely linked to STAT3, in the cell nucleus and the chance of survival or treatment success with the Compound of the Invention. In other words, the higher the expression level of β-catenin in cancer cell nucleus as opposed to the cell membrane in a cancer patient, at least in CRC patients, the higher overall survival (OS) is (FIG. 4B). Accordingly, the present invention provides a method of treating cancer in a selected patient population or screening potential cancer patients for treatment, the method comprising the steps of: detecting a locus of β-catenin expression in a biological sample (e.g., tumor tissue before treatment) obtained from a patient candidate diagnosed of a cancer; confirming that significant β-catenin expression is detected in cell nucleus in the sample from the patient candidate; and administering to the patient candidate a therapeutically effective amount of the Compound of the Invention or a pharmaceutically acceptable salt, solvate, hydrate, or prodrug thereof. The level at which nuclear expression for β-catenin is considered clinically significant here may differ for different demographic sectors, and can be determined by one skilled artisan through routine experimentation.

The invention provides kits and/or for of identifying or otherwise refining, e.g., stratifying, a patient population suitable for therapeutic administration of a compound of the disclosure by detecting the level of expression of one or more biomarkers associated with cancer stemness. In the methods and/or kits of the disclosure, the level of expression of one or more cancer stemness markers is detected in a patient or a sample from a patient, and where the patient or sample has an elevated level of one or more cancer stemness markers as compared to a control level of expression, the patient is then administered a therapeutically effective amount of a compound of the disclosure. In some embodiments of these methods, the method is an in vivo method. In some embodiments of these methods, the method is an in situ method. In some embodiments of these methods, the method is an ex vivo method. In some embodiments of these methods, the method is an in vitro method.

Understanding the clinical relevance of the cancer stemness markers and identifying their predictive response to the Compound of the Invention is used herein to assist clinical development by selecting patients that will most likely to derive clinical benefit. In some embodiments, the methods provided herein use one or more well-known cancer stemness marker(s), such as, for example, the expression of p-STAT3 and/or other cancer stem cell related proteins such as β-catenin and NANOG. All these proteins can be easily detected using any of a variety of art-recognized techniques. In some embodiments, the cancer sternness marker is detected with immunohistochemistry with antibodies. Using the archival tissue samples collected from the phase I trial with the Compound of the Invention, the patient response to the Compound of the Invention was analyzed based on biomarker status. An analysis of CRC patients treated with the Compound of the Invention demonstrated a trend of increased survival for patients with high level of p-STAT3 or NANOG as compared with patients having low or negative levels of p-STAT3 or NANOG. A significant improvement in survival was detected for patients with nuclear β-Catenin localization compared with patients having β-catenin localized to the cell membrane, HR=0.043, p value <0.001. As further evidence, in an in vitro study screening a panel of cancer cells, the cell lines with nuclear β-Catenin show a lower $IC_{50}$ for the Compound of the Invention. Additionally, inhibition of STAT3 by the Compound of the Invention reduced β-catenin protein levels both in vitro within cancer cell lines. Thus, STAT3 activation is involved in nuclear β-catenin regulation. In addition, β-catenin status is a biomarker for predicting responsiveness of CRC patients to the Compound of the Invention.

In various embodiments of the above treatment methods, the cancer may be one of the following: esophageal cancer, gastroesophageal junction cancer, gastroesophageal adenocarcinoma, colorectal adenocarcinoma, breast cancer, ovarian cancer, head and neck cancer, melanoma, gastric adenocarcinoma, and adrenocorticoid. The cancer may be refractory, recurrent or metastatic.

Drug Regimen, Dosage and Interval

In a method according to the present invention, the therapeutically effective amount of the pharmaceutical composition including particles, polymorphs and/or purified forms of a Compound of the Invention can be a total daily dose in the range from about 20 mg to about 2000 mg, from about 100 mg to about 1500 mg, from about 160 mg to about 1400 mg, or from about 180 mg to about 1200 mg. In some embodiments, the therapeutically effective amount of the pharmaceutical composition including particles, polymorphs and/or purified forms of a Compound of the Invention is a total daily dose in the range of from about 200 mg to about 1500 mg, or from about 360 mg to 1200 mg. In some embodiments, the therapeutically effective amount of the pharmaceutical composition including particles, polymorphs and/or purified forms of a Compound of the Invention is a total daily dose in the range of from about 400 mg to about 1000 mg. In some embodiments, the therapeutically effective amount of the pharmaceutical composition including particles, polymorphs and/or purified forms of a Compound of the Invention is a total daily dose of about 1000 mg.

Intervals between each dose can vary or stay constant, depending on factors such as pharmacokinetics of the composition, drug metabolism with or without intake of fluid or food, tolerability and other drug adherence factors (e.g., convenience). A preferred interval maintains an effective level of the pharmaceutical composition in the body while causing minimal adverse side effects. In some embodiments, the interval between each dose ranges from about 4 hours to about 24 hours. In some embodiments, the interval between each dose ranges from about 8 hours to about 14 hours. In some embodiments, the interval between each dose ranges from about 10 hours to about 13 hours, or, is about 12 hours. Accordingly in those embodiments, the compound is administered to the subject about twice daily, for example, on average over the duration of a regimen.

In some embodiments, the therapeutically effective amount of the pharmaceutical composition including particles, polymorphs and/or purified forms of a Compound of the Invention is a total daily dose in a range of from about 160 mg to about 960 mg or about 1000 mg. In some embodiments, the therapeutically effective amount of the pharmaceutical composition including particles, polymorphs and/or purified forms of a Compound of the Invention is a total daily dose selected from the group consisting of about 160 mg, about 320 mg, about 640 mg, about 800 mg, and about 960 mg. In some embodiments, the therapeutically effective amount of the pharmaceutical composition including particles, polymorphs and/or purified forms of a Compound of the Invention is administered to the subject at a total daily dose of about 960 mg.

In some embodiments, the therapeutically effective amount of the pharmaceutical composition including particles, polymorphs and/or purified forms of a Compound of the Invention is administered BID. In some embodiments, the therapeutically effective amount of the pharmaceutical composition including particles, polymorphs and/or purified forms of a Compound of the Invention is administered to the subject at a dose in a range of from about 80 mg BID to about 480 mg BID. In some embodiments, the therapeutically effective amount of the pharmaceutical composition including particles, polymorphs and/or purified forms of a Compound of the Invention is administered to the subject at a dose selected from the group consisting of about 80 mg BID, about 160 mg BID, about 320 mg BID, about 400 mg BID, and about 480 mg BID. In some embodiments, the therapeutically effective amount of the pharmaceutical composition including particles, polymorphs and/or purified forms of a Compound of the Invention is administered to the subject at a dose of about 480 mg BID.

In some embodiments, the therapeutically effective amount of the pharmaceutical composition including particles, polymorphs and/or purified forms of a Compound of the Invention is administered BID where the timing between administrations of the compound is in the range from about 4 hours between administrations to about 16 hours between administrations. In some embodiments, the therapeutically effective amount of the pharmaceutical composition including particles, polymorphs and/or purified forms of a Compound of the Invention is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 and/or at least 16 hours. In some embodiments, the therapeutically effective amount of the pharmaceutical composition including particles, polymorphs and/or purified forms of a Compound of the Invention is administered to the subject at a dose in a range of from about 80 mg BID to about 480 mg BID where the timing between administrations of the compound is in the range from about 4 hours between administrations to about 16 hours between administrations. In some embodiments, the therapeutically effective amount of the pharmaceutical composition including particles, polymorphs and/or purified forms of a Compound of the Invention is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 and/or at least 16 hours. In some embodiments, the therapeutically effective amount of the pharmaceutical composition including particles, polymorphs and/or purified forms of a Compound of the Invention is administered to the subject at a dose selected from the group consisting of about 80 mg, about 160 mg, about 320 mg BID, about 400 mg BID, and about 480 mg BID, where the timing between administrations of the compound is in the range from about 4 hours between administrations to about 16 hours between administrations. In some embodiments, the therapeutically effective amount of the pharmaceutical composition including particles, polymorphs and/or purified forms of a Compound of the Invention is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 and/or at least 16 hours. In some embodiments, the therapeutically effective amount of the pharmaceutical composition including particles, polymorphs and/or purified forms of a Compound of the Invention is administered to the subject at a dose of about 480 mg BID where the timing between administrations of the compound is in the range from about 4 hours between administrations to about 16 hours between administrations. In some embodiments, the therapeutically effective amount of the pharmaceutical composition including particles, polymorphs and/or purified forms of a Compound of the Invention is administered to the subject at a dose of about 80 mg BID where the timing between administrations of the compound is in the range from about 4 hours between administrations to about 16 hours between administrations. In some embodiments, the therapeutically effective amount of the pharmaceutical composition including particles, polymorphs and/or purified forms of a Compound of the Invention is administered to the subject at a dose of about 400 mg BID where the timing between administrations of the compound is in the range from about 4 hours between administrations to about 16 hours between administrations. In some embodiments, the therapeutically effective amount of the pharmaceutical composition including particles, polymorphs and/or purified forms of a Compound of the Invention is administered to the subject at a dose of about 320 mg BID where the timing between administrations of the compound is in the range from about 4 hours between administrations to about 16 hours between administrations. In some embodiments, the therapeutically effective amount of the pharmaceutical composition including particles, polymorphs and/or purified forms of a Compound of the Invention is administered BID where the timing between administrations of the compound is at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 and/or at least 16 hours.

In some embodiments, the therapeutically effective amount of the pharmaceutical composition including particles, polymorphs and/or purified forms of a Compound of the Invention is administered to the subject at a dose of about 480 mg BID where the timing between administrations of the compound is about 12 hours between administrations. In some embodiments, the therapeutically effective amount of the pharmaceutical composition including particles, polymorphs and/or purified forms of a Compound of the Invention is administered to the subject at a dose of about 80 mg BID where the timing between administrations of the compound about 12 hours between administrations. In some embodiments, the therapeutically effective amount of the pharmaceutical composition including particles, polymorphs and/or purified forms of a Compound of the Invention is administered to the subject at a dose of about 400 mg BID where the timing between administrations of the compound is about 12 hours between administrations. In some embodiments, the therapeutically effective amount of the pharmaceutical composition including particles, polymorphs and/or purified forms of a Compound of the Invention is administered to the subject at a dose of about 320 mg BID where the timing between administrations of the compound is about 12 hours between administrations.

A Compound of the Invention or a pharmaceutical composition thereof can be administered through any one of or through a combination of routes, for example, orally, intravenously, or intraperitoneally. For example, in some embodiments, a Compound of the Invention can be administered orally. In some embodiments, a Compound of the Invention can be administered orally in a formulation that includes lauroyl polyoxylglycerides (e.g. Gelucire) and Tween 80, or a formulation that includes lauroyl polyoxylglycerides (e.g. Gelucire), linoleoyl polyoxylglycerides (e.g. Labrafil), and a surfactant such as sodium lauryl sulfate (SLS) or sodium dodecyl sulfate (SDS).

A Compound of the Invention can be administered in a dose to achieve a blood concentration in a subject, e.g., a patient, of compound in the range of from at least about 0.002 µM to about 30 µM for a time of at least 2 hours to no more than 24 hours. In some embodiments, a Compound of the Invention can be administered in a dose to achieve a blood concentration in a subject of compound in the range of from at least about 0.2 µM to about 1 µM for a time of at least 2 hours to no more than 24 hours. equals to or above about 0.2 µM, 0.5 µM, 1.0 µM, 1.5 µM, 2.0 µM, 2.5 µM, 3.0

μM 4.0 μM, 5.0 μM, 6.0 μM, 7.0 μM, 8.0 μM, 9.0 μM, 10.0 μM, 15.0 μM for at least 2 hours and less than 24 hours. In some embodiments, a Compound of the Invention can be administered in a dose to achieve a blood concentration in a subject of compound equals to or above about 1.0 μM, 1.5 μM, 2.0 μM, 3.0 μM, 5.0 μM, 10.0 μM, 15.0 μM for at least 2 hours and less than 24 hours. In some embodiments, a Compound of the Invention can be administered in a dose to achieve a blood concentration in a subject of compound equals to or above about 2.0 μM, 3.0 μM, 5.0 μM, 10.0 μM for at least 2 hours and less than 24 hours. In some embodiments, a Compound of the Invention can be administered in a dose to achieve a blood concentration in a subject of compound equals to or above about 3.0 μM, or 5.0 μM for at least 2 hours and less than 24 hours.

A Compound of the Invention can be administered in a dose to achieve a blood concentration in a subject, e.g., a patient, of compound in the range of from at least about 0.002 μM·h to about 300 μM·h in 24 hours. In some embodiments, a Compound of the Invention can be administered in a dose to achieve area under the curve in 24 hours (AUC24) in a subject equals to or above about 0.2 μM, 0.5 μM, 1.0 μM, 1.5 μM, 2.0 μM, 2.5 μM, 3.0 μM 4.0 μM, 5.0 μM, 6.0 μM, 7.0 μM, 8.0 μM, 9.0 μM, 10.0 μM, 15.0 μM for at least 2 hours and less than 24 hours. In some embodiments, a Compound of the Invention can be administered in a dose to achieve a blood concentration in a subject of compound equals to or above about 1.0 μM, 1.5 μM, 2.0 μM, 3.0 μM, 5.0 μM, 10.0 μM, 15.0 μM for at least 2 hours and less than 24 hours. In some embodiments, a Compound of the Invention can be administered in a dose to achieve a blood concentration in a subject of compound equals to or above about 2.0 μM, 3.0 μM, 5.0 μM, 10.0 μM for at least 2 hours and less than 24 hours. In some embodiments, a Compound of the Invention can be administered in a dose to achieve a blood concentration in a subject of compound equals to or above about 3.0 μM, or 5.0 μM for at least 2 hours and less than 24 hours. In some embodiments, a Compound of the Invention can be administered in a dose to achieve area under the curve in 24 hours ($AUC_{0-24\ hr}$) in a subject equals to or above about 2 μM*hr, 10 μM*hr, 20 μM*hr, M*hr, 40 μM*hr, 50 μM*hr, 60 μM*hr, 70 μM*hr, 80 μM*hr, 90 μM*hr, 100 μM*hr, 125 μM*hr, 150 μM*hr, 200 μM*hr, 250 μM*hr, 300 μM*hr, 400 μM*hr, and 500 μM*hr.

If the condition of the subject (patient) so requires, doses of the pharmaceutical composition may be administered as a continuous or pulsatile infusion. The duration of a treatment may be decades, years, months, weeks, or days, as long as the benefits persist. The foregoing ranges are provided only as guidelines and are subject to optimization.

In a method according to the invention, cells of the neoplasm are selectively killed by administering the pharmaceutical composition, so that the blood molar concentration of the compound is at least an effective concentration and less than a harmful concentration for a first continuous time period that is at least as long as an effective time period and shorter than a harmful time period. The blood molar concentration can be less than the effective concentration after the first continuous time period. The effective concentration can be a concentration sufficiently high, so that neoplastic cells, e.g., cancer cells, are killed. The effective time period can be sufficiently long, so that neoplastic cells, e.g., cancer cells, are killed. The harmful concentration can be a concentration at which normal cells are damaged or killed. The harmful time period can be a time period sufficiently long for normal cells to be damaged or killed. For example, the effective concentration can be equal to or above about 0.02 μM, about 0.05 μM, about 0.1 μM, about 0.2 μM, about 0.5 μM, about 1 μM, about 3 μM, about 10 μM or about 20 μM. For example, the non-harmful concentration can be equal to or below about 3 μM, about 10 μM, about 14 μM, about 30 μM, or about 100 μM. For example, the effective time period can be equal to or above about 2 hour, about 4 hours, about 6 hours, about 12 hours, about 24 hours, or about 48 hours. For example, to achieve non-harmful exposure for normal cells, drug concentration of Compound 1 has to be substantially cleared from blood within about 12 hours, about 24 hours. "Substantially clearance from blood" means blood drug concentration decrease by at least about 50%, at least about 60%, at least about 80%, at least about 90%. For example, an effective concentration can be a concentration that exceeds the $IC_{50}$ of cancer cells when the compound is administered for some time period. For example, an effective time period can be a time period over which cancer cells are selectively inhibited or killed when the compound is administered at least at the effective concentration. For example, a harmful concentration can be a concentration that exceeds the $IC_{50}$ of normal cells when the compound is administered for any time period. For example, a harmful time period can be a time period over which normal as well as cancer cells are inhibited or killed when the compound is administered at the effective concentration.

One of skill in the art can administer the pharmaceutical composition by selecting dosage amount and frequency so as to achieve a herein described "selective pharmacokinetic profile" (SPP) deemed necessary for selective killing neoplastic cells, such as cancer cells, and sparing normal cells. Such consideration of the SPP can also guide the design of the pharmaceutical composition, for example, the particle size distribution and distribution of shapes of the particles.

In a method according to the invention, the pharmaceutical composition is administered orally in a dosage form such as a tablet, pill, capsule (hard or soft), caplet, powder, granule, suspension, solution, gel, cachet, troche, lozenge, syrup, elixir, emulsion, oil-in-water emulsion, water-in-oil emulsion, or draught.

Identifying an Optimum Particle Size Distribution

In a method according to the invention, an optimum particle size distribution of a compound according to Formula I, Compound 1, a polymorph of Compound 1, and/or a substantially pure form of Compound 1 for treating a human, mammal, or animal afflicted with a neoplasm can be determined as follows. At least one set of particles including the compound can be prepared. In preparing the set of particles, for example, the particle size of a sample of solid compound can be reduced by, for example, dissolving the compound and nebulizing the solution, dissolving the compound and sonicating the solution, ball milling the solid compound, roll milling the solid compound, grinding the solid compound, and/or sieving the solid compound. The particle size distribution of the at least one set of particles can be determined by a method or combination of methods known to one of skill in the art. For example, the particle size distribution can be determined using a technique such as sieve analysis, optical microscopic counting, electron micrograph counting, electroresistance counting, sedimentation time, laser diffraction, acoustic spectroscopy, another technique, or a combination of techniques. The at least one set of particles can be administered to neoplastic cells and to normal cells at a predetermined concentration and for a predetermined period of time. The effect of the particles on the metabolism, division, and/or other indicator of the vitality of the neoplastic cells and the normal cells can be observed. The observed effect of the particles on the neoplastic cells can be used to assign an effectivity rating to each set of particles. For example, a set of particles that inhibits the metabolism and/or division of the neoplastic cells, damages or kills the neoplastic cells, or otherwise exhibits high antitumor activity can be assigned a high effectivity rating. The observed effect of the particles on the normal cells can be used to assign a toxicity rating to each set of particles. For example, a set of particles that inhibits the metabolism and/or division of the normal cells or damages or kills the normal cells or where the normal cells otherwise exhibit a low tolerability of the set of particles can be assigned a high toxicity rating.

For example, the set of particles can be administered to neoplastic cells and normal cells in vitro. For example, the effectivity rating can be equal to, proportional to, or a monotonically increasing function of the $IC_{50}$ of the neoplastic cells. For example, the toxicity rating can be equal to, proportional to, or a monotonically increasing function of the $IC_{50}$ of the normal cells.

For example, the set of particles can be administered to neoplastic cells and normal cells in vivo in a test animal. For example, the test animal can be a mammal, primate, mouse, rat, guinea pig, rabbit, or dog. For example, the effectivity rating can be equal to, proportional to, or a monotonically increasing function of the decrease in volume of the neoplastic cells following administration of the set of particles. For example, the toxicity rating can be equal to, proportional to, or a monotonically increasing function of the decrease in mass of the test animal following administration of the set of particles. For example, the set of particles can be administered to a human in a clinical study. A method of treating a neoplasm can include administering a therapeutically effective amount of a set of particles of the compound according to Formula I, Compound 1, a polymorph of Compound 1, and/or a substantially pure form of Compound 1 to a human, mammal, or animal afflicted with the neoplasm. Prior to administration of the particles of the compound, the compound according to Formula I, Compound 1, a polymorph of Compound 1, and/or a substantially pure form of Compound 1 to an animal or a human or to cells in vitro, the particles can be suspended in a pharmaceutically acceptable excipient.

The effectivity rating and/or the toxicity rating of each set of particles having a first particle size distribution can be compared with the effectivity rating and/or the toxicity rating of another set or sets of particles having a particle size distribution different than the first particle size distribution. A set of particles of a compound that has a high effectivity rating and a low toxicity rating can be effective in inhibiting or killing neoplastic, e.g., cancer, cells, but spare normal cells. One of skill in the art can select as an optimum set the set of particles having an effectivity rating greater than, a toxicity rating less than, and/or a weighted effectivity rating and toxicity rating sum greater than the at least one other set of particles (for example, the effectivity rating can be weighted with a positive coefficient and the toxicity rating can be weighted with a negative coefficient). One of skill the art can also use another criteria to select the optimum set of particles, for example, particles having a sum of the weighted effectivity rating and the weighted ratio of the effectivity rating over the toxicity rating. The particle size distribution of the optimum set of particles can be considered an optimum particle size distribution for the compound tested. The optimum particle size distribution may be different for one compound, e.g., Compound 1, than for another compound, e.g., a compound according to Formula I that is not Compound 1. The optimum particle size distribution for a given compound may differ when determined by administration to cells in vitro, to a small test animal, and to a large test animal. However, the optimum particle size distribution determined by administration of a given compound to an organism in vitro or in vivo may represent a rational starting point for optimizing the particle size distribution for another compound or for administration to another organism.

An optimum set of particles of the compound according to Formula I, Compound 1, a polymorph of Compound 1, and/or a substantially pure form of Compound 1 can be included in the composition for reducing or inhibiting the replication or spread of neoplastic cells.

EXAMPLES

Examples are provided below to further illustrate different features of the present invention. The examples also illustrate useful methodology for practicing the invention. These examples do not limit the claimed invention.

Example 1: Preparation of a Naphthofuran Compound

The procedure for preparation of a naphthofuran compound (2-acetylnaphtho[2,3-b]furan-4,9-dione) is summarized as follows:

Step 1: Bromination

To a 2 liter 3 neck round bottom flask equipped with a mechanical stirrer, thermometer, and addition funnel is charged 3-butene-2-one (451.2 grams). To the addition funnel is added bromine (936.0 grams). After the content in the flask is cooled to −5° C., the bromine is dropped into the flask with vigorous stirring and maintaining temperature at −5° C. over 30 minutes. The mixture is stirred for an additional 15 minutes at −5° C., and then is split into 4 equal portions.

Step 2 Debromination

Each portion of the mixture along with tetrahydrofuran (2133.6 grams) is loaded into a 22 liter 4 neck round bottom flask equipped with a mechanical stirrer, thermometer, and addition funnel. To the addition funnel is charged DBU (1,3-Diazabicyclo[5.4.0]undec-7-ene, 222.9 grams). The DBU is dropped into the flask with vigorous stirring and maintaining temperature at 0° C.-5° C. over 30 minutes. The mixture is stirred for an additional 15 min at 0° C.-5° C.

Step 3: Coupling Reaction 2-hydroxy-1,4-naphthofuran (231 grams) is then added into the flask. Additional DBU (246.0 grams) is charged into the addition funnel and then dropped into the mixture in the flask at such a rate that the temperature of the reaction mixture does not exceed 40° C. After the addition of DBU is complete, the resulting mixture is stirred overnight at room temperature, and a sample of the reaction mixture is taken for HPLC analysis.

Step 4: Crystallization

To the reaction mixture, water (10.8 liters) is charged, and the resulting mixture is cooled to 0° C.-3° C. for at least 30 minutes, then filtered via vacuum filter. The filtered solid is rinsed with 5% aqueous sodium bicarbonate (3 liters), water (3 liters), 1% aqueous acetic acid (3 liters) and ethanol twice (2×1 liter) successively.

The rinsed solid is stored and pooled together from other batches. The combined crude product (28.73 kg) is loaded along with ethyl acetate (811.7 kg) into a 500 gallon vessel equipped with a mechanical stirrer, thermometer, and a condenser. Under nitrogen atmosphere, the mixture is heated to reflux (72° C.) for 2 hours, and then filtered with a 10 micron cartridge filter containing an active carbon layer to remove insolubles.

Fresh hot ethyl acetate (10 kg) is used to rinse the vessel, transfer line and filter. The combined filtrate is cooled to 0-5° C. and held at this temperature for 2 hours, and then is filtered with 20 inch Buchner filter. The filtered solid product is rinsed with 0-5° C. ethyl acetate (5.7 kg), and dried under vacuum at 40° C. to a constant weight. The remaining filtrate is reduced in volume by 63% by evaporation, and the crystallization process was repeated again to generate a second crop of product which was also dried under the same condition as the first crop of product.

A lot of the naphthofuran compound obtained following the procedure. The purity for the lot of the compound is 95.44 area % (HPLC).

Example 2: Preparation of a Naphthofuran Compound

Another procedure for the preparation of a naphthofuran compound (2-acetylnaphtho[2,3-b]furan-4,9-dione) is summarized as follows:

Step 1: Bromination

A 12 L RBF (Round Bottom Flask)(protected from light with UV filters) was charged with MVK (2,160 ml, 26.4 mol) and cooled to −9.6° C. in a dry-ice/acetone bath. Bromine (1,300 ml, 25.3 mol) was added slowly, over 2 hrs and 20 min, maintaining T=<−2.6° C. ($T_{max}$). The resulting yellow mixture was stirred for additional 28 min.

Step 2: De-Hydrobromination

A 72 L RBF with pre-cooled THF (Tetrahydrofuran) (20 L, 5 ml/g HNQ (2-Hydroxy-1,4-naphtoquinone)) was charged with brominated product from the above and the resulting solution was cooled to −4.8° C. DBU (4,200 ml, 28.1 mol) dissolved in THF (4,200 ml) was added slowly, over 2 hrs and 20 min, maintaining T<0.3° C. ($T_{max}$). The resulting suspension was stirred for 42 min.

Step 3: Coupling

2-Hydroxy-1,4-naphthofuran (4,003 g, 23.0 mol) was charged, in one portion, into the reaction mixture from the above, at −1.8° C. A cooling bath was added while a second portion of DBU (3,780 ml, 25.3 mol) was added over 48 minutes to bring the reaction temperature to 40° C. The cooling bath was removed and the reaction mixture was stirred over the weekend, open to the air.

Step 4: Isolation of Crude Material

A 200 L reactor with pre-cooled water (100 L, 25 ml/g HNQ) was charged with the reaction mixture from the above. The resulting suspension was cooled to 6.0° C., and then stirred at T=3±3° C. for ~1 hour. The resulting suspension was then filtered, and the collected solids were transferred back to the 200 L reactor.

After stirring in 5% NaHCO$_3$ aqueous (26 L, 6.5 ml/g HNQ) for 1 hour, the suspension was filtered. The collected solids were transferred back to the 200 L reactor, stirred in water (26 L) for 1 hour, and then filtered.

The wet solids were transferred back to the 200 L reactor, stirred in 1% aqueous acetic acid (26 L) for ~1 hour, filtered and then washed on the filter funnel with water (10 L). The collected solids were transferred back to the 200 L reactor and heated in ethanol (17.5 L; 4.3 ml/g HNQ) to a gentle reflux (77.4° C.). The resulting suspension was cooled to 4.2° C. and filtered.

The wet solids were transferred to a 100 L reactor and heated in ethanol (17.5 L; 4.3 ml/g HNQ) to a reflux (77.6° C.). The resulting suspension was cooled to 4.5° C. and filtered. The wet cake was de-liquored overnight. $^1$H NMR and HPLC samples were taken. $^1$H NMR: Compound 1/NDHF (2-acetyl-2,3-dihydronaphtho[2,3-b]furan-4,9-dione) 42:58%; HPLC: Compound 1/NDHF 74:11 area %.

The solids were dried in a vacuum oven at 50° C., over 4 days, affording 2,268 g of crude Compound 1. $^1$H NMR: Compound 1/NDHF 41:59%; HPLC: Compound 1/NDHF 67:11 area %.

Step 5: Oxidation of the Naphthodihydrofurane

The crude Compound 1 (2.268 kg) was slurried in toluene (77 L). MnO$_2$ (9536 g) was added and the mixture was heated to a gentle reflux. TLC (1:1 EA:hexane) showed complete reaction after 1 hour.

The reaction mixture was then filtered hot through a preheated pad of Celite (1530 g, bottom layer), activated charcoal (2230 g, middle layer), and Celite (932 g, top layer). The yellow-orange filtrate was collected.

The filtrate was concentrated on the rotovap to approximately 1/10 volume. The slurry was filtered and washed with toluene. The crystals were then dried at 50° C. to give 952 g (42%) of dark yellow solid. HPLC: 99.94%. $^1$H NMR showed no naphthodihydrofuran.

The crystals were dried at 50° C. under vacuum for an additional 46-65 hours to reduce the amount of residual toluene in the material.

Step 6: Ethyl Acetate Treatment

The Compound 1 (5816 g) was charged to a 200 L reaction vessel. Ethyl acetate (145 L, 25 mL/g) was added, and the solution was heated to reflux over 2 hours 26 minutes. Reflux was maintained for 5 hours 30 minutes, and the mixture was then cooled and maintained overnight to 17° C.

The slurry was filtered on a polyethylene frit. The yellow crystals were air dried, then placed in trays in a vacuum oven for 75 hours, giving 5532 g (95.1% yield) of yellow solids. HPLC: 99.86%. $^1$H NMR matches the structure of Compound 1.

Step 7: Ethyl Acetate Re-Crystallization

A 2 L RBF was charged with crude material (10 g) and ethyl acetate (900 ml). The mixture was refluxed at ~77° C. and then more ethyl acetate (100 ml) was added to achieve complete dissolution. The resulting clear-yellowish solution was stirred at reflux for ~30 minutes, and then the heating was removed. The mixture was stirred overnight at room temperature.

The resulting suspension was filtered and the collected yellow solids were rinsed on the funnel with ethyl acetate (30 ml). The wet solid was dried in vacuum oven at 40-50° C., over 4 hours, to obtain 8.53 g of yellow crystalline product (total yield ~17%).

$^1$H NMR: consistent with structure; HPLC: 99.94 area %; DSC: 228.68° C., 151 J/g.

Example 3: Micronization of Naphthofuran Compound

For example, Compound 1 crystals were milled and passed through a 160 micron (μm) sieve (Sieve #100, 150 μm opening) to generate the crystals of approximately 160 microns or less.

For example, Compound 1 crystals were milled (The Retsch Ultra centrifugal Mill ZM 200; Single pass, at 18,000 rpm using 0.25 mm screen) to a median particle size of about 20 micron. Table 3 presents the resultant distribution of particle sizes (Malvern 2000 with the Hydro 2000S wet accessory). The columns present the maximum size of particles in the cumulative percent total presented in the subscript at the header of the column. For example, the column $D_{90}$ presents the size for which 90% of the particles have an equal or lesser size. The column $D_{50}$ represents the median size—half of the particles have a greater size, and half of the particles have an equal or lesser size.

TABLE 3

Particle Size Distribution of Milled Compound 1

| | Particle Size (microns) | | |
|---|---|---|---|
| | $D_{90}$ | $D_{50}$ | $D_{10}$ |
| Sample B | 48.9 | 20.2 | 2.3 |

For example, Compound 1 crystals were micronized using a jet milling method (4" Jet Mill, Venturi pressure=40, Mill pressure=100, Feed rate=1304 g/hour) to a median particle size of about 2 micron, as presented in Table 4. Particle size analysis was performed using a dry particle method (Sympatec Helos/KF Particle Size Analyzer).

| Particle Size Distribution of Micronized Compound 1 | | | |
|---|---|---|---|
| | Particle Size (microns) | | |
| | $D_{90}$ | $D_{50}$ | $D_{10}$ |
| Sample A | 4.63 | 2.07 | 0.53 |

A cumulative distribution function derived from a log-normal model of particle size distribution provided a good fit to the data presented in Table 4. The cumulative distribution function was represented as $$CDF(d) = \frac{1}{2}\left(1 + \text{erf}\left(\frac{\ln(d) - \ln(d_{median})}{\sigma\sqrt{2}}\right)\right),$$

where erf is the error function, d is the particle diameter variable, $d_{median}$ is the median particle size, and $\sigma$ is a parameter related to the breadth of the cumulative distribution function. CDF(d) represents the fraction of particles having a size less than or equal to d. Setting $d_{median}$ to the observed median of 2.07 micron, fitting of the model yielded a value of $\sigma$=1.06. The model indicated a mean diameter of 3.6 micron and a mode diameter of 0.67 micron. The model also suggests a specific area of the particles of 2200 m²/kg, although this does not account for factors such as surface roughness.

Example 4: HPLC Assay

This HPLC method is to assess purity of naphthofuran, e.g., 2-acetylnaphtho[2,3-b]furan-4,9-dione (Compound 1), and its reaction completion by HPLC. All components will be expressed in area percent of the total peaks within the chromatogram.

1. Apparatus ans Materials

TABLE 5A

| Apparatus | HPLC system with UV detector and integration system |
|---|---|
| Column | Phenomenex Luna C18(2) 5-μm, 4.6-mm × 250-mm (P/N 00G-4252-E0) or equivalent |
| pH meter | calibrated the day of use |
| Acetonitrile | HPLC Grade |
| Dimethylsulfoxide (DMSO) | ACS Grade or better |
| Phosphoric acid | ACS reagent |
| Potassium phosphate, dibasic | ACS reagent |
| Compound 1 | Reference Material |

2. Solution Preparations 10 mM Phosphate Buffer

Weigh 1.74 g of Potassium Phosphate, dibasic and dilute with 1 L of Purified Water (adjust weights and volumes for amount needed). Adjust the pH with Phosphoric Acid to pH 6.8.

Mobile Phase A

Prepare Mobile Phase A by mixing the 10 mM phosphate buffer and acetonitrile to a 80:20 buffer:acetonitrile ratio. Degas.

Mobile Phase B

Prepare Mobile Phase B by mixing the 10 mM phosphate buffer and acetonitrile to a 20:80 buffer:acetonitrile ratio. Degas.

Diluent

Mobile Phase A will be used as the diluent for all sample and standard preparations.

3. Standards Preparations

Compound 1 Stock Standard (Concentration≈1.0 mg/mL)

It will be prepared weighing 10 mg of Compound 1 Reference material into a 20 mL scintillation vial; record weight±0.01 mg. Add 10 mL of DMSO and sonicate until the solids dissolve.

$$\text{Concentration} = \frac{(\text{Wt. Reference Standard, mg}) \times \text{Standard Decimal Purity}}{(\text{Volume of Stock Solution, mL})}$$

Stock Test Samples (Concentration≈1.0 mg/mL)

Test Solutions will be prepared by weighing 10 mg of sample in a 20 mL scintillation vial and diluting with 10 mL of DMSO.

$$\text{Concentration} = \frac{(\text{Wt. Sample, mg})}{(\text{Volume of Stock Solution, mL})}$$

Working Test Samples (Concentration≈0.01 mg/mL)

This solution is prepared by transferring 1 mL into a 100 mL volumetric flask and diluting with diluent solution.

$$\text{Concentration} = \frac{\text{Stock Test Sample Concentration} \times (\text{volume transferred, mL})}{(\text{Volume of Working Solution, mL})}$$

4. Instrument Operating Conditions

TABLE 5B

| Flow Rate | 0.8 mL/min. |
|---|---|
| Column temp | 30° C. |
| Detector Wavelength | 270 nm |
| Injection Volume | 40 μL |
| Gradient Profile | 0-5 min-0% B to 0% B |
| | 5-19 min- 0% B to 90% B |
| | 19-24 min-90% B to 90% B |
| | 24-29 min-90% B to 0% B |
| | Note: 5 min equilibration time between injections at 100% A |
| Run Time | 29 min |

5. Operating Procedure

Inject solutions in the following sequence:
1. Diluent blank (1×)
2. Compound 1 Working Standard (5×)
3. Test Solutions (2× each)
4. Working Standards (1× each)

6. System Suitability

The system is suitable for use if the following criteria are met.
1. Diluent blank injection at the beginning of the sequence contains no interfering peaks with any identified impurities
2. The initial, 5 replicate injections of the Compound 1 working standard have (1) % $\text{RSD}_{peak\ area}$<3.0%; (2) % $\text{RSD}_{retention\ time}$<3.0%; and (3) mean tailing factor <2.0.
3. In the chromatogram for the bracketed standard, (1) retention time is 97.0-103.0% of the mean retention time from the initial suitability injections and (2) its area % is 97.0-103.0% of the initial value.

7. Calculations

All peaks will be reported as area % of the total peaks in the chromatogram, this will be calculated by the integration software by way of the following formula:

$$\text{Area \%} = \frac{\text{Area counts of peak}}{\text{Total area of all peaks}} \times 100$$

NMR and TLC

TABLE 5C

| NMR | |
|---|---|
| Apparatus | Varian Inova 500 NMR Spectrometer |
| Pulse Sequence | S2pul |
| Solvent | CDC13 |
| Temp. | 25.0° C./298.1 K |
| Relax delay | 1.000 sec |
| Pulse | 45.0 degrees |
| Acq. time | 2.732 sec |
| Width | 11992.2 Hz |
|  | 32 repetitions |
| OBSERVE H1 | 499.7029706 MHz |
| FT size | 65536 |
| Total time | 1 min, 50 sec |

TABLE 5D

| TLC on silica gel | |
|---|---|
| eluent | ethyl acetate:hexane, 1:1 |
| visualization | UV |
| $Rf_{401}$ | ~0.7 |
| $Rf_{NDHF}$ | ~0.6 |

Example 5: Preparation of Crude 2-Acetylnaphtho[2,3-b]Furan-4,9-Dione

Another procedure for the preparation of Compound 1 is summarized as follows.

Bromine (0.95 equiv) is added to methyl vinyl ketone (MVK, 1.0 equiv) at −20 to −15° C. via an addition funnel while maintaining the reaction temperature below 0° C. The reaction mixture is then stirred at −10 to 0° C. for an additional 2 to 3 hours, followed by addition of Tetrahydrofuran (6 vol) and cooling of the reaction mixture to −20 to −10° C. Triethylamine (1.1 equiv) is then added with vigorous stirring while maintaining the reaction temperature below 0° C. The resulting slurry is stirred at −15 to −5° C. for a minimum of 10 hours, then warmed to −5 to 5° C. and filtered. The filtrate is then analyzed via in-process $^1$H NMR to determine the amount (wt. %) of intermediate bromomethyl vinyl ketone (BrMVK) present, and held at −25 to −10° C. until further use.

Next, Tetrahydrofuran (3.15 vol) in a clean reaction vessel is charged with 2-Hydroxy-1,4-Naphthoquinone (1.0 equiv relative to the calculated amount of BrMVK from in-process $^1$H NMR). The resulting orange slurry is stirred briefly, then 1,8-Diazabicyclo[5.4.0]undec-7-ene (DBU, 1.1 equiv) is added while maintaining a temperature at, or below, 45° C. The reaction mixture is then stirred at 40 to 45° C. for a minimum of 1 hour, heated to 50 to 55° C. and the BrMVK solution added via an addition funnel while maintaining the reaction temperature at 50 to 60° C. The reaction mixture is then stirred at 50 to 55° C. for approximately 18 hours until less than 5% 2-Hydroxy-1,4-Naphthoquinone remains. The reaction mixture is then concentrated, co-evaporated twice with Ethanol, and recrystallized from Ethanol/Water (1:1). The solids are dried under vacuum at 35 to 45° C. The crude solids and Charcoal G-60 (100 wt %) are then suspended in Acetonitrile and heated at 70 to 75° C. for 2 hours, filtered and washed with hot Acetonitrile. The filtrate is then concentrated to 1/3 volume, cooled to 0 to 5° C., and filtered. The solids are then dried under vacuum at 45 to 50° C. These crude solids are then reslurred in Ethyl Acetate at reflux for 6 hours, cooled to room temperature, filtered, and washed with Ethyl Acetate. The material is then dried under vacuum at 45 to 50° C. and packaged for final release.

Example 6: Clinical Trial: Safety and Efficacy

Compound 2-acetylnaphtho[2,3-b]furan-4,9-dione was chosen to enter Phase I clinical trial after receiving IND approval from US FDA and Health Canada, which was a dose escalation study in adult patients with advanced cancer who had failed standard therapies. Each cycle consists of twice-daily oral administration of the compound for 4 weeks. Cycles were repeated every 4 weeks (28 days) until progression of disease, unacceptable toxicity, or another discontinuation criterion is met. The dose escalation trial was conducted as open label and multicenter trial. A modified Simon accelerated titration scheme was used for dose escalation.

The primary objective of the trial was to determine the safety, tolerability, and recommended phase II dose (RP2D). The secondary objectives of the trial were to determine the pharmacokinetic profile of the compound, pharmacodynamics of the compound, and preliminary antitumor activity of the compound.

The inclusion criteria included histologically or cytologically confirmed solid tumor that is metastatic, unresectable, or recurrent; >18 years of age; Measurable disease by RECIST; and Karnofsky ≥70%. The exclusion criteria included chemotherapy, radiotherapy, immunotherapy or investigational agent within 4 weeks of first dose; surgery within 4 weeks of first dose; and known brain metastases.

The demographics and baseline disease characteristics of the patients selected under above criteria were summarized in Table 6.

TABLE 6

| Summary of Subjects with Signs of Activity | | | |
|---|---|---|---|
| Median Age, years (range) | 58 (28-91) | Tumor Type, N (%) | |
| Gender, N(%) | | Colorectal | 18 (44%) |
| Male | 30 (73%) | Gastric/GEJ | 3 (7%) |
| Female | 11 (27%) | NSCLC | 3 (7%) |
| Race, N(%) | | Pancreatic | 3 (7%) |
| Caucasian | 34 (83%) | Prostate | 3 (7%) |
| Asian | 4 (10%) | Head and Neck | 2 (5%) |
| Black | 1 (2%) | Melanoma | 2 (5%) |
| Other/Unknown | 2 (5%) | Other* | 7 (17%) |
| Prior Therapies | | | |
| ≥3 | 32 (78%) | | |
| 2 | 5 (12%) | | |
| 1 | 4 (10%) | | |

Of those patients, 10 cohorts were assessed at doses ranging from 20 mg to 2000 mg/day. No dose limiting toxicity was observed. The most common adverse events were: diarrhea, nausea, and fatigue. Grade 3 or greater events include: fatigue and diarrhea. The adverse events were summarized in Table 7.

TABLE 7

Summary of Adverse Events P

| Organ System | Adverse Event* | Any Grade # Subjets | Any Grade % | Grade 3 # Subjects | Grade 3 % |
|---|---|---|---|---|---|
| DIGESTIVE | Diarrhea | 30 | 73.2% | 2 | 4.9% |
| | Vomiting | 20 | 48.8% | 0 | 0.0% |
| | Nausea | 20 | 46.6% | 0 | 0.0% |
| | Abdominal cramps/pain | 22 | 53.7% | 0 | 0.0% |
| | Anorexia | 14 | 34.1% | 0 | 0.0% |
| | Loose/Soft Stools | 8 | 19.6% | 0 | 0.0% |
| | Dysgusia | 5 | 12.2% | 0 | 0.0% |
| | Reflux | 4 | 9.8% | 0 | 0.0% |
| CONSTITUTIONAL | Fatigue | 18 | 43.9% | 1 | 2.4% |
| | Weakness | 6 | 14.6% | 0 | 0.0% |
| | Weight loss | 5 | 12.2% | 0 | 0.0% |
| URINARY | Urine Color Change | 10 | 24.4% | 0 | 0.0% |
| METABOLIC | Dehydration | 3 | 7.3% | 0 | 0.0% |
| NEUROLOGIC | Dizziness | 6 | 12.2% | 0 | 0.0% |

*Observed in 10% of more of study subjects adverse events using CTCAE v 3.0

In the 20 mg daily administration, surprisingly high concentration of the compound in urine of the patient was observed. Furthermore, we tested antitumor activity of the Compound of the Invention in patient urine, and found that the Compound remained potent against cancer cells.

Of the patients dosed, disease control (disease stabilization and tumor regression) was observed in 65% of patients evaluable for tumor response in a variety of tumors that had been refractory to chemotherapies, including colorectal adenocarcinoma, head and neck cancer, breast cancer, gastric cancer, ovarian cancer, chondrosarcoma, adrenocorticoid carcinoma, and melanoma. There was one complete regression of a colon cancer metastatic lesion to kidney (Patient 0001). Patients treated with Compound 1 exhibited a dramatic lack of new metastatic tumor lesions. Out of 24 evaluable patients with advanced refractory cancers, over 80% showed no metastatic tumors.

The patients enrolled with signs of activity were summarized in Table 9.

We also found that high levels of p-STAT3 in tumor tissues prior to the treatment by immunohistochemistry using anti-p-STAT3 antibody predicts a good response of their tumor to Compound 1.

Pharmacokinetics profile with oral bid dosing was also studied. The plasma concentration of the drug reached several folds over the efficacious concentration (in vitro IC50) as illustrated in Table 8. However, drug concentration did not maintain at high levels for long and decreased below the efficacious concentration rapidly.

TABLE 8

Pharmacokinetic summary for different dose levels

| Total Daily Dose (mg/kg) | Dosing Schedule | $t_{max}$ (h) | $C_{max}$ (uM) | $C_{24h}$ (uM) | $AUC_{0-24}$ (uM · h) | $T_{1/2,t}$ (h) | AUC (uM · h) |
|---|---|---|---|---|---|---|---|
| 20 | qd | 3.0 | 0.49 | 0.03 | 2.01 | 18.5 | 2.70 |
| 40 | qd | 0.5 | 0.50 | 0.03 | 3.44 | 4.5 | 3.62 |
| 80 | qd | 1.5 | 2.24 | 0.07 | 12.77 | 5.2 | 13.32 |
| 80 | bid q4h | 8.1 | 0.90 | 0.03 | 7.95 | 3.6 | 8.13 |

TABLE 9

Patients Enrolled in Phase I

| Total Daily Dose (mg) | Tumor Type | Weeks on Study | Best Response (RECIST 11) |
|---|---|---|---|
| 20 | Colon adencarcinoma | 76 | SD (22% regression) |
| 80 | Head and fleck carcinoma | 17 | SD |
| 320 | Colon adenocarcinoma | 24 | SD |
| 320 | Colon adenocarcinoma | 12 | SD |
| 400 | Gastric adenocarcinoma | 19 | SD |
| 400 | Ovarian carcinoma | 16 | SD (CA125 normalization) |
| 400 | Colon adenocarcinoma | 11 | SD (CEA, 50%) |
| 500 | Breast carcinoma (triple negative) | 29 | SD (remaining lesion hollowed, surgically resected; patient disease free) |
| 800 | Chondrosarocoma | 13 | SD |
| 1000 | Adrenocarticoid carcinoma | 17 | SD |
| 1000 | Colon: adencarcinoma | 16 | SD |
| 1400 | Melanona | 16 | SD |

TABLE 8-continued

Pharmacokinetic summary for different dose levels

| Total Daily Dose (mg/kg) | Dosing Schedule | $t_{max}$ (h) | $C_{max}$ (uM) | $C_{24h}$ (uM) | $AUC_{0-24}$ (uM · h) | $T_{1/2,t}$ (h) | AUC (uM · h) |
|---|---|---|---|---|---|---|---|
| 160 | bid q4h | 3.9 | 1.33 | nd | nd | nd | nd |
| 320 | bid q4h | 3.8 | 2.92 | 0.24 | 33.12 | 5.7 | 38.26 |
| 400 | bid q4h | 7.9 | 3.75 | 0.62 | 40.25 | 6.9 | 48.17 |
| 600 | bid q4h | 3.2 | 2.67 | 0.42 | 27.76 | 9.0 | 37.15 |
| 800 | bid q4h | 4.3 | 3.04 | 0.16 | 26.06 | 4.0 | 27.00 |
| 1000 | bid q4h | 6.6 | 4.97 | 0.29 | 45.11 | 6.6 | 50.71 |
| 1000 | bid q6h | 5.7 | 1.36 | 0.33 | 15.84 | 12.7 | 22.90 |
| 1400 | bid q4h | 2.9 | 2.05 | 0.65 | 28.20 | 13.6 | 45.04 |
| 1500 | tid q4h | 7.3 | 3.75 | 0.94 | 46.43 | 8.2 | 59.85 |
| 2000 | bid q4h | 6.3 | 1.69 | 0.80 | 25.90 | 17.2 | 45.80 |

To maintain drug plasma concentration at or above the efficacious level for a desirable duration and to further increase peak plasma concentration, we studied the pharmacokinetics of a 500 mg BID regimen (at 4 hour interval between two doses on the same day or "q4h"), and compared it to that of a 500 mg QD regimen (FIG. 1). Surprisingly, no significant difference was observed in terms of pharmacokinetics between the two dosing regimens. Previously, it was expected that with a BID regimen, drug level in patient plasma would exhibit another pronounced peak as dosing is doubled within the same day compared to a QD regimen. However, administration of Compound 1 twice q4h failed to sustain drug level for a desirable length of time after the first dose during the same 24-hour period. In another suitable dosing regimen, 500 mg of Compound 1 were administered three times a day (TID) to human subjects. Rather disappointingly, the level of patient exposure to Compound 1 was not significantly improved by three times a day dosing as compared to twice daily dosing.

Example 7: Dosing Regimens and New Formulation

The therapeutically effective amount of the pharmaceutical composition including particles, polymorphs and/or purified forms of a Compound of the Invention can be a total daily dose in the range of from about 160 mg to about 1000 mg, e.g., at about 960 mg. However, to achieve effective dose levels, the clinical study faced a challenge of pill burden suffered by the patients. To overcome the pill burden issue and to solve the problem of maintaining drug concentration at or above the minimal efficacious level for a desirable duration, higher strength capsules were designed in a new formulation (DP2A).

However, with the higher strength capsules, we observed worsening gastrointestinal adverse effects including nausea, vomiting, and diarrhea in patients. When we studied the relationship between plasma drug concentration and adverse effects in an additional Phase I clinical study, part of which is summarized in Table 10 below, to our surprise, the data indicates that the severity of gastrointestinal adverse events does not seem to correlate with plasma pharmacokinetic parameters as one would normally suspect (see Tables 10 and 11).

TABLE 10

Clinical Comparison of Drug Pharmacokinetics and Adverse Events observed

| Patient | Plasma PK parameters (single 500 mg dose - fed) | AE summary |
|---|---|---|
| 0053 | Higher exposure (Cmax: 6.61 uM;A $UC_{0-24}$: 79.64 uM * hr) | No significant gastrointestinal issues at 500 mg bid q4h |
| 0054 | Higher exposure (Cmax: 6.25 uM; $AUC_{0-24}$: 49.82 uM * hr) | No significant gastrointestinal issue sat 500 mg bid q4h |
| 0061 | Lower exposure (Cmax: 1.54 uM; $AUC_{0-24}$: 10.61 uM * hr) | Intolerable grade 2 fatigue, cramping, diarrhea, and nausea starting at 500 mg bid q4h and persisting at 375 mg/250 mg/250 mg q4h |
| 0070 | Lower exposure (Cmax 2.25 uM; $AUC_{0-24}$: 20.09) | Grade 3 diarrhea at 375 mg/250 mg/250 mg q4h |

TABLE 11

Summary of Adverse Events in Dosing Regimens under Study
Subjects with Adverse Events Possibly Related to BBI608

| | | q 4 h dosing (N = 17) | | | | q 12 h dosing (N = 11) | | | |
|---|---|---|---|---|---|---|---|---|---|
| | | Grade 1 or 2 | | Grade 3 | | Grade 1 or 2 | | Grade 3 | |
| Organ System | Adverse Event | # Subjects | % | # Subjects | % | # Subjects | % | # Subjects | % |
| DIGESTIVE | Diarrhea | 14 | 82.4% | 4 | 23.5% | 7 | 63.6% | 0 | 0.0% |
| | Vomiting | 7 | 41.2% | 0 | 0.0% | 1 | 9.1% | 0 | 0.0% |
| | Nausea | 8 | 47.1% | 1 | 5.9% | 2 | 18.2% | 0 | 0.0% |
| | Abdominal cramps/pain | 13 | 76.5% | 1 | 5.9% | 5 | 45.5% | 0 | 0.0% |
| | Bloated abdomen | 4 | 23.5% | 0 | 0.0% | 0 | 0.0% | 0 | 0.0% |
| | Fatigue/weakness | 10 | 58.8% | 3 | 17.6% | 4 | 36.4% | 1 | 9.1% |
| | Anorexia | 10 | 58.8% | 3 | 17.6% | 1 | 9.1% | 0 | 0.0% |
| | Reflux (also heartburn) | 1 | 5.9% | 0 | 0.0% | 0 | 0.0% | 0 | 0.0% |
| | Dysgusia | 1 | 5.9% | 0 | 0.0% | 0 | 0.0% | 0 | 0.0% |
| | Xerostomia | 4 | 23.5% | 0 | 0.0% | 2 | 18.2% | 0 | 0.0% |
| | Rectal/Anal Burning | 3 | 17.6% | 0 | 0.0% | 1 | 9.1% | 0 | 0.0% |
| | Flatulence | 2 | 11.8% | 0 | 0.0% | 2 | 18.2% | 0 | 0.0% |

TABLE 11-continued

Summary of Adverse Events in Dosing Regimens under Study
Subjects with Adverse Events Possibly Related to BBI608

| | | q 4 h dosing (N = 17) | | | | q 12 h dosing (N = 11) | | | |
|---|---|---|---|---|---|---|---|---|---|
| | | Grade 1 or 2 | | Grade 3 | | Grade 1 or 2 | | Grade 3 | |
| Organ System | Adverse Event | # Subjects | % | # Subjects | % | # Subjects | % | # Subjects | % |
| CONSTITUTIONAL | Weight loss | 8 | 47.1% | 0 | 0.0% | 0 | 0.0% | 0 | 0.0% |
| URINARY | Urine Color Change | 2 | 11.8% | 0 | 0.0% | 0 | 0.0% | 0 | 0.0% |
| METABOLIC | Dehydration | 1 | 5.9% | 0 | 0.0% | 0 | 0.0% | 0 | 0.0% |
| | hypophosphatemia | 1 | 5.9% | 1 | 5.9% | 0 | 0.0% | 0 | 0.0% |
| NEURO/PSYCH | Depression | 0 | 0.0% | 0 | 0.0% | 1 | 9.1% | 0 | 0.0% |

After exhausting conventional solutions, our breakthrough came from an unexpected change to the drug intake protocol. Surprisingly, we have found that the intake interval between doses in accordance with some preferred embodiments of the invention turned out to be the key factor for both prolonging drug exposure as well as decreasing gastrointestinal side effect. Even more surprising was that, instead of condensing the drug administrations by shortening the interval between each intake as one would intuitively try when the problem was rapid drop of drug concentration in the blood stream, we found that lengthening such interval actually solved the problem. For example, a preferred interval between administrations of the drug turned out to be a period ranging from about 8 hours to about 14 hours, more preferably, from about 10 hours to about 13 hours. In a particular embodiment, a Compound of the Invention or a related composition and form, is administered, on average over a period, twice daily at an interval of about 12 hours between doses where each does is about 480-500 mg BID.

In yet another suitable dosing regimen, about or above 20 mg of Compound 1 was administered once daily to human subjects. This dosing regimen, referred to herein as 20 mg QD, has shown therapeutically active levels in patients, but the drug is rapidly cleared from the blood in humans. However, as the drug cleared from blood stream into the urine through kidney, it showed signs of particularly potent antitumor activity in a kidney with colon cancer lesions due to very high concentration of the drug in urine. In general, this dosing regimen has shown good tolerability in humans.

In yet another suitable dosing regimen, Compound 1 was administered with a fluid, e.g., a milk or water, with empty stomach which improves pharmacokinetical exposure (Table 12). Counterintuitively, milk helped patients with gastrointestinal adverse effects.

TABLE 12

Effect of Milk on Compound 1 Pharmacokinetics

| PK Parameter | Fasting | with Milk | Fold Change |
|---|---|---|---|
| Cmax (uM) | 2.01 | 3.05 | 1.52 |
| $AUC_{0-24hrs}$ | 20.12 | 31.40 | 1.56 |
| Cmax (uM) | 2.55 | 2.89 | 1.13 |
| $AUC_{0-24hrs}$ | 20.72 | 32.16 | 1.55 |

In yet another suitable dosing regimen, Compound 1 was administered with food which delayed the Tmax (Table 13).

TABLE 13

Taking Compound 1 with Food Causes a Delay in Tmax

| | Tmax (hr) | | |
|---|---|---|---|
| Patient | Fasting | With Milk | With Food |
| 20 | 2 | 2 | 8 |
| 21 | 6 | 6 | 6 |
| 22 | 8 | 8 | 10 |
| 24 | — | 6.3 | 10 |
| 27 | — | 0.5 | 6 |
| 28 | — | 6 | 10 |

In yet another suitable dosing regimen, the pill burden issue was addressed through a new drug formulation (DP2A). The new formulation replaces a large portion of the surfactant GELUCIRE™ 44/14 used in the DP1 formulation with another surfactant Labrafil, and reduces the capsule dimension from a size 00 to a size 1 or size 2, which is a significant reduction. The new formulation was able to maintain similar bioavailability (Figure. 2). Components of the two formulations are summarized below (Table 14):

TABLE 14

New pharmaceutical formulation (DP2A) reduces pill size

| | | | 50 mg Capsule (DP1) | | 125 mg capsule (DP2A) | | 80 mg capsule (DP2A) | |
|---|---|---|---|---|---|---|---|---|
| Component | Grade | Function | mg/capsule | % | mg/capsule | % | mg/capsule | % |
| Compound of the Invention | n House | Active | 50 | 8.34% | 125 | 27.18% | 80 | 27.18% |
| SLS | USP/NF | Surfactant | — | | 1.2 | 0.27% | 0.8 | 0.27% |
| Gelucire 44/14 (lauroyl polyoxylglycerides) | USP/NF | Diluent | 522.5 | 87.08% | 66.8 | 14.51% | 42.7 | 14.51% |
| Tween 80 (polysorbate 80) | NF | Surfactant | 27.5 | 4.58% | — | | — | |

TABLE 14-continued

New pharmaceutical formulation (DP2A) reduces pill size

| Component | Grade | Function | 50 mg Capsule (DP1) | | 125 mg capsule (DP2A) | | 80 mg capsule (DP2A) | |
|---|---|---|---|---|---|---|---|---|
| | | | mg/capsule | % | mg/capsule | % | mg/capsule | % |
| Labrafil M2125 CS (linoleoyl polyoxylglycerides) | USP/NF | Diluent | — | | 267 | 58.04% | 170.9 | 58.04% |
| White opaque Licap capsule | n House | Encapsulate | 1 (size 00) | | 1 (size 1) | | — | |
| Gold opaque Licap Capsule | n House | Encapsulate | — | | — | | 1 (size 1 or size 2) | |

Additional studies were run using an oral formulation of the Compound of the Invention, specifically a higher strength capsule formulation (DP2A). As described herein, the Compound of the Invention blocks cancer stem cell (CSC) self-renewal and induces cell death in CSC as well as non-stem cancer cells by inhibiting Stat3, β-catenin, and Nanog pathways, and has shown potent anti-tumor and anti-metastatic activities pre-clinically. In the phase I studies described above, the Compound demonstrated tolerability as well as signs of anti-cancer activity in patients with solid tumors. The studies described herein were designed as a phase 1 extension study to evaluate a formulation designed for pivotal trials to determine pharmacokinetics (PK) in patients with advanced cancer.

On Day 1, patients received a single 500 mg dose of an oral administration formulation of the Compound of the Invention (DP1). On Day 4 and Day 8, a higher strength capsule designed for pivotal trials (DP2A) was given with fasting then fed conditions. DP2A was then administered daily until disease progression or unacceptable toxicity. Endpoints were safety, PK and preliminary anticancer activity.

DP2A was evaluated in 24 patients. No significant difference in plasma exposure between DP1 and DP2A, and no significant food effect were observed. Nine patients received the Compound DP2A 500 mg twice daily 4 h apart (DP2A-4h), and 15 patients received the Compound DP2A 500 mg bid 12 h apart (DP2A-12h). Despite PK equivalence to the Compound DP1, DP2A-4 h was associated with higher frequency of gastrointestinal (GI) adverse events (AE) than observed in the prior study described above, including diarrhea, abdominal cramps, nausea/vomiting, anorexia, and fatigue. In contrast, DP2A-12 h had fewer GI AE and was selected for the extension study. Among 15 patients receiving DP2A-12h, prolonged stable disease was observed in 2 of 7 non-CRC patients (ovarian cancer-16 week) and among 8 CRC patients enrolled, disease control was observed in 67% evaluable for response (4/6), with progression free survival and overall survival at 17 weeks and 39 weeks, respectively.

The recommended dosing regimen for the Compound in pivotal trials was determined to be about 500 mg bid q12 h. Signs of anticancer activity were observed in patients with CRC and ovarian cancer.

Example 8: Co-Therapy with an Antimitotic Agent

The Compound of the Invention was used in combination with an antimitotic agent, especially those proven to be effective chemotherapy agents, to successfully treat patients. Examples of antimitotic agents that may be useful in a co-therapy with the Compound of the Invention include and are not limited to: paclitaxel (Abraxane/Taxol), docetaxel (taxotere), BMS-275183, xyotax, tocosal, vinorlebine, vincristine, vinblastine, vindesine, vinzolidine, etoposide (VP-16), teniposide (VM-26), ixabepilone, larotaxel, ortataxel, tesetaxel, and ispinesib.

A Phase Ib study was designed to evaluate the combined use of the Compound of the Invention with paclitaxel in patients with advanced malignancies. The studies were designed as a Phase Ib dose-escalation study to determine safety, tolerability, RP2D, and preliminary anti-cancer activity of the Compound of the Invention when used in conjunction with weekly paclitaxel. The Compound was administered in 3 escalating dose cohorts (200 mg BID, 400 mg BID, 500 mg BID) in combination with paclitaxel (80 mg/m2 weekly; 3 of every 4 weeks) until progression of disease, unacceptable toxicity, or other discontinuation criteria was met.

24 patients were enrolled in this study. The Compound of the Invention monotherapy RP2D could be given in combination with paclitaxel in full dose. Maximum tolerated dose (MTD) was not determined. No new adverse events were observed, and the safety profile was similar to that of each agent as monotherapy. The most common adverse events included grade 1 and 2 diarrhea, abdominal cramps, nausea, vomiting. Grade 3 events related to protocol therapy occurred in 4 patients and included diarrhea, dehydration, and weakness. No significant pharmacokinetic interactions were observed. Disease control (i.e., the sum of complete responses (CR)+partial responses (PR)+stable disease (SD)) was observed in 10 of 15 (67%) evaluable patients. As shown in Table 15 below, of 5 patients with refractory gastric/gastroesophageal junction (GEJ) adenocarcinoma enrolled, 2 had PR (48% and 45% regressions), 1 had SD with 25% regression, and 2 (who failed prior taxane) had prolonged SD ≥24 wks.

This Phase Ib study demonstrated that the Compound of the Invention and weekly paclitaxel can be safely combined at full dose. Encouraging anti-tumor activity was observed in patients with gastric and GEJ adenocarcinoma.

TABLE 15

Signs of anti-tumor activity with co-therapy of the Compound of the Invention and paclitaxel

| Patient | Diagnosis | Paclitaxel Dose* | Best Response |
|---|---|---|---|
| 0006 | Gastric Adenocarcinoma | 80 mg/m² | SD (25% lesion regression, 90% decrease in CEA) |
| 0018 | GEJ Adenocarcinoma | 80 mg/m² | PR (44% lesion regression) |
| 0019 | GEJ Adenocarcinoma | 80 mg/m² | PR (48% lesion regression) |
| 0021 | GEJ Adenocarcinoma | 80 mg/m² | SD (0% lesion growth) |
| 0024 | GEJ Adenocarcinoma | 80 mg/m² | SD (5% lesion growth) |

*Paclitaxel was administered intravenously once a week, for three out of every four weeks A Phase II study is on-going which extends from the phase Ib study and is continuing to enroll patients with Gastric/GEJ adenocarcinoma.

Phase II data for Gastric/GEJ adeno

| Patient | Diagnosis | Paclitaxel Dose | Best Response |
|---|---|---|---|
| 0037 | GEJ Adenocarcinoma | 80 mg/m² | PR (100% tumor lesion regression) |
| 0044 | GEJ Adenocarcinoma | 80 mg/m² | SD (17% growth) |
| 0046 | GEJ Adenocarcinoma | 80 mg/m² | PR (36% tumor lesion regression) |
| 0047 | GEJ Adenocarcinoma | 80 mg/m² | SD/PR (approximately 30% regression) |
| 0051 | GEJ Adenocarcinoma | 80 mg/m² | SD (measurements pending) |
| 0054 | GEJ Adenocarcinoma | 80 mg/m² | SD (measurements pending) |
| 0059 | Gastric Adenocarcinoma | 80 mg/m² | PR/CR (100% tumor lesion regression) |

In these studies, 7 of 9 evaluable gastric/GEJ patients showed activity in response to combination therapy with the Compound of the Invention and paclitaxel.

Example 9: P-STAT3 as a Predicative Biomarker

CRC patient's archival tumor tissue samples were analyzed through immunohistochemistry (IHC) using labeled antibodies against phosphorylated STAT3 (p-STAT3). As shown in FIG. 3A, the Compound of the Invention was very effective in inhibiting p-STAT3 expression. Even with dosage as low as 100 mg/kg QD (single daily dosage), there was almost no longer any detectable p-STAT3 in the patient tissue after treatment. And as the chart in FIG. 3B shows, for patients receiving the Compound of the Invention treatment (N=13), the overall survival (OS) is much more optimistic in those who had previously exhibited relatively high levels of p-STAT3. For instance, 40% of the patients with high p-STAT3 levels before treatment survived longer than 100 weeks whereas only 10% of those with low or no p-STAT3 levels before treatment survived beyond 100 weeks. This further confirms that the Compound of the Invention downregulates that STAT3 pathway, and that the STAT3 pathway is implicated in colorectal cancers.

The direct correlation between the p-STAT3 level and OS of CRC patient receiving treatment with the Compound of the Invention makes p-STAT3 a promising diagnostic biomarker that can be used to predict treatment effectiveness. Accordingly, p-STAT3 level can be used to screen patient pools for treatment with the Compound of the Invention.

Example 10: Nuclear β-Catenin as Predicative Biomarker

CRC patient's archival tumor tissue samples were analyzed through immunohistochemistry (IHC) using labeled antibodies against β-catenin. As shown in FIG. 4A, the Compound of the Invention was effective in removing or preventing the accumulation of β-catenin in cell nucleus in tumor tissues. And as the chart in FIG. 4B shows, for patients receiving treatment with the Compound of the Invention (N=13), the overall survival (OS) is much more optimistic in those found to have previously shown high levels of nuclear β-catenin prior to treatment. For instance, close to 40% of the patients with high nuclear β-catenin levels before treatment survived longer than 100 weeks whereas none of those with high levels of membranous β-catenin survived beyond 25 weeks. This further confirms that the Compound of the Invention disrupts or somehow modulates the β-catenin function, and that the β-catenin pathway is implicated in colorectal cancers.

The direct correlation between the nuclear β-catenin level and OS of CRC patient receiving treatment with the Compound of the Invention makes nuclear β-catenin level a promising diagnostic biomarker that can be used to predict treatment effectiveness. Accordingly, nuclear β-catenin level can be used to screen patient pools for treatment with the Compound of the Invention.

Example 11

Figure 5:
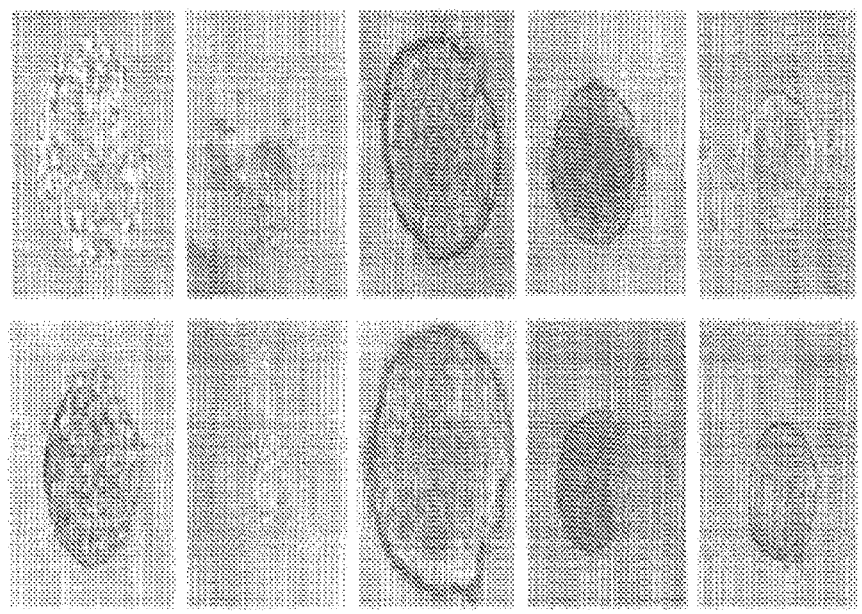
FIG. 5 shows $CD44^{high}$ cells growth being blocked by a Compound of the Invention. $CD44^{high}$ cells were isolated by FACS (FaDu) and were cultured in the absence of attachment and serum for 5 days to form primary spheres. Primary spheres were then dissociated in Accumax (eBioscience, San Diego, Calif.) to single cells, and were cultured as above for 72 hours before the addition of the indicated concentrations of therapeutic agents. After five days of treatment, representative sphere images were captured.
Figure 6A:
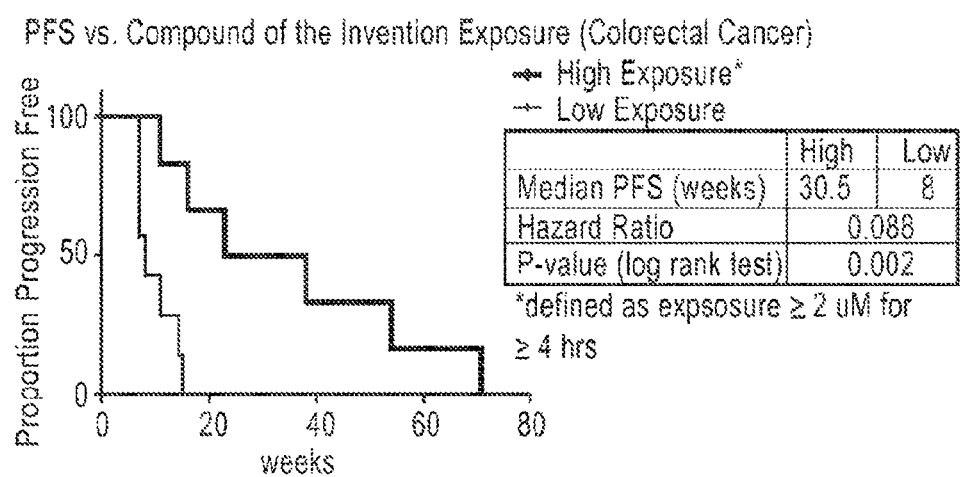
FIGS. 6A, 6B, and 6C are a series of graphs depicting that in human clinical studies, a Compound of the Invention was found to be effective in CRC patients.
Figure 6B:
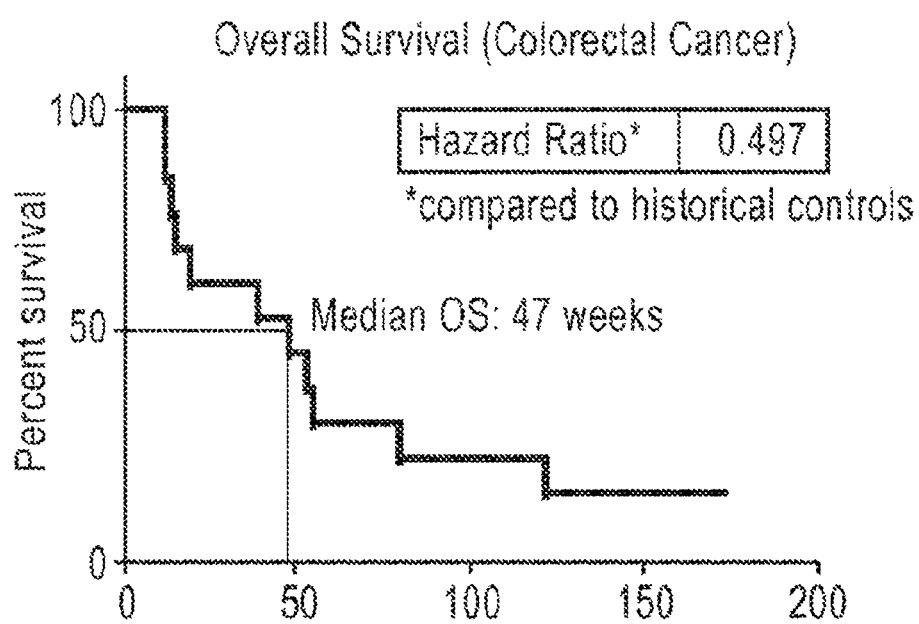
Figure 6C:
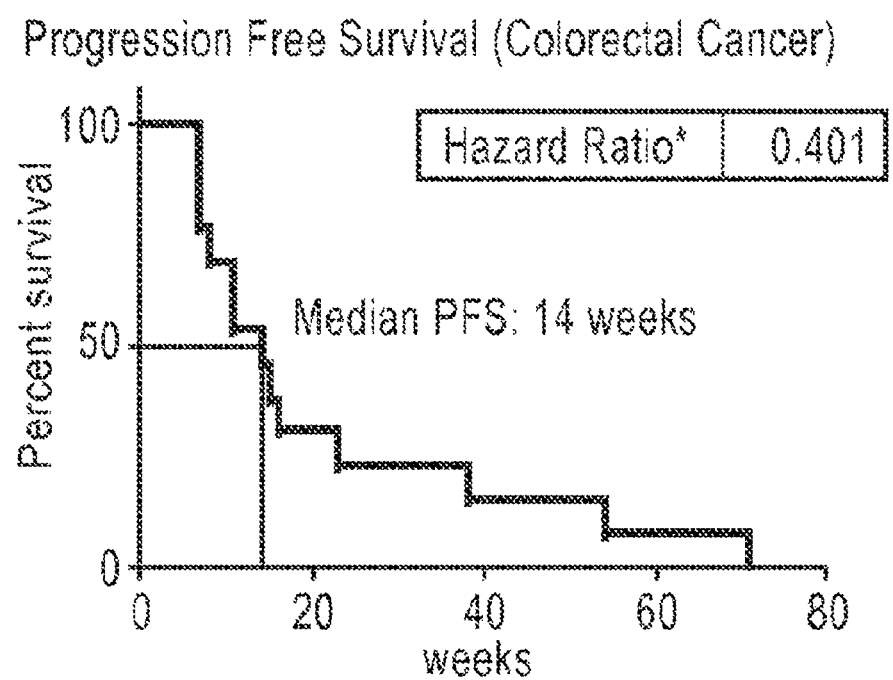

CD44$^{high}$ cells were isolated by FACS (FaDu) and their growth was blocked by a Compound of the Invention (FIG. 5).

In human clinical studies, a Compound of the Invention was found to be effective in CRC patients (FIG. 6).

Use of p-STAT3 and nuclear β-catenin as predicative biomarkers of treatment involving a Compound of the Invention is also studied (FIG. 7).

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A pharmaceutical composition, comprising:
   (a) 5 to 50% by weight of a therapeutically effective amount of a compound having $D_{50}$ less than 5.0 μm and the structure

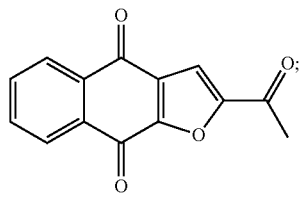 [SMILES: CC(=O)c1cc2c(o1)C(=O)c1ccccc1C2=O]

(b) 5 to 80% by weight of a polyoxylglyceride having a hydrophilic-lipophilic balance (HLB) greater than 10 and selected from the group consisting of lauroyl polyoxylglycerides, stearoyl polyoxylglycerides, and combinations thereof; and
   (c) 5 to 80% by weight of a polyoxylglyceride having a HLB less than 10 and selected from the group consisting of linoleoyl polyoxylglycerides, oleoyl polyoxylglycerides, lauroyl polyoxylglycerides, and combinations thereof.

2. The pharmaceutical composition according to claim 1, wherein the composition further comprises a surfactant in an amount of 0.05 to 5% by weight.

3. The pharmaceutical composition according to claim 2, wherein the surfactant is selected from the group consisting of sodium lauryl sulfate, sodium dodecyl sulfate, and combinations thereof.

4. The pharmaceutical composition according to claim 2, comprising, by weight, about 27.18% of the compound, about 0.27% of the surfactant, about 14.51% of the polyoxylglycerides of which HLB is more than 10, and about 58.04% of the polyoxylglycerides of which HLB is less than 10.

5. The pharmaceutical composition according to claim 1, comprising about 125 mg of the compound.

6. The pharmaceutical composition according to claim 1, comprising about 80 mg of the compound.

7. The pharmaceutical composition according to claim 1, wherein the weight ratio between the polyoxylglycerides of which HLB is more than 10 and the polyoxylglycerides of which HLB is less than 10 is from about 90/10 to about 10/90.

8. The pharmaceutical composition according to claim 1, wherein the weight ratio between the polyoxylglycerides of which HLB is more than 10 and the polyoxylglycerides of which HLB is less than 10 is from about 80/20 to about 20/80.

9. The pharmaceutical composition according to claim 1, wherein the polyoxylglyceride of which HLB is more than 10 is selected from the group consisting of lauroyl polyoxyl-32 glycerides, stearoyl polyoxyl-32 glycerides, and combinations thereof.

10. The pharmaceutical composition according to claim 9, wherein the polyoxylglyceride of which HLB is more than 10 is lauroyl polyoxyl-32 glyceride.

11. The pharmaceutical composition according to claim 1, wherein the polyoxylglyceride of which HLB is less than 10 is selected from the group consisting of linoleoyl polyoxyl-6 glycerides, oleoyl polyoxyl-6 glycerides, and combinations thereof.

12. The pharmaceutical composition according to claim 11, wherein the polyoxylglyceride of which HLB is less than 10 is linoleoyl polyoxyl-6 glyceride.

13. The pharmaceutical composition according to claim 1, wherein the composition is in the form of a capsule having a size of 1 or 2.

14. A pharmaceutical composition, comprising:
(a) 5 to 50% by weight of a therapeutically effective amount of a compound having $D_{50}$ less than 5.0 µm and the structure

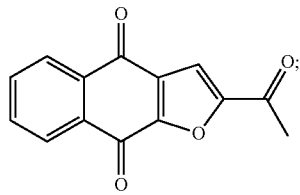 [SMILES: CC(=O)c1cc2c(o1)C(=O)c1ccccc1C2=O]

(b) 5 to 80% by weight of a lauroyl polyoxyl-32 glyceride having a hydrophilic-lipophilic balance (HLB) greater than 10;
(c) 5 to 80% by weight of a linoleoyl polyoxyl-6 glyceride having a HLB less than 10; and
(d) 0.05 to 5% by weight of sodium lauryl sulfate.

15. A pharmaceutical composition, comprising:
(a) about 80 mg of a compound having $D_{50}$ less than 5.0 µm and the structure

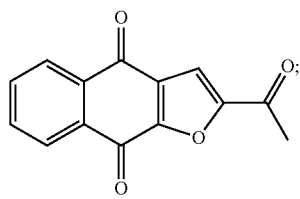

(b) about 42.7 mg of a lauroyl polyoxyl-32 glyceride having a hydrophilic-lipophilic balance (HLB) greater than 10;
(c) about 170.9 mg of a linoleoyl polyoxyl-6 glyceride having a HLB less than 10; and
(d) about 0.8 mg of sodium lauryl sulfate.

* * * * *

UNITED STATES PATENT AND TRADEMARK OFFICE
CERTIFICATE OF CORRECTION

PATENT NO. : 10,543,189 B2  
APPLICATION NO. : 16/543089  
DATED : January 28, 2020  
INVENTOR(S) : Chiang Jia Li et al.

Page 1 of 1

It is certified that error appears in the above-identified patent and that said Letters Patent is hereby corrected as shown below:

On the Title Page

<u>Item (63), Related U.S. Application Data</u>
Line 3, after "application No. 14/783,184", delete "filed as application No. PCT/US2014/033566 on Apr. 9, 2014, now abandoned." and insert -- filed on October 8, 2015, now abandoned, which is a U.S. National Stage Filing under 35 U.S.C. § 371 from International Application No. PCT/US2014/033566, filed on April 9, 2014, and published as WO 2014/169078 on October 16, 2014, now expired. --.

Signed and Sealed this  
Tenth Day of November, 2020

Andrei Iancu  
*Director of the United States Patent and Trademark Office*